(12) United States Patent
Stanford et al.

(10) Patent No.: US 11,339,448 B2
(45) Date of Patent: May 24, 2022

(54) TREATMENT OF ACUTE MYELOID LEUKEMIA

(71) Applicant: Ottawa Hospital Research Institute, Ottawa (CA)

(72) Inventors: William Stanford, Ottawa (CA); Caryn Ito, Ottawa (CA); Mitchell Sabloff, Ottawa (CA); Harinad Babu Maganti, Toronto (CA); Hani Jrade, Ottawa (CA); Harold Atkins, Ottawa (CA)

(73) Assignee: Ottawa Hospital Research Institute, Ottawa (CA)

(*) Notice: Subject to any disclaimer, the term of this patent is extended or adjusted under 35 U.S.C. 154(b) by 319 days.

(21) Appl. No.: 16/523,334

(22) Filed: Jul. 26, 2019

(65) Prior Publication Data
US 2020/0040403 A1 Feb. 6, 2020

Related U.S. Application Data

(60) Provisional application No. 62/711,173, filed on Jul. 27, 2018.

(51) Int. Cl.
*C12Q 1/6886* (2018.01)
*A61K 31/451* (2006.01)
*G01N 33/574* (2006.01)

(52) U.S. Cl.
CPC .......... *C12Q 1/6886* (2013.01); *A61K 31/451* (2013.01); *G01N 33/57426* (2013.01); *C12Q 2600/106* (2013.01); *C12Q 2600/158* (2013.01)

(58) Field of Classification Search
CPC .................................................. C12Q 1/6886
USPC ....................................................... 435/7.23
See application file for complete search history.

(56) References Cited

PUBLICATIONS

Von der Heide (Leukemia, 2017, 31: 1069-1078).*
Herold et al (Blood, 2014, 124(8): 1304-1311).*
Majeti et al (PNAS, 2009, 106(9): 3396-3401).*
Al-Khalaf et al., "Temporal Activation of XRCC1-mediated DNA Repair is Essential for Muscle Differentiation," Cell Discovery, Jan. 2016, vol. 2, pp. 15041.
Borthakur et al., "MDM2 Inhibitor, Nutlin 3a, Induces p53 Dependent Autophagy in Acute Leukemia by AMP Kinase Activation," PLoS One, Oct. 2015, vol. 10 (10), pp. e0139254.
Cancer Genome Atlas Research Network et al., "Genomic and Epigenomic Landscapes of Adult De Novo Acute Myeloid Leukemia," The New England Journal of Medicine, May 2013, vol. 368 (22), pp. 2059-2074.
Ceccaldi et al., "Homologous-Recombination-Deficient Tumours are Dependent on Pol theta-Mediated Repair," Nature, Feb. 2015, vol. 518 (7538), pp. 258-262.
Come et al., "Dual Mechanism of Daunorubicin-induced Cell Death in Both Sensitive and MDR-resistant HL-60 Cells," British Journal of Cancer, Mar. 1999, vol. 79 (7-8), pp. 1090-1097.
Craddock et al., "Factors Predicting Outcome After Unrelated Donor Stem Cell Transplantation in Primary Refractory Acute Myeloid Leukaemia," Leukemia, May 2011, vol. 25 (5), pp. 808-813.
Csaszar et al., "Rapid Expansion of Human Hematopoietic Stem Cells by Automated Control of Inhibitory Feedback Signaling," Cell Stem Cell, Feb. 2012, vol. 10 (2), pp. 218-229.
Dohner et al., "Diagnosis and Management of Ami in Adults: 2017 ELN Recommendations From an International Expert Panel," Blood, Jan. 2017, vol. 129 (4), pp. 424-447.
Duval et al., "Hematopoietic Stem-cell Transplantation for Acute Leukemia in Relapse or Primary Induction Failure," Journal of Clinical Oncology, Aug. 2010, vol. 28 (23), pp. 3730-3738.
Eppert et al., "Stem Cell Gene Expression Programs Influence Clinical Outcome in Human Leukemia," Nature Medicine, Aug. 2011, vol. 17 (9), pp. 1086-1093.
Francia et al., "Mouse Models of Advanced Spontaneous Metastasis for Experimental Therapeutics," Nature Reviews Cancer, Feb. 2011, vol. 11 (2), pp. 135-141.
Gollner et al., "Loss of the Histone Methyltransferase EZH2 Induces Resistance to Multiple Drugs in Acute Myeloid Leukemia," Nature Medicine, Jan. 2017, vol. 23 (1), pp. 69-78.
Kent et al, "BigWig and BigBed: Enabling Browsing of Large Distributed Datasets," Bioinformatics, Sep. 2010, vol. 26 (17), pp. 2204-2207.
Kumar., "Genetic Abnormalities and Challenges in the Treatment of Acute Myeloid Leukemia," Genes & Cancer, Feb. 2011, vol. 2 (2), pp. 95-107.
Langmead et al., "Fast Gapped-read Alignment With Bowtie 2 ," Nature Methods, Mar. 2012, vol. 9 (4), pp. 357-359.
Love et al., "Moderated Estimation of Fold Change and Dispersion for RNA-seq Data With DESeq2," Genome Biology, 2014, vol. 15 (12), pp. 550.
Marine et al., "Mdm2-mediated Ubiquitylation: p53 and Beyond," Cell Death and Differentiation, Jan. 2010, vol. 17 (1), pp. 93-102.

(Continued)

*Primary Examiner* — Sean E Aeder
(74) *Attorney, Agent, or Firm* — Graeme Boocock

(57) ABSTRACT

Herein are described methods of treating a human subject having acute myeloid leukemia (AML) that is refractory to induction therapy, wherein an MDM2 inhibitor is administered before or concurrently with chemotherapy, which may comprise induction therapy. Refractory AML may be predicted based on decreased expression of MTF2 in cells from a hematological sample obtained from the subject. Also provided are methods of predicting and treating AML responsive to MDM2/HDM2 inhibitors, based on MTF2 expression. One set of additional biomarkers useful in the predictions comprise one or more of H3K27me3, CD84, CD92, MDM2, NPM1, PRICKLE1, SET, ABCB6, POLQ, POLK, POLH, ARTIMIS, MCM6, CD327, CD90 and PARP1. Another set of additional biomarkers useful in the predictions include at least one of H3K27me3, MDM2, NPM1, SET, CD84 and PRICKLE1. Methods of selecting a patient for treatment with an MDM2 inhibitor before or concurrently with chemotherapy are also provided, along with kits and uses.

18 Claims, 58 Drawing Sheets
Specification includes a Sequence Listing.

(56) References Cited

PUBLICATIONS

Mateos-Gomez et al., "Mammalian Polymerase theta Promotes Alternative NHEJ and Suppresses Recombination," Nature, Feb. 2015, vol. 518 (7538), pp. 254-257.
McCormack et al., "Synergistic Induction of p53 Mediated Apoptosis by Valproic Acid and Nutlin-3 in Acute Myeloid Leukemia," Leukemia, May 2012, vol. 26 (5), pp. 910-917.
Merico et al., "Enrichment Map: A Network-based Method for Gene-set Enrichment Visualization and Interpretation," PLoS One, Nov. 2010, vol. 5 (11), pp. e13984.
Merico et al., "Visualizing Gene-set Enrichment Results Using the Cytoscape Plug-in Enrichment Map," Methods in Molecular Biology, 2011, vol. 781, pp. 257-277.
Olive et al., "The Comet Assay: a Method to Measure Dna Damage in Individual Cells," Nature Protocols, 2006, vol. 1(1), pp. 23-29.
Pabst et al., "Identification of Small Molecules That Support Human Leukemia Stem Cell Activity Ex Vivo," Nature Methods, Apr. 2014, vol. 11 (4), pp. 436-442.
Quinlan et al., "BEDTools: A Flexible Suite of Utilities for Comparing Genomic Features," Bioinformatics, Mar. 2010, vol. 26 (6), pp. 841-842.
Reimand et al., "g:Profiler—A Web Server for Functional Interpretation of Gene Lists (2011 Update)," Nucleic Acids Research, Jul. 2011, vol. 39, pp. W307-W315.
Reimand et al., "g:Profiler—A Web-based Toolset for Functional Profiling of Gene Lists From Large-scale Experiments," Nucleic Acids Research, Jul. 2007, vol. 35, pp. W193-W200.
Shen et al., "diffReps: Detecting Differential Chromatin Modification Sites From ChIP-seq Data With Biological Replicates," PLoS One, Jun. 2013, vol. 8 (6), pp. e65598.
Shih et al., "The Role of Mutations in Epigenetic Regulators in Myeloid Malignancies," Nature Reviews Cancer, Sep. 2012, vol. 12 (9), pp. 599-612.
Thol et al., "How I Treat Refractory and Early Relapsed Acute Myeloid Leukemia," Blood, Jul. 2015, vol. 126 (3), pp. 319-327.
Trapnell et al., "Differential Gene and Transcript Expression Analysis of RNA-seq Experiments With TopHat and Cufflinks," Nature Protocols, Mar. 2012, vol. 7, pp. 562-578.
Walker et al., "Polycomb-like 2 Associates With PRC2 and Regulates Transcriptional Networks During Mouse Embryonic Stem Cell Self-renewal and Differentiation," Cell Stem Cell, Feb. 2010, vol. 6 (2), pp. 153-166.
Wang et al., "SAR405838: An Optimized Inhibitor of MDM2-p53 Interaction That Induces Complete and Durable Tumor Regression," Cancer Research, Oct. 2014, vol. 74 (20), pp. 5855-5865.
Warner et al., "Identification of FDA-approved Drugs That Computationally Bind to MDM2," Chemical Biology & Drug Design, Oct. 2012, vol. 80 (4), pp. 631-637.
Wunderlich et al., "AML Cells Are Differentially Sensitive to Chemotherapy Treatment in a Human Xenograft Model," Blood, Mar. 2013, vol. 121 (12), pp. e90-e97.
Xie et al., "Mechanisms of Synergistic Antileukemic Interactions Between Valproic Acid and Cytarabine in Pediatric Acute Myeloid Leukemia," Clinical Cancer Research, Nov. 2010, vol. 16 (22), pp. 5499-5510.
Zuber et al., "Mouse Models of Human Aml Accurately Predict Chemotherapy Response," Genes & Development, Apr. 2009, vol. 23 (7), pp. 877-889.

* cited by examiner

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: MTF2 shRNA Clone 3 Coding Sequence

<400> SEQUENCE: 1
taatgtatgt cataagctc                                               19

<210> SEQ ID NO 2
<211> LENGTH: 19
<212> TYPE: DNA
<213> ORGANISM: Artificial Sequence
<220> FEATURE:
<223> OTHER INFORMATION: MTF2 shRNA Clone 7 Coding Sequence

<400> SEQUENCE: 2
ttggctttat gtccatcct                                               19

<210> SEQ ID NO 3
<211> LENGTH: 23
<212> TYPE: DNA
<213> ORGANISM: Artificial Sequence
<220> FEATURE:
<223> OTHER INFORMATION: Scrambled shRNA Coding Sequence

<400> SEQUENCE: 3
atatgttaca cgatatgtta tca                                          23
```

TREATMENT OF ACUTE MYELOID LEUKEMIA

CROSS-REFERENCE TO RELATED APPLICATION

This application claims priority to U.S. Provisional Patent Application No. 62/711,173, entitled 'TREATMENT OF ACUTE MYELOID LEUKEMIA' and filed on Jul. 27, 2018, the contents of which are hereby incorporated by reference.

FIELD

The present disclosure relates generally to treatment of leukemia. More particularly, the present disclosure relates to treatment of acute myeloid leukemia.

BACKGROUND

Although standard induction chemotherapy can induce remission in most patients with acute myeloid leukemia (AML), 30-40% of patients are unresponsive to this treatment. Unfortunately, as many as 60-90% of these refractory AML patients will not survive their disease regardless of the therapy[1-3].

There is a need for therapies to treat AML.

There is a need for means to prospectively identify refractory AML.

There is a need for means to prospectively identify AML responsive to treatment.

SUMMARY

It is an object of the present disclosure to obviate or mitigate at least one disadvantage of previous approaches.

In a first aspect, the present disclosure provides a method of treating a human subject having acute myeloid leukemia that is predicted to be refractory to standard induction therapy, comprising: administering to the subject an MDM2 inhibitor before or concurrently with standard chemotherapy.

In another aspect, there is provided a method of predicting response to induction therapy in a human subject having acute myeloid leukemia (AML), the method comprising: measuring levels of expression of analytes comprising MTF2 in a hematological sample obtained from the subject, measuring levels of expression of the analytes in a control sample, and determining whether or not the subject has AML refractory to induction therapy based on the measured levels of expression, wherein decreased expression of MTF2 in the sample relative to the control are predictive of AML refractory to induction therapy.

In another aspect, there is provided a method of selecting a patient for treatment with an MDM2 inhibitor before or concurrently with chemotherapy, the method comprising: carrying out the above-described method of predicting, and selecting the patient for treatment with an MDM2 inhibitor before or concurrently with chemotherapy if the patient is predicted to have AML refractory to induction therapy.

In another aspect, there is provided a method of treating a subject having refractory acute myeloid leukemia (AML), the method comprising: carrying out the above-described predictive method, and administering to the patient a treatment comprising an MDM2 inhibitor before or concurrently with chemotherapy if the patient is predicted to have AML refractory to induction therapy.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached figures.

DETAILED DESCRIPTION

Figure 1:
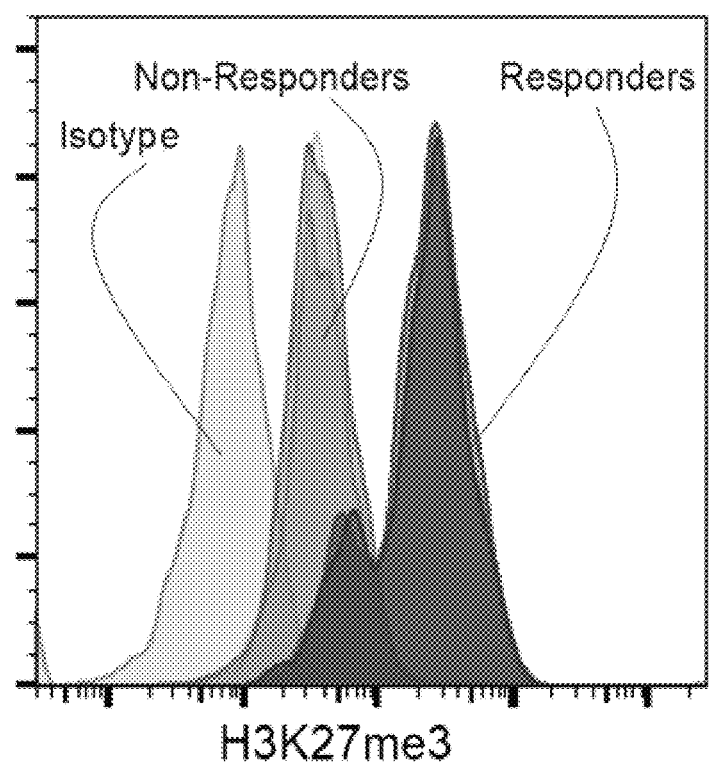
FIG. 1 depicts a representative flow cytometry histogram comparing Histone 3 Lysine 27 trimethylation (H3K27me3) levels within the $CD34^+CD38^-$ leukemic stem cell (LSC)-enriched population isolated from several AML patient bone marrow (BM) samples.

Generally, the present disclosure relates to methods of treating a human subject having acute myeloid leukemia (AML) that is predicted to be refractory to induction therapy, wherein an MDM2 inhibitor is administered before or concurrently with chemotherapy, which may comprise induction therapy. Refractory AML may be predicted based on decreased expression of MTF2 in a hematological sample obtained from the subject, relative to a control sample. AML responsive to treatment with an MDM2/HDM2 inhibitor may be identified based on expression of MTF2 or its downstream targets. Mouse double minute 2 homolog (MDM2), synonymously known as HDM2 (Human double minute 2 homolog) in the art, is a protein encoded by the MDM2 gene in humans. Biomarkers useful in the predictions include at least one of MTF2, H3K27me3, MDM2, NPM1, SET, CD84, CD92, ABCB6, MCM6, PARP1, POLQ, CD327, CD90 and PRICKLE1, wherein decreased trimethylation of H3K27 and expression of MTF2, and increased expression of MDM2, NPM1, SET, CD84, CD92, ABCB6, MCM6, PARP1, POLQ, CD327, CD90 or PRICKLE1 in the sample relative to the control is predictive of refractory AML.

Treatments Methods for AML Predicted to be Refractory

In one aspect, there is provided a method of treating a human subject having acute myeloid leukemia (AML) that is predicted to be refractory to induction therapy, comprising: administering to the subject an MDM2 inhibitor before or concurrently with chemotherapy.

By "AML refractory to induction therapy" (abbreviated herein as "refractory AML") is meant AML in which complete remission is not achieved following standard induction therapy.

By "predicted to be refractory" is meant that the subject is predetermined to have AML that will be refractory to induction therapy. For example, the prediction may be made at the time of diagnosis (initial presentation or relapse) or before a change in treatment. Accordingly, the subject in some embodiments will not have received induction therapy previously. In some embodiments, the patients will have previously received treatment but have either failed therapy or relapsed.

By "chemotherapy", in the context of AML, is meant any treatment with a therapeutic agent with curative intent, with therapeutic intent, and/or to reduce or mitigate symptoms.

In one embodiment, the chemotherapy comprises induction therapy.

By "induction therapy" for AML is meant a well-known treatment regimen aimed at inducing complete remission in an AML patient. Induction therapy is typically chemotherapy that aims to kill as many AML cells as possible. Induction often involves treatment with two chemotherapy drugs, such as cytarabine (ara-C) and an anthracycline drug. The anthracycline drug may be, e.g. daunorubicin (daunomycin) or idarubicin. Sometimes a third drug, cladribine (Leustatin, 2-CdA), is also given. Other induction therapy regimens include, but are not limited to, mitoxantrone and etoposide; mitoxantrone, etoposide and cytarabine; daunorubicin, cytarabine and etoposide; 6-thioguanine, cytarabine, and daunorubicin; or fludarabine or cladribine in combination with cytarabine, with or without filgrastim.

By "concurrently" is meant that the therapeutic effects of the MDM2 inhibitor and the chemotherapy or induction therapy at least partly overlap.

In one embodiment, the induction therapy comprises an anthracycline and cytarabine. In one embodiment, the anthracycline comprises daunorubicin.

In one embodiment, the step of administering comprises administering the MDM2 inhibitor concurrently with induction therapy.

By "complete remission" or "full remission" is meant that, after treatment, tests demonstrate that less than 5% blast cells are present in the bone marrow, and normal values for absolute neutrophil count (>1000/microL) and platelet count (>100,000/microL).

By "MDM2 inhibitor" is meant any molecule (biological or chemical) capable of reducing or abrogating HDM2/MDM2 activity. This activity may include the activity of HDM2/MDM2 as an E3 ubiquitin ligase, its activity in targeting p53 for degradation, and/or its activity in repressing p53 transcriptional activity. This inhibition may be by direct action of the inhibitor on HDM2/MDM2, or indirectly, e.g., by reducing or abrogating its transcription, translation, or stability. Molecules that upregulate HDM2/MDM2 inhibitors or negative effectors may also be indirect HDM2/MDM2 inhibitors.

In one embodiment, the MDM2 inhibitor comprises a small molecule inhibitor of MDM2.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), or Clofazimine.

In one embodiment, the MDM2 inhibitor comprises S-bepridil (Vascor).

In one embodiment, the MDM2 inhibitor comprises Protirelin (Thyrel TRH).

In one embodiment, the MDM2 inhibitor comprises Caramiphen (Oridine AT).

In one embodiment, the MDM2 inhibitor comprises Prenazone (Feprazone).

In one embodiment, the MDM2 inhibitor comprises Mephenoxalone.

In one embodiment, the MDM2 inhibitor comprises Azlocillin.

In one embodiment, the MDM2 inhibitor comprises Azaribine (Triazure).

In one embodiment, the MDM2 inhibitor comprises Clofazimine.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), Clofazimine, Nutlin, Nutlin3, Nutlin3a, Idasanutlin, MI-773, DS-3032(b), HDM201, BI 907828, or AMG 232.

In one embodiment, the MDM2 inhibitor comprises a Nutlin.

In one embodiment, the MDM2 inhibitor comprises Nutlin3 (IUPAC name: (±)-4-[4,5-Bis(4-chlorophenyl)-2-(2-isopropoxy-4-methoxy-phenyl)-4,5-dihydro-imidazole-1-carbonyl]-piperazin-2-one).

In one embodiment, the MDM2 inhibitor comprises Nutlin3a (IUPAC name: 4-[(4S,5R)-4,5-bis(4-chlorophenyl)-2-(4-methoxy-2-propan-2-yloxyphenyl)-4,5-dihydroimidazole-1-carbonyl]piperazin-2-one), which is also referred to herein as "Nutlin3A".

In one embodiment, the MDM2 inhibitor comprises Idasanutlin (IUPAC name: 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid).

In one embodiment, the MDM2 inhibitor comprises MI-773 (IUPAC name: (2'R,3S,3'S,5'R)-6-chloro-3'-(3-chloro-2-fluorophenyl)-5'-(2,2-dimethylpropyl)-N-(4-hydroxycyclohexyl)-2-oxospiro[1H-indole-3,4'-pyrrolidine]-2'-carboxamide).

In one embodiment, the MDM2 inhibitor comprises DS-3032(b) (Daiichi Sankyo), a dihydroimidazothiazole.

In one embodiment, the MDM2 inhibitor comprises HDM201 (Novartis). HDM201 is described in WO2017060431 or WO2014020502.

In one embodiment, the MDM2 inhibitor comprises AMG 232 (Amgen) (IUPAC name: 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid). It is to be understood that AMG 232 is equivalent to KRT 232, and that the former term is intended to encompass the latter, and vice versa.

In one embodiment, the MDM2 inhibitor comprises S-bepridil (IUPAC name: N-benzyl-N-(3-isobutoxy-2-pyrrolidin-1-yl-propyl)aniline).

In one embodiment, the MDM2 inhibitor comprises Protirelin (IUPAC name: (2S)-N-[(2S)-1-[(2S)-2-carbamoylpyrrolidin-1-yl]-3-(1H-imidazol-5-yl)-1-oxopropan-2-yl]-5-oxopyrrolidine-2-carboxamide).

In one embodiment, the MDM2 inhibitor comprises Caramiphen (IUPAC name: 2-(diethylamino)ethyl 1-phenylcyclopentane-1-carboxylate).

In one embodiment, the MDM2 inhibitor comprises Prenazone (IUPAC name: 4-(3-methylbut-2-enyl)-1,2-diphenylpyrazolidine-3,5-dione).

In one embodiment, the MDM2 inhibitor comprises Mephenoxalone (IUPAC name: 5-[(2-methoxyphenoxy)methyl]-1,3-oxazolidin-2-one).

In one embodiment, the MDM2 inhibitor comprises Azlocillin (IUPAC name: (2S,5R,6R)-3,3-dimethyl-7-oxo-6-[[(2R)-2-[(2-oxoimidazolidine-1-carbonyl)amino]-2-phenylacetyl]amino]-4-thia-1-azabicyclo[3.2.0]heptane-2-carboxylic acid).

In one embodiment, the MDM2 inhibitor comprises Azaribine (IUPAC name: [(2R,3R,4R,5R)-3,4-diacetyloxy-5-(3,5-dioxo-1,2,4-triazin-2-yl)oxolan-2-yl]methyl acetate).

In one embodiment, the MDM2 inhibitor comprises Clofazimine (IUPAC name: N,5-bis(4-chlorophenyl)-3-propan-2-yliminophenazin-2-amine).

In one embodiment, the MDM2 inhibitor comprises a biologic.

By 'biologic' is meant a molecule manufactured in, extracted from, or semi-synthesized from one or more biological sources. In one embodiment, the biologic is a peptide. The peptide may be a blocking peptide for MDM2. In one embodiment, the biological may be an antibody.

In one embodiment, the biologic comprises ALRN-6924 (Aileron). ALRN-6924 is described in Canadian Patent Application No. 2,961,029.

In one embodiment, the MDM2 inhibitor comprises an aptamer.

By 'aptamer' is meant an oligonucleotide or peptide molecule that binds to a specific target molecule. In one embodiment, the aptamer is an oligonucleotide that binds to MDM2. In one embodiment, the aptamer is a peptide that binds to MDM2.

In one embodiment the MDM2 inhibitor comprises a combination of one or more of the inhibitors described herein.

In one embodiment, the AML is predicted to be refractory to induction therapy based on decreased expression of MTF2 in a hematological sample obtained from the subject, relative to a control sample.

By "hematological sample" is meant any sample obtained from a subject that comprises cells of a hematological lineage. For example, a hematological sample may comprise peripheral blood, or a sample derived therefrom. A hematological sample may also comprise bone marrow aspirate, or a sample derived therefrom. A hematological sample may also comprise hematological cells isolated, fractionated, or sorted from a collected sample. "Hematological cells" will be understood to encompass cells of myeloid and lymphoid lineages and their progenitors. In some embodiments, hematological samples comprising or consisting of nucleated cells of particular selected lineages may be preferred.

In one embodiment, the hematological sample comprises or is obtained from bone marrow aspirate.

In one embodiment, the hematological sample comprises or is obtained from peripheral blood.

In one embodiment, the cells comprise hematopoietic stem and progenitor cells (HSPCs).

In one embodiment, the cells are obtained by flow cytometry or magnetic-activated cell sorting.

In one embodiment, the cells comprise hematopoietic lineage-negative (Lin$^-$) cells. In one embodiment, the cells comprise CD34$^+$ cells. In one embodiment, the cells comprise CD34$^+$CD38$^-$ cells. In one embodiment, the cells comprise CD34$^+$CD38$^-$Lin$^-$ cells. In one embodiment, the cells comprise AC133$^+$ cells. In one embodiment, the cells comprise AC133$^+$ CD38$^-$ cells. Combinations of these cell surface features are envisaged in other embodiments. In other embodiments, the cells may consist of any one of the aforementioned populations, including any one of the possible combinations.

As used herein, a "control sample" will be understood to be a sample that provides a measurement indicative of non-refractory AML for the analyte in question. The control sample may comprise non-refractory AML cells. The control sample may comprise healthy hematological cells. The control sample may be from normal cells. By "normal" is meant healthy, non-leukemic cells. For example, the control sample may be from healthy blood or bone marrow. Depending on requirements, then, the control sample may be obtained from a healthy individual or an individual having non-refractory AML. A control sample may also be a sample from individual with AML from a time point at which the patient did not have AML. A control sample may also be a supplied reference sample designed to provide a control measurement of a fixed amount of analyte, e.g. an amount indicative of non-refractory AML. Where analyte quantification is based on absolute or approximate counts, the requirements of a control sample could be fulfilled by a reference threshold value. The measurements taken for the analytes may be compared to measurements taken from a single control sample. Alternatively, the measurements may be compared to measurements taken from multiple control samples.

In one embodiment, the control sample is from non-refractory AML cells.

In one embodiment, the control sample is from healthy hematological cells. For example, the control sample may be from healthy bone marrow.

In other embodiments, measurements of additional analytes or combinations of analytes may be predictive of AML refractory to induction therapy. Where gene names are indicated herein, it will be understood that these could encompass RNA transcripts (or splice variants or fragments thereof), corresponding cDNAs, or proteins (or fragments thereof) depending on the assay and on requirements. Where methylation status is mentioned (e.g. for H3K27me3) it will be readily understood that the protein capable of the modification is intended (e.g. H3).

In one embodiment, the AML is additionally predicted to be refractory to induction therapy based on: decreased trimethylation of H3K27 in the cells from the subject relative to the control sample.

In one embodiment, the AML is additionally predicted to be refractory to induction therapy based on: increased expression of one or more of CD84 and CD92 in the cells from the subject relative to the control sample.

In one embodiment, the AML is additionally predicted to be refractory to induction therapy based on: increased expression of MDM2 in the cells from the subject relative to the control sample.

In one embodiment, the AML is additionally predicted to be refractory to induction therapy based on: increased expression of one or more of: NPM1, PRICKLE1, SET, and ABCB6 in the cells from the subject relative to the control sample.

In one embodiment, the AML is additionally predicted to be refractory to induction therapy based on: increased expression of one or more of: CD327, and CD90 in the cells from the subject relative to the control sample.

In one embodiment, the AML is additionally predicted to be refractory to induction therapy based on: increased expression of POLQ in the cells from the subject relative to the control sample.

In one embodiment, the AML is additionally predicted to be refractory to induction therapy based on: increased expression one or more of: POLK, POLH, ARTEMIS, MCM6, and PARP1 in the cells from the subject relative to the control sample.

In one embodiment, the AML is predicted to be refractory to induction therapy based on:
  decreased trimethylation of H3K27,
  increased expression of CD84 and CD92,
  increased expression of MDM2,
  increased expression of NPM1, PRICKLE1, SET, and ABCB6,
  increased expression of POLQ, and
  increased expression of POLK, POLH, ARTEMIS, MCM6, and PARP1
  in the cells from the subject relative to the control sample.

In one embodiment, the AML is predicted to be refractory to induction therapy based on: decreased expression of MTF2; and one or more of: decreased H3K27me3, increased expression of MDM2, increased expression of NPM1, increased expression of SET, increased expression of CD84, increased expression of CD92 and increased expression of PRICKLE1 in a hematological sample obtained from the subject, relative to a control sample.

In one embodiment, the AML is predicted to be refractory to induction therapy based on: decreased expression of MTF2, decreased H3K27me3, increased expression of MDM2, increased expression of NPM1, increased expression of SET, increased expression of CD84 and increased expression of PRICKLE1 in a hematological sample obtained from the subject, relative to a control sample.

In one embodiment, the AML is predicted to be refractory to induction therapy based on: decreased expression of MTF2; and one or more of: increased expression of MDM2, increased expression of NPM1, increased expression of SET, increased expression of CD84 and increased expression of PRICKLE1 in a hematological sample obtained from the subject, relative to a control sample.

In one embodiment, the AML is predicted to be refractory to induction therapy based on: decreased expression of MTF2, increased expression of MDM2, increased expression of NPM1, increased expression of SET, increased expression of CD84 and increased expression of PRICKLE1 in a hematological sample obtained from the subject, relative to a control sample.

In one embodiment, the AML is predicted to be refractory to induction therapy based on: decreased expression of MTF2; and one or more of: increased expression of NPM1, increased expression of SET, increased expression of CD84 and increased expression of PRICKLE1 in cells obtained from the subject, relative to a control sample.

In one embodiment, the AML is predicted to be refractory to induction therapy based on: decreased expression of MTF2, increased expression of NPM1, increased expression of SET, increased expression of CD84 and increased expression of PRICKLE1 in a hematological sample obtained from the subject, relative to a control sample.

In one embodiment, the "expression" of the above-noted analyte or analytes will be understood to mean relative expression of the analyte or analytes. For instance, the relative expression of an analyte may be determined based the expression level of that analyte as compared to an internal reference.

By "internal reference" is meant an analyte, the amount of which is expected to be generally constant across samples, such as between non-refractory vs. refractory AML samples, or between healthy samples and refractory AML samples depending on assay requirements. So-called 'housekeeping genes' are one potential source of internal in references. The internal reference may be CD45. The internal reference may be Histone H3. The internal reference may be a pre-determined threshold based on established and known relative expression levels.

For quality assurance (QA) or quality control (QC) purposes, it is also possible in some embodiments for sample to be spiked with a fixed amount a QA/QC analyte.

In one embodiment, the expression is protein expression.

In one embodiment, the expression is RNA expression.

Medical Uses in AML Predicted to be Refractory

In one aspect, there is provided a use of an MDM2 inhibitor for treatment of a human subject having acute myeloid leukemia (AML), wherein the AML is predicted to be refractory to induction therapy.

In one aspect, there is provided a use of an MDM2 inhibitor for preparation of a medicament for treatment of a human subject having acute myeloid leukemia (AML), wherein the AML is predicted to be refractory to induction therapy.

In one aspect, there is provided an MDM2 inhibitor for use in treatment of a human subject having acute myeloid leukemia (AML), wherein the AML is predicted to be refractory to induction therapy.

In the above uses, the MDM2 may be for use before or concurrent with chemotherapy.

In one embodiment, the chemotherapy comprises induction therapy.

In one embodiment, the induction therapy comprises an anthracycline and cytarabine.

In one embodiment, the anthracycline comprises daunorubicin.

In one embodiment, the MDM2 inhibitor comprises a small molecule inhibitor of MDM2.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), or Clofazimine.

In one embodiment, the MDM2 inhibitor comprises S-bepridil (Vascor).

In one embodiment, the MDM2 inhibitor comprises Protirelin (Thyrel TRH).

In one embodiment, the MDM2 inhibitor comprises Caramiphen (Oridine AT).

In one embodiment, the MDM2 inhibitor comprises Prenazone (Feprazone).

In one embodiment, the MDM2 inhibitor comprises Mephenoxalone.

In one embodiment, the MDM2 inhibitor comprises Azlocillin.

In one embodiment, the MDM2 inhibitor comprises Azaribine (Triazure).

In one embodiment, the MDM2 inhibitor comprises Clofazimine.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), Clofazimine, Nutlin, Nutlin3, Nutlin3a, Idasanutlin, MI-773, DS-3032(b), HDM201, BI 907828 or AMG 232.

In one embodiment, the MDM2 inhibitor comprises a Nutlin.

In one embodiment, the MDM2 inhibitor comprises Nutlin3.

In one embodiment, the MDM2 inhibitor comprises Nutlin3a.

In one embodiment, the MDM2 inhibitor comprises Idasanutlin.

In one embodiment, the MDM2 inhibitor comprises MI-773.

In one embodiment, the MDM2 inhibitor comprises DS-3032(b) (Daiichi Sankyo).

In one embodiment, the MDM2 inhibitor comprises HDM201 (Novartis).

In one embodiment, the MDM2 inhibitor comprises AMG 232 (Amgen).

In one embodiment, the MDM2 inhibitor comprises BI 907828 (Boehringer Ingelheim).

In one embodiment, the MDM2 inhibitor comprises a biologic. In one embodiment, the biologic comprises ALRN-6924 (Aileron). In one embodiment, the biologic is a peptide. The peptide may be a blocking peptide for MDM2. In one embodiment, the biological may be an antibody. The antibody may be a blocking antibody for MDM2.

In one embodiment, the MDM2 inhibitor comprises an aptamer. In one embodiment, the aptamer is an oligonucleotide that binds to MDM2. In one embodiment, the aptamer is a peptide that binds to MDM2.

In one embodiment the MDM2 inhibitor comprises a combination of one or more of the inhibitors described herein.

In one embodiment, the induction therapy comprises an anthracycline and cytarabine. In one embodiment, the anthracycline comprises daunorubicin. Other induction therapy regiments are described above, and are envisaged for other embodiments.

In one embodiment, the AML is predicted to be refractory to induction therapy based on decreased expression of MTF2 in cells from a hematological sample obtained from the subject, relative to a control sample.

In one embodiment, the hematological sample comprises or is obtained from bone marrow aspirate.

In one embodiment, the hematological sample comprises or is obtained from peripheral blood.

In one embodiment, the cells comprise hematopoietic stem and progenitor cells (HSPCs).

In one embodiment, the cells are obtained by flow cytometry.

In one embodiment, the cells comprise hematopoietic lineage-negative (Lin$^-$) cells. In one embodiment, the cells comprise CD34$^+$ cells. In one embodiment, the cells comprise Lin$^-$CD34$^+$ cells. In one embodiment, the cells comprise CD34$^+$CD38$^-$ cells. In one embodiment, the cells comprise CD34$^+$CD38$^-$Lin$^-$ cells. In one embodiment, the cells comprise AC133$^+$ cells. In one embodiment, the cells comprise Lin$^-$AC133$^+$ cells. In one embodiment, the cells comprise AC133$^+$CD38$^-$ cells. In one embodiment, the cells comprise AC133$^+$CD34$^+$CD38$^-$ cells Combinations of these cell surface features are envisaged in other embodiments. In other embodiments, the cells may consist of any one of the aforementioned populations, including any one of the possible combinations.

In one embodiment, the control sample is from non-refractory AML cells.

In one embodiment, the control sample is from health hematological cells. For example, the control sample may be from healthy bone marrow.

In other embodiments, measurements of additional analytes or combinations of analytes may be predictive of AML refractory to induction therapy. Where gene names are indicated herein, it will be understood that these could encompass RNA transcripts (or splice variants or fragments thereof), corresponding cDNAs, or proteins (or fragments thereof) depending on the assay and on requirements. Where methylation status is mentioned (e.g. for H3K27me3) it will be readily understood that the protein capable of the modification is intended (e.g. Histone 3).

In one embodiment, the AML is additionally predicted to be refractory to induction therapy based on: decreased trimethylation of H3K27 in the cells from the subject relative to the control sample.

In one embodiment, the AML is additionally predicted to be refractory to induction therapy based on: decreased trimethylation of H3K27 in the cells from the subject relative to a predetermined threshold.

In one embodiment, the AML is additionally predicted to be refractory to induction therapy based on: increased expression of one or more of CD84 and CD92 in the cells from the subject relative to the control sample.

In one embodiment, the AML is additionally predicted to be refractory to induction therapy based on: increased expression of one or more of CD84 and CD92 in the cells from the subject relative to a predetermined threshold.

In one embodiment, the AML is additionally predicted to be refractory to induction therapy based on: increased expression of MDM2 in the cells from the subject relative to the control sample in the cells from the subject relative to the control sample.

In one embodiment, the AML is additionally predicted to be refractory to induction therapy based on: increased expression of MDM2 in the cells from the subject relative to the control sample in the cells from the subject relative to a predetermined threshold.

In one embodiment, the AML is additionally predicted to be refractory to induction therapy based on: increased expression of one or more of: NPM1, PRICKLE1, SET, and ABCB6 in the cells from the subject relative to the control sample.

In one embodiment, the AML is additionally predicted to be refractory to induction therapy based on: increased expression of one or more of: NPM1, PRICKLE1, SET, and ABCB6 in the cells from the subject relative to a predetermined threshold.

In one embodiment, the AML is additionally predicted to be refractory to induction therapy based on: increased expression of POLQ in the cells from the subject relative to the control sample in the cells from the subject relative to the control sample.

In one embodiment, the AML is additionally predicted to be refractory to induction therapy based on: increased expression of POLQ in the cells from the subject relative to the control sample in the cells from the subject relative to a predetermined threshold.

In one embodiment, the AML is additionally predicted to be refractory to induction therapy based on: increased expression one or more of: POLK, POLH, ARTEMIS, MCM6, and PARP1 in the cells from the subject relative to the control sample.

In one embodiment, the AML is additionally predicted to be refractory to induction therapy based on: increased expression one or more of: CM6, and PARP1 in the cells from the subject relative to a predetermined threshold.

In one embodiment, the AML is predicted to be refractory to induction therapy based on:
decreased trimethylation of H3K27,
increased expression of CD84 and CD92,
increased expression of MDM2,
increased expression of NPM1, PRICKLE1, SET, and ABCB6,
increased expression of POLQ, and
increased expression of POLK, POLH, ARTEMIS, MCM6, and PARP1 in the cells from the subject relative to the control sample.

In one embodiment, the AML is predicted to be refractory to induction therapy based on: decreased expression of MTF2; and one or more of: decreased trimethylation of H3K27, increased expression of MDM2, increased expression of NPM1, increased expression of SET, increased expression of CD84 and increased expression of PRICKLE1 in cells from a hematological sample obtained from the subject, relative to a control sample.

In one embodiment, the AML is predicted to be refractory to induction therapy based on: decreased expression of MTF2, decreased trimethylation of H3K27, increased expression of MDM2, increased expression of NPM1, increased expression of SET, increased expression of CD84 and increased expression of PRICKLE1 in cells from a hematological sample obtained from the subject, relative to a control sample.

In one embodiment, the AML is predicted to be refractory to induction therapy based on: decreased expression of MTF2; and one or more of: increased expression of MDM2, increased expression of NPM1, increased expression of SET, increased expression of CD84 and increased expression of PRICKLE1 in cells from a hematological sample obtained from the subject, relative to a control sample.

In one embodiment, the AML is predicted to be refractory to induction therapy based on: decreased expression of MTF2, increased expression of MDM2, increased expression of NPM1, increased expression of SET, increased expression of CD84 and increased expression of PRICKLE1 in cells from a hematological sample obtained from the subject, relative to a control sample.

In one embodiment, the AML is predicted to be refractory to induction therapy based on: decreased expression of MTF2; and one or more of: increased expression of NPM1, increased expression of SET, increased expression of CD84 and increased expression of PRICKLE1 in cells from a hematological sample obtained from the subject, relative to a control sample.

In one embodiment, the AML is predicted to be refractory to induction therapy based on: decreased expression of MTF2, increased expression of NPM1, increased expression of SET increased expression of CD84 and increased expression of PRICKLE1 in cells from a hematological sample obtained from the subject, relative to a control sample.

In one embodiment, the "expression" of the above-noted analyte or analytes will be understood to mean relative expression of the analyte or analytes. For instance, the relative expression of an analyte may be determined based the expression level of that analyte as compared to an internal reference.

In one embodiment, the expression is protein expression.
In one embodiment, the expression is RNA expression.

Predicting Refractory AML

In one aspect, there is provided a method of predicting response to chemotherapy for a human subject having acute myeloid leukemia (AML), the method comprising: measuring levels of expression of one or more analytes comprising MTF2 in a hematological sample obtained from the subject, measuring levels of expression of the one or more analytes in a control sample, and determining whether or not the subject has AML refractory to induction therapy based on the measured levels of expression, wherein decreased expression of MTF2 in the sample relative to the control is predictive of AML refractory to chemotherapy.

In another aspect, there is provided a method of predicting response to chemotherapy for a human subject having acute myeloid leukemia (AML), the method comprising: measuring levels of expression of one or more analyte comprising CD92 in a hematological sample obtained from the subject, measuring levels of expression of the one or more analyte in a control sample, and determining whether not the subject has AML refractory to induction therapy based on the measured levels of expression, wherein increased expression of CD92 in the subject sample relative to the control sample is predictive of AML refractory to chemotherapy.

By "analyte" is meant a biological molecule that may be measured or detected, and whose measurement or detection is indicative or predictive of a biological trait, which in this case is refractory AML. An analyte may be a protein, an RNA, a cDNA, a fragment thereof, a splice variant thereof (in the case of RNA or cDNA), or a post-translational modification thereof (in the case of a protein).

In one embodiment, the chemotherapy comprises induction therapy. The induction therapy may be any one of the induction therapies described above.

In one embodiment, the analytes further comprise H3K27, wherein decreased trimethylation of H3K27 in the sample relative to the control is predictive of AML refractory to chemotherapy.

In one embodiment, the analytes further comprise CD92, wherein increased expression is predictive of AML refractory to chemotherapy.

In one embodiment, the analytes further comprise CD84, wherein increased expression is predictive of AML refractory to chemotherapy.

In one embodiment, the analytes further comprise one or more of CD84 and CD92, wherein increased expression is predictive of AML refractory to chemotherapy.

In one embodiment, the analytes further comprise MDM2, wherein increased expression is predictive of AML refractory to chemotherapy.

In one embodiment, the analytes further comprise one or more of: NPM1, PRICKLE1, SET, and ABCB6, wherein increased expression is predictive of AML refractory to chemotherapy.

In one embodiment, the analytes further comprise POLQ, wherein increased expression is predictive of AML refractory to chemotherapy.

In one embodiment, the analytes further comprise one or more of POLK, POLH, ARTEMIS, MCM6, and PARP1, wherein increased expression is predictive of AML refractory to chemotherapy.

In one embodiment, the analytes further comprise one or more of: CD327, and CD90, wherein increased expression is predictive of AML refractory to chemotherapy.

In one embodiment, the analytes further comprise one or more of POLK, POLH and ARTEMIS, wherein increased expression is predictive of AML refractory to chemotherapy.

In one embodiment, the analytes further comprise H3K27, CD84 and CD92, MDM2, NPM1, PRICKLE1, SET, ABCB6, POLQ, POLK, POLH, ARTEMIS, MCM6, and PARP1, wherein:
 decreased trimethylation of H3K27, and
 increased expression of CD84, CD92, MDM2, NPM1, PRICKLE1, SET, and ABCB6, POLQ, POLK, POLH, ARTEMIS, MCM6, and PARP1
 in the cells from the subject relative to the control sample is predictive of AML refractory to chemotherapy.

In one embodiment, the analytes further comprise H3K27, CD84 and CD92, MDM2, NPM1, PRICKLE1, SET, ABCB6, POLQ, POLK, POLH, ARTEMIS, MCM6, and PARP1, wherein:
 decreased trimethylation of H3K27, and
 increased expression of CD84, CD92, MDM2, NPM1, PRICKLE1, SET, and ABCB6, POLQ, POLK, POLH, ARTEMIS, MCM6, and PARP1
 in the cells from the subject relative to the predetermined threshold is predictive of AML refractory to chemotherapy.

In one embodiment, the AML is predicted to be refractory to induction therapy based on decreased expression of MTF2 in cells from a hematological sample obtained from the subject, relative to a predetermined threshold.

In one embodiment, the AML is predicted to be refractory to induction therapy based on increased expression of CD92 in cells from a hematological sample obtained from the subject, relative to a control sample.

In one embodiment, the AML is predicted to be refractory to induction therapy based on increased expression of CD92 in cells from a hematological sample obtained from the subject, relative to a predetermined threshold.

In one embodiment, the AML is further predicted to be refractory to induction therapy based on: decreased expression of MTF2 in the cells from the subject relative to a predetermined threshold.

In one embodiment, the AML is further predicted to be refractory to induction therapy additionally based on: increased expression of: CD84 in the cells from the subject relative to a predetermined threshold.

In one embodiment, the AML is predicted to be refractory to induction therapy based on: increased expression one or more of: MCM6, and PARP1, in the cells from the subject relative to a predetermined threshold.

In one embodiment, the AML is predicted to be refractory to induction therapy based on: increased expression of CD92 and one or more of: increased expression of MDM2, increased expression of NPM1, increased expression of SET, increased expression of CD84, decreased expression of MTF2, and increased expression of PRICKLE1 in cells from a hematological sample obtained from the subject, relative to a control sample.

In one embodiment, the AML is predicted to be refractory to induction therapy based on: increased expression of CD92 and one or more of: increased expression of NPM1, increased expression of SET, increased expression of CD84, decreased expression of MTF2, and increased expression of PRICKLE1 in cells from a hematological sample obtained from the subject, relative to a control sample.

In one embodiment, the AML is predicted to be refractory to induction therapy based on: increased expression of CD92 and one or more of: increased expression of MDM2, increased expression of NPM1, increased expression of SET, increased expression of CD84, decreased expression of MTF2, and increased expression of PRICKLE1 in cells from a hematological sample obtained from the subject, relative to a predetermined threshold.

In one embodiment, the AML is additionally predicted to be refractory to induction therapy based on: increased expression of CD92 and one or more of: increased expression of NPM1, increased expression of SET, increased expression of CD84, decreased expression of MTF2, and increased expression of PRICKLE1 in cells from a hematological sample obtained from the subject, relative to a predetermined threshold.

In one embodiment, the analytes further comprise at least one of H3K27me3, MDM2, NPM1, SET, CD84, CD92 and PRICKLE1, wherein decreased expression of MTF2, decreased trimethylation of H3K27, and increased expression of MDM2, NPM1, SET, CD84, CD92 or PRICKLE1 in the sample relative to the control is predictive of AML refractory to induction therapy.

In one embodiment, the analytes comprise MTF2, H3K27me3, MDM2, NPM1, SET, CD84, CD92 and PRICKLE1.

In one embodiment, the analytes consist of MTF2, H3K27me3, MDM2, NPM1, SET, CD84, CD92 and PRICKLE1.

In one embodiment, the analytes comprise MTF2, MDM2, NPM1, SET, CD84, CD92 and PRICKLE1.

In one embodiment, the analytes consist of MTF2, MDM2, NPM1, SET, CD84, CD92 and PRICKLE1.

In one embodiment, the analytes comprise MTF2, NPM1, SET, CD84, CD92 and PRICKLE1.

In one embodiment, the analytes consist of MTF2, NPM1, SET, CD84, CD92 and PRICKLE1.

In one embodiment, the hematological sample comprises or is obtained from bone marrow aspirate.

In one embodiment, the hematological sample comprises or is obtained from peripheral blood.

In one embodiment, the cells comprise hematopoietic stem and progenitor cells (HSPCs).

In one embodiment, the method further comprises obtaining the cells flow cytometry or magnetic-activated cell sorting.

In one embodiment, the cells comprise hematopoietic lineage-negative (Lin$^-$) cells. In one embodiment, the cells comprise CD34$^+$ cells. In one embodiment, the cells comprise Lin$^-$CD34$^+$ cells. In one embodiment, the cells comprise CD34$^+$CD38$^-$ cells. In one embodiment, the cells comprise CD34$^+$CD38$^-$Lin$^-$ cells. In one embodiment, the cells comprise AC133$^+$ cells. In one embodiment, the cells comprise Lin$^-$AC133$^+$ cells. In one embodiment, the cells comprise AC133$^+$CD38$^-$ cells. In one embodiment, the cells comprise AC133+CD34$^+$CD38$^-$ cells Combinations of these cell surface features are envisaged in other embodiments. In other embodiments, the cells may consist of any one of the aforementioned populations, including any one of the possible combinations.

In one embodiment, the "expression" of the above-noted analyte or analytes will be understood to mean relative expression of the analyte or analytes. For instance, the relative expression of an analyte may be determined based the expression level of that analyte as compared to an internal reference.

In one embodiment, the analytes are proteins. In one embodiment, the levels of protein expression are determined as a ratio of protein expression to expression of an internal reference protein. In one embodiment, the internal reference protein is CD45 or Histone H3. In one embodiment, the levels of protein expression are an absolute value or within a range of absolute values using any relevant means of measurement or units, and can be compared with a predetermined known threshold.

In one embodiment, the analytes are RNA. In one embodiment, the steps of measuring are carried out by RT-qPCR or transcript counting.

In one embodiment, the control sample is from non-refractory AML cells.

In one embodiment, the control sample is from normal (non-AML) cells. For example, the control sample may be from healthy bone marrow.

Predicting Response to an MDM2 Inhibitor in AML

In one aspect, there is provided a method of predicting response to treatment with an MDM2 inhibitor for a human subject having acute myeloid leukemia (AML), the method comprising: measuring levels of expression of one or more analytes comprising MTF2 in a hematological sample obtained from the subject, measuring levels of expression of the one or more analytes in a control sample, and determining whether or not the subject has AML responsive to the MDM2 inhibitor based on the measured levels of expression, wherein decreased expression of MTF2 in the sample relative to the control is predictive of AML responsive to the MDM2 inhibitor.

In one embodiment, the decreased expression of MTF2 in the sample relative to the control is predictive of AML responsive to the MDM2 inhibitor and chemotherapy. In one embodiment, the chemotherapy comprises induction therapy. In other embodiments, the induction therapy is any of the above-described regimens.

In one embodiment, the AML has not previously been treated.

In one embodiment, the AML has been previously treated.

In one embodiment, the AML has relapsed.

In one embodiment, the AML has relapsed following chemotherapy.

In one embodiment, the AML has relapsed following induction therapy.

In one embodiment, the AML has not responded following chemotherapy.

In one embodiment the AML has not responded following induction therapy.

In one embodiment, the relapsed AML is predicted by measuring levels of expression of one or more of POLH, POLK, and ARTEMIS.

In one embodiment, the analytes further comprise H3K27, wherein decreased trimethylation of H3K27 in the sample relative to the control is predictive of AML responsive to the MDM2 inhibitor.

In one embodiment, the analytes further comprise one or more of CD84 and CD92, wherein increased expression is predictive of AML responsive to the MDM2 inhibitor.

In one embodiment, the analytes further comprise MDM2, wherein increased expression is predictive of AML responsive to the MDM2 inhibitor.

In one embodiment, the analytes further comprise one or more of: NPM1, PRICKLE1, SET, and ABCB6, wherein increased expression is predictive of AML responsive to the MDM2 inhibitor.

In one embodiment, the analytes further comprise POLQ, wherein increased expression is predictive of AML responsive to the MDM2 inhibitor.

In one embodiment, the analytes further comprise one or more of POLK, POLH, ARTEMIS, MCM6, and PARP1, wherein increased expression is predictive of AML responsive to the MDM2 inhibitor.

In one embodiment, the analytes further comprise H3K27, CD84 and CD92, MDM2, NPM1, PRICKLE1, SET, ABCB6, POLQ, POLK, POLH, ARTEMIS, MCM6, and PARP1, wherein:
  decreased trimethylation of H3K27, and
  increased expression of CD84, CD92, MDM2, NPM1, PRICKLE1, SET, and ABCB6, POLQ, POLK, POLH, ARTEMIS, MCM6, and PARP1
in the cells from the subject relative to the control sample is predictive of AML responsive to the MDM2 inhibitor.

In one embodiment, the analytes further comprise at least one of H3K27me3, MDM2, NPM1, SET, CD84 and PRICKLE1, wherein decreased expression of MTF2, decreased trimethylation of H3K27me3, and increased expression of MDM2, NPM1, SET, CD84 or PRICKLE1 in the sample relative to the control is predictive of AML responsive to the MDM2 inhibitor.

In one embodiment, the analytes comprise MTF2, H3K27me3, MDM2, NPM1, SET, CD84, CD92 and PRICKLE1.

In one embodiment, the analytes consist of MTF2, H3K27me3, MDM2, NPM1, SET, CD84 and PRICKLE1.

In one embodiment, the analytes comprise MTF2, MDM2, NPM1, SET, CD84 and PRICKLE1.

In one embodiment, the analytes consist of MTF2, MDM2, NPM1, SET, CD84 and PRICKLE1.

In one embodiment, the analytes comprise MTF2, NPM1, SET, CD84 and PRICKLE1.

In one embodiment, the analytes consist of MTF2, NPM1, SET, CD84 and PRICKLE1.

In one embodiment, the AML has relapsed following induction therapy, and the analytes comprise one or more of POLK, POLH, and ARTEMIS.

In one embodiment, the hematological sample comprises or is obtained from bone marrow aspirate.

In one embodiment, the hematological sample comprises or is obtained from peripheral blood.

In one embodiment, the cells comprise hematopoietic stem and progenitor cells (HSPCs).

In one embodiment, the method further comprises obtaining the cells flow cytometry.

In one embodiment, the cells comprise hematopoietic lineage-negative (Lin$^-$) cells. In one embodiment, the cells comprise CD34$^+$ cells. In one embodiment, the cells comprise Lin$^-$CD34$^+$ cells. In one embodiment, the cells comprise CD34$^+$CD38$^-$ cells. In one embodiment, the cells comprise CD34$^+$CD38$^-$Lin$^-$ cells. In one embodiment, the cells comprise AC133$^+$ cells. In one embodiment, the cells comprise Lin$^-$AC133$^+$ cells. In one embodiment, the cells comprise AC133$^+$CD38$^-$ cells. In one embodiment, the cells comprise AC133$^+$CD34$^+$CD38$^-$ cells. Combinations of these cell surface features are envisaged in other embodiments. In other embodiments, the cells may consist of any one of the aforementioned populations, including any one of the possible combinations.

In one embodiment, the "expression" of the above-noted analyte or analytes will be understood to mean relative expression of the analyte or analytes. For instance, the relative expression of an analyte may be determined based the expression level of that analyte as compared to an internal reference.

In one embodiment, the analytes are proteins. In one embodiment, the levels of protein expression are determined as a ratio of protein expression to expression of an internal reference protein. In one embodiment, the internal reference protein is CD45 or Histone H3.

In one embodiment, the analytes are RNA. In one embodiment, the steps of measuring are carried out by RT-qPCR or transcript counting.

In one embodiment, the control sample is from non-refractory AML cells.

In one embodiment, the control sample is from normal (non-AML) cells. For example, the control sample may be from healthy bone marrow.

In one embodiment, the MDM2 inhibitor comprises a small molecule inhibitor of MDM2.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), or Clofazimine.

In one embodiment, the MDM2 inhibitor comprises S-bepridil (Vascor).

In one embodiment, the MDM2 inhibitor comprises Protirelin (Thyrel TRH).

In one embodiment, the MDM2 inhibitor comprises Caramiphen (Oridine AT).

In one embodiment, the MDM2 inhibitor comprises Prenazone (Feprazone).

In one embodiment, the MDM2 inhibitor comprises Mephenoxalone.

In one embodiment, the MDM2 inhibitor comprises Azlocillin.

In one embodiment, the MDM2 inhibitor comprises Azaribine (Triazure).

In one embodiment, the MDM2 inhibitor comprises Clofazimine.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), Clofazimine, Nutlin, Nutlin3, Nutlin3a, Idasanutlin, MI-773, DS-3032(b), HDM201, BI 907828 or AMG 232.

In one embodiment, the MDM2 inhibitor comprises a Nutlin.

In one embodiment, the MDM2 inhibitor comprises Nutlin3.

In one embodiment, the MDM2 inhibitor comprises Nutlin3a.

In one embodiment, the MDM2 inhibitor comprises Idasanutlin.

In one embodiment, the MDM2 inhibitor comprises MI-773.

In one embodiment, the MDM2 inhibitor comprises DS-3032(b) (Daiichi Sankyo).

In one embodiment, the MDM2 inhibitor comprises HDM201 (Novartis).

In one embodiment, the MDM2 inhibitor comprises AMG 232 (Amgen).

In one embodiment, the MDM2 inhibitor comprises BI 907828 (Boehringer Ingelheim).

In one embodiment, the MDM2 inhibitor comprises a biologic. In one embodiment, the biologic comprises ALRN-6924 (Aileron). In one embodiment, the biologic is a peptide. The peptide may be a blocking peptide for MDM2. In one embodiment, the biological may be an antibody. The antibody may be a blocking peptide for MDM2.

In one embodiment, the MDM2 inhibitor comprises an aptamer. In one embodiment, the aptamer is an oligonucleotide that binds to MDM2.

In one embodiment the MDM2 inhibitor comprises a combination of one or more of the inhibitors described herein.

Selecting or Administering Treatment

In another aspect, there is provided a method of selecting a patient for treatment with an MDM2 inhibitor before or concurrently with chemotherapy, the method comprising: carrying out one of the above-described methods of predicting, and selecting the patient for treatment with an MDM2 inhibitor before or concurrently with chemotherapy if the patient is predicted to have AML refractory to chemotherapy or AML responsive the MDM2 inhibitor.

In one embodiment, the chemotherapy is induction therapy.

In one embodiment, the patient is selected for treatment with the MDM2 inhibitor concurrently with chemotherapy or induction therapy.

In another aspect, there is provided a method of treating a subject having refractory acute myeloid leukemia (AML), the method comprising: carrying out one of the above-described methods of predicting, and administering to the patient a treatment comprising an MDM2 inhibitor before or concurrently with chemotherapy if the patient is predicted to have AML refractory to induction therapy.

In one embodiment, the chemotherapy is induction therapy.

In one embodiment, the step of administering is carried out concurrently with chemotherapy or induction therapy.

In one embodiment, the MDM2 inhibitor comprises a small molecule inhibitor of MDM2.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), or Clofazimine.

In one embodiment, the MDM2 inhibitor comprises S-bepridil (Vascor).

In one embodiment, the MDM2 inhibitor comprises Protirelin (Thyrel TRH).

In one embodiment, the MDM2 inhibitor comprises Caramiphen (Oridine AT).

In one embodiment, the MDM2 inhibitor comprises Prenazone (Feprazone).

In one embodiment, the MDM2 inhibitor comprises Mephenoxalone.

In one embodiment, the MDM2 inhibitor comprises Azlocillin.

In one embodiment, the MDM2 inhibitor comprises Azaribine (Triazure).

In one embodiment, the MDM2 inhibitor comprises Clofazimine.

In one embodiment, the MDM2 inhibitor comprises the MDM2 inhibitor comprises S-bepridil (Vascor), Protirelin (Thyrel TRH), Caramiphen (Oridine AT), Prenazone (Feprazone), Mephenoxalone, Azlocillin, Azaribine (Triazure), Clofazimine, Nutlin, Nutlin3, Nutlin3a, Idasanutlin, MI-773, DS-3032(b), HDM201, BI 907828, or AMG 232.

In one embodiment, the MDM2 inhibitor comprises a Nutlin.

In one embodiment, the MDM2 inhibitor comprises Nutlin3.

In one embodiment, the MDM2 inhibitor comprises Nutlin3a.

In one embodiment, the MDM2 inhibitor comprises Idasanutlin.

In one embodiment, the MDM2 inhibitor comprises MI-773.

In one embodiment, the MDM2 inhibitor comprises DS-3032(b) (Daiichi Sankyo).

In one embodiment, the MDM2 inhibitor comprises HDM201 (Novartis).

In one embodiment, the MDM2 inhibitor comprises AMG 232 (Amgen).

In one embodiment, the MDM2 inhibitor comprises BI 907828 (Boehringer Ingelheim).

In one embodiment, the MDM2 inhibitor comprises a biologic. In one embodiment, the biologic comprises ALRN-6924 (Aileron). In one embodiment, the biologic is a peptide. The peptide may be a blocking peptide for MDM2. In one embodiment, the biological may be an antibody. The antibody may be a blocking peptide for MDM2.

In one embodiment, the MDM2 inhibitor comprises an aptamer. In one embodiment, the aptamer is an oligonucleotide that binds to MDM2.

In one embodiment the MDM2 inhibitor comprises a combination of one or more of the inhibitors described herein.

In one embodiment, the induction therapy comprises an anthracycline and cytarabine. In one embodiment, the anthracycline comprises daunorubicin.

Other induction therapy regiments are described above, and are envisaged for other embodiments.

EXAMPLE 1

Introduction

Despite recent advances in genetic markers that stratify AML patients into favorable, intermediate and adverse risk categories, refractory AML patients are found across all risk groups[4]. Recent studies have shown that mutations within core members of the Polycomb repressive complex 2 (PRC2), which deposits H3K27me3 marks, and alterations in H3K27me3 levels within bulk AML bone marrow (BM) cells have predictive value for overall survival and relapse[6,7].

However, there are no known biomarkers to prospectively identify refractory AML patients, nor are the molecular mechanisms underlying refractory AML known[5].

Herein, it is demonstrated that the expression of the accessory PRC2 member Polycomblike2 (PCL2/MTF2)[8] within the leukemic stem cell (LSC)-enriched $CD34^+CD38^-$ BM population predicts refractory AML at diagnosis. Furthermore, it is shown that MTF2 dictates global H3K27me3 levels within BM $CD34^+CD38^-$ cells, and that rescuing MTF2 expression within refractory AML cells reverses chemoresistance. Using an unbiased systems biology approach, it is determined that MTF2 regulates oncogenic and tumor suppressor networks. In particular, MTF2 deficiency elicits MDM2/p53-mediated defects in cell cycle regulation, apoptosis and chemoresistance. Targeting this dysregulated signaling pathway using MDM2 inhibitors sensitized refractory patient LSC-enriched populations to induction chemotherapeutics and prevented relapse in human AML patient-derived xenograft (PDX) mice. Biomarkers predictive of refractory AML and a treatment that targets refractory AML have been identified.

Materials and Methods

Reproducibility and Double-Blinded Acquisition of Data

In vitro and in vivo functional assays in this study were performed in a double-blinded manner to remove investigator bias whenever possible, as described in more detail below. Analysis of MTF2 and H3K27me3 expression in diagnostic AML patient bone marrow samples was performed without knowledge of the clinical outcome. Likewise, the Kaplan-Meier analysis of our AML cohort was also performed without knowledge of the molecular analysis of patient samples. Furthermore, to ensure reproducibility, the in vitro functional assays were performed by 2 different individuals (HBM, HJ). Data analysis was performed in an unbiased manner by use of preset algorithms to analyze data with the FlowJo, IDEAS and ImageJ OpenComet software.

Patient Treatment and Response Analysis

Diagnostic bone marrow samples from patients with AML were obtained after informed consent. Patients were treated as per the protocols at The Ottawa Hospital, Ontario, Canada. In addition to the usual supportive care, they received induction chemotherapy with Idarubicin (12 mg/m2 intravenously daily for 3 days) and Cytarabine (200 mg/m2/day by continuous intravenous infusion for 7 days). A bone marrow sampling was repeated upon recovery of blood counts and/or between days 25-40. Responsive disease was defined as <5% blasts in the bone marrow. Patients who had ≥5% blast in the marrow were designated as failing or resistant to induction, for the purposes of this study. These patients were then treated with a salvage chemotherapy and considered for an allogeneic hematopoietic cell transplant. Patients who did achieve a complete remission proceeded to receive consolidation and were considered for an allogeneic hematopoietic cell transplant.

Umbilical Cord Blood and Bone Marrow Samples

Human umbilical cord blood samples were obtained. Informed consent for collection was obtained, and research use of the cord blood samples was approved. AML patient bone marrow samples were collected after informed consent. Procurement and use of patient samples for research was approved by The Ottawa Health Science Network Research Ethics Board.

Isolation of Mononuclear Cells from Umbilical Cord Blood

Hespan (B. Braun Medical Inc) was used for mononuclear cell isolation from umbilical cord blood. Cord blood was mixed with Hespan at a final ratio of 5:1 and centrifuged at 50 RCF for 10 minutes at room temperature. Post-centrifugation the serum supernatant containing the mononuclear cells was collected and centrifuged at 400RCF for 10 minutes. Red blood cells were then lysed with Red Blood Cell lysis buffer (1 g/L KHCO3, 8.2 g/L $NH_4Cl$, 0.37 g/L EDTA) to eliminate residual red blood cells before being frozen down in 10% DMSO using an ethanol-based control rate freezer (Kinetic), allowing high viability after thawing.

Isolation of Mononuclear Cells from Bone Marrow Aspirates

Ficoll (GE Healthcare Life Sciences) was used for mononuclear cell isolation from bone marrow aspirates. Density centrifugation to isolate mononuclear cells using Ficoll was done at 400 RCF for 20 minutes. All density centrifugations were done at room temperature, without brakes. Red blood cells were lysed and cells frozen as described above.

Enrichment of Stem and Progenitor Populations

Lineage-negative (Lin$^-$) umbilical cord blood or bone marrow cells were obtained using the EasySep™ Human Progenitor Cell Enrichment Kit with Platelet Depletion to enrich for hematopoietic stem and progenitor cells (HSPCs). CD34$^+$ positive selection was performed on Lin$^-$ cells, using the EasySep™ Human CD34$^+$ selection kit (Stem Cell Technologies).

For the experiments using CD34$^+$CD38$^-$ cells, Lin$^-$ cells were directly stained for CD34$^+$ (Clone 4H11) and CD38$^+$ (HIT2) cell surface markers and sorted for CD34$^+$CD38$^-$ cells using the Beckman Coulter MoFlo sorter.

Lentivirus Production of MTF2 shRNA 293T cells were co-transfected with lentiviral plasmids pMD2G, pPAX2 and pGIPZ encoding scramble or MTF2 shRNAs (ThermoScientific) using polyethylenimine (see Table 1). Supernatant containing the virus was collected 48 and 72 hours post-transfection. Virus was concentrated through ultracentrifugation and cells were infected at a MOI of 100.

TABLE 1

|  | shRNA Sequence |
|---|---|
| MTF2 shRNA Clone 3 | TAATGTATGTCATAAGCTC |
| MTF2 shRNA Clone 7 | TTGGCTTTATGTCCATCCT |
| Scrambled shRNA | GTTACACGATATGTTATCA |

Lentiviral-Mediated MTF2 Knockdown of HSPCs from Umbilical Cord Blood Cells

HSPCs (Lin$^-$CD34$^+$) were maintained in IMDM media containing bovine serum albumin, insulin, and transferrin (Stem Cell Technologies), 1% PenStrep (ThermoFisher), SCF (100 ng/mL), TPO (50 ng/mL), FLT3 (100 ng/mL), 1% Glutamax (InVitrogen), and LDL (1 µg/ml) (Calbiochem). Growth factors were purchased from Peprotech. On Day 1 of infection, cells were incubated with polybrene (Sigma) (6 mg/ml) for 2 hours at 37° C., then combined with viral supernatants containing either a GFP-tagged MTF2 shRNA clone or a scrambled shRNA control (ThermoFisher) at a MOI of 100. Cells were centrifuged at 400 g for 20 minutes, then maintained at 37° C. On Day 2, the infection was repeated. Cells were grown for 3 days using a fed-batch culture system[21], then sorted for high GFP-expression and viability by negative selection of Propidium Iodide using the Beckman Coulter MoFlo sorter.

Lentiviral-Mediated Rescue of MTF2 Expression within Patient Leukemic Cells

Lin$^-$CD34$^+$ primary AML bone marrow cells were maintained in IMDM media containing SCF (100 ng/mL), FLT3 (50 ng/mL), IL-3 (20 ng/mL), G-CSF (20 ng/mL) and 10$^{-4}$M Beta-mercaptoethanol[21]. Growth factors were purchased from Peprotech. On Day 1 of infection, cells were incubated with polybrene (6 mg/ml) for 2 hours at 37° C., then combined with viral supernatants containing either a GFP-tagged MTF2 overexpression vector clone or an empty vector control at a MOI of 30.

Intracellular Staining

Cells were sorted using cell surface markers, then fixed in 4% PFA, permeabilized with 0.3% Triton and stained for MTF2 (Genway, clone M96), EZH2 (Millipore, clone AC22), SUZ12 (Millipore, clone 2AO9), H3K27me3 (Cell Signaling, clone C36B11), PCNA (Santa Cruz, clone C10), p53 (Cell Signaling, clone 1C12), or MDM2 (Santa Cruz, clone C18) and appropriate secondary antibodies. Protein expression was determined by flow cytometry compared with an isotype-only control and ran on the LSRFortessa™ Cell Analyzer (BD Biosciences). Data analysis was performed using FlowJo v10.2 to compare mean fluorescent intensity values.

Imaging Flow Cytometry—Amnis

For cell cycle analysis, cells were fixed and stained with DRAQ5 (BD Biosciences) to assess cell cycle state. For assessing p53 signaling and MTF2 rescue experiments, cells were stained with antibodies against p53, MDM2 or H3K27me3 as above and with DRAQ5 for nucleic acid detection. Cells were analyzed using the ImageStream imaging flow cytometer (Amnis). The nuclear contents of each protein were determined using the preset wizard tool "Nuclear Localization", within the Amnis IDEAS analysis software.

Apoptosis Assay

Apoptosis was assessed in sorted cells by the dual staining of AnnexinV and 7-AAD (eBiosciences). Flow cytometric analyses of treated samples were performed consistently, using the same gating strategy throughout. Viable cells were categorized as being AnnexinV and 7-AAD negative, late apoptotic/dead cells were categorized as being AnnexinV and 7-AAD positive.

Comet Assay

Alkaline comet assays were performed using GelBond Films and buffers were prepared as described[22]. Slides were stained with SYBR Gold and imaged using Zeiss Axio2 Imaging inverted microscope equipped with a 5× Plan-NEOFLUAR 0.3NA objective and an AxioCam MRm camera through a FITC-compatible filter. At least 10 random fields containing a minimum of 20 non-overlapping comets in each group total were photographed. Blinded imaging acquisition and analysis was performed using ImageJ software (NIH) and the OpenComet comet assay plugin calculating Olive moment (arbitrary units) on the basis of comet head and tail sizes (measured in pixels) and their integral intensity. The magnitude of these parameters depends on time of electrophoresis, staining brightness and image magnification, which were constant within each assay and between experiments. Comet assays were independently repeated using HSPCs isolated from 3 different UCB samples. Statistical significance was determined by two-way ANOVA using GraphPad Prism software version 6.

RNA-Seq and ChIP-Seq

HSPCs (Lin$^-$CD34$^+$) were transduced either with the GFP-tagged MTF2 shRNA clone or a scrambled shRNA control. The transduced GFP$^+$ cells were sorted 72 hours post transduction using a MoFlo sorter. RNA was extracted from 150,000 cells per condition for RNA-seq analysis. RNA was isolated (Arcturus PicoPure Kit, LifeTech) and DNase treated (Qiagen). Quality of RNA was determined using a Bioanalyzer. Library preparation was performed using (TruSeq Library Prep Kit, Illumina), and sequenced on a HiSeq 2000 (Illumina). Replicate data was analyzed using TopHat v1.4.1 and Cuffdiff v1.3.0[23] to map reads to a reference human genome assembly (hg19) and determine expression differences against the Ensembl release 67 gene model. Significant fold changes were determined using Benjamini-Hochberg corrected p value of 0.05. Data was analyzed using DAVID bioinformatics tool for functional annotation[24,25] and Cytoscape with Enrichment Map plugin for visualization[26,27]. RNA-seq targets were validated by RT-qPCR after RNA was converted to cDNA using Superscript II (LifeTech). The qPCR experiments were performed on LightCycler 480 (Roche).

For ChIP-seq, CD34+CD38− sorted cells were crosslinked with 1% formaldehyde for 10 minutes at room temperature. Samples were sheared using a Covaris sonicator until DNA reached a final size of 100-300 bp. 750 ng of *drosophila* spike in chromatin (Active Motif) was added to each sonicated sample. 4 ug of anti-H3K27me3 antibody (Cell Signaling, c36B11) or H3 (Abcam, ab1791) was bound to pre-blocked Protein A magnetic beads (Millipore) in combination with 2 ug of Spike-in antibody (Active Motif) for 12 hours. The beads were then combined with sonicated sample containing *Drosophila* spike in chromatin and incubated overnight. After incubation, beads were collected and DNA-antibody complexes were eluted at 65° C. Crosslinks were reversed overnight at 65° C. Samples were treated with Proteinase K (Fisher Scientific) and RNase A (Fisher Scientific) and DNA was purified using phenol-chloroform. All ChIP-seq experiments were cell number normalized and 150,000 cells per biological sample were used for each H3 and H3K27me3 ChIP experiment.

DNA was analyzed for quality, quantity and size using Fragment Analyzer (AAT1) and Qubit (ThermoFisher). For sequencing total ChIP DNA was used for library preparation (NextFlex Illumina Chip-seq kit). All samples underwent 1×75 cycles of single-end sequencing on NextSeq 500 (Illumina). Reads were mapped separately to the reference human (hg19) and *Drosophila melanogaster* (BDGP6.0) genome assemblies using Bowtie 2.2.6[28]. For each sample, the number of *Drosophila* spike-in reads was used to calculate normalization factor, with a greater number of *Drosophila* reads indicating a smaller amount of ChIP human DNA.

Principal Component Analysis (PCA)

A BED file of non-overlapping 20 kb windows was generated to cover the human (hg19) genome using the BEDTools 'makewindow' command[30]. The BEDTools 'multicov' command was used to count the number of reads overlapping each window (calculated separately for H3 and H3K27me3 ChIP-seq data), and the data were loaded into DESeq2[31]. For each sample, the ratio of *Drosophila* spike-in reads to the number of spike-in reads in the 'Basal-1' sample was used in lieu of 'estimateSizeFactors', and the DESeq2 'estimateDispersions' and 'nbinomWaldTest' functions were applied to the data set. The normalized count matrix was then transformed using the 'rlog' regularized log transformation, and PCA was performed on the rlog-transformed normalized count matrix using the DESeq2 'plotPCA' function on the most variable 5000 20 kb windows (ntop=5000 parameter for plotPCA).

Differential H3K27me3 Coverage

Regions of differential H3K27me3 coverage were detected in the ChIP-seq data using diffReps[29] to compare coverage in refractory MTF2 patient CD34+CD38− cells against coverage in responsive patient CD34+CD38− bone marrow cells with normal MTF2 levels, and in MTF2 deficient CD34+CD38− cells (transduced with SH3 & SH7) against healthy CD34+CD38− bone marrow cells. For each comparison, H3K27me3 ChIP-seq reads were first filtered to remove reads mapping to ENCODE ChIP-seq blacklist regions, and diffReps was run using normalization factors calculated as described above for PCA analysis. Association between regions of reduced H3K27me3 and genes was taken directly from the diffReps output files.

Hierarchical Clustering

The matrix of rlog-transformed count values was used to generate a matrix of pairwise Euclidian distances between samples. These distances were hierarchically clustered using complete linkage clustering, and a heatmap plotted to illustrate the distance relationships between samples.

Genome Coverage Calculations

BEDTools was used to convert BAM files of mapped reads into BED files, extend reads to 200 bp length, and to calculate coverage depth across the human genome. The coverage depth was scaled by the ratio of *Drosophila* spike-in reads in the 'Basal-1' sample to the number of spike-in reads in the sample in question (i.e. the inverse of the size factor estimates used for DESeq2 analysis), and converted to bigWig format using the UCSC 'bedGraphToBigWig' tool[32].

Validation of ChIP-seq targets was completed by ChIP-qPCR. All qPCR analysis was completed on a Roche Light Cycler 480 using Sybr Green MasterMix (Roche) and 0.1 mM primers.

Methyl-ChIP-qPCR

Methyl ChIP-qPCR analyses were performed using the EpiMark Methylated DNA Enrichment Kit (New England Biosciences), according to manufacturer's instructions. Briefly, DNA was isolated from Lin−CD34+ cells isolated from the bone marrow aspirates of healthy and patients with AML. DNA was fragmented and combined with methyl-CpG-binding domain protein 2 (MBD2) bound to magnetic beads to capture methylated DNA. Methylated CpG DNA was eluted from beads. Enriched DNA was used for RT-qPCR using primers listed in Extended Data Table 4.

Animal Study Approval

All animal experiments were conducted with approval from the University of Ottawa Animal Care Committee, in accordance with the Canadian Council on Animal Care Standards and the Province of Ontario's Animals for Research Act. NOD-scid IL2Rgamma$^{null}$ (NSG) mice were purchased from Jackson Labs. Mice were maintained in sterile housing conditions and given autoclaved chow and water ad libitum.

AML Xenograft Mouse Model

Anonymized, coded primary diagnostic AML bone marrow (BM) samples were obtained from patients. Researchers were blinded to the clinical diagnosis and outcome of the AML patients until the MTF2 and H3K27me3 analysis was complete. AML patient BM cells were expanded in NSG mice to obtain large numbers of patient derived xenograft (PDX) cells for the animal studies. Briefly, NSG mice were sublethally irradiated with 300 Rads (Gammacell 3000) and transplanted via tail vein with 1 million BM cells. After 6-8 weeks, BM cells from the tibiae and femurs of the NSG mice were harvested and frozen in 10% DMSO using a controlled rate freezer (Kinetic) and stored at −150° C. for future studies.

In Vivo Treatment

Female NSG>7 week old mice were sublethally irradiated with 300 Rads and transplanted via tail vein with 1 million PDX cells; n=8 mice were transplanted per AML PDX sample. The peripheral blood of the transplanted mice was collected from the saphenous vein 3-4 weeks post-transplantation and analyzed for CD45+CD33+ cells. Upon >20% CD45+CD33+ cells in the peripheral blood, mice were randomized into 4 treatment groups (n=4 PDX samples; n=2 mice per group; n=8 mice total per group) and treated with i) DMSO, ii) nutlin3A, iii) induction therapy or iv) combination therapy (see below for details). To conceal the identity of the treatment received, syringes containing the vehicle control or drugs were prepared and coded by one person, while another person administered the treatment intravenously via tail vein. Coded treatments were assigned to the corresponding mouse.

Mice belonging to the induction therapy cohort, were treated using the previously published 5+3 treatment regimen[20]. The mice were treated for the first three days with both Cytarabine (50 mg/kg) and Daunorubicin (1.5 mg/kg), while during the last 2 days the mice were treated with Cytarabine (50 mg/kg) alone. Mice belonging to the combination therapy cohort, were given the 5+3 treatment regimen in combination with Nutlin3A (12 mg/kg). Nutlin3a was given for the entire duration of the 5 days. Weights were taken daily during treatment, and doses were recalculated by the researcher preparing the syringes to ensure that the mice received a consistent dose.

Post-treatment, the weights of the mice were monitored every 5 days. Moribund endpoint was determined as >20% loss in body weight, loss of mobility, loss of appetite and hunched posture. Otherwise if mice survived, endpoint was at 16 weeks post-treatment, when the experiment was terminated. Upon reaching endpoint, the BM of the mice was harvested and human cell engraftment was analyzed by flow cytometry (described below).

Lineage Determination of PDX In Vivo Samples

To analyze PDX cells post-treatment, cells were harvested from the peripheral blood or bone marrow of NSG mice. To assess human cell engraftment in the mice, red blood cells were lysed and mononuclear cells were stained with antibodies directed against human specific lineage markers CD34 (Clone 4H11), CD38 (HIT2), CD45 (H1130), CD33 (P67.6), CD19 (HIB19), CD15 (H198), CD3 (OKT30), CD4 (OKT4), CD8 (OKT8), CD14 (61D3) (eBioscience). Cells were then analyzed by flow cytometry using the BD LSR Fortessa II.

Immunohistochemistry

Blinded analysis of bone marrow cytospins of patient derived xenograft (PDX) mice, were performed using a total of 500,000 cells per slide. The slides were stained with Wright-Giemsa stain for 5 minutes and de-stained in water (PH 7.2) for 2 minutes. This process was repeated twice for each slide and photomicrographs were obtained using a Zeiss Inverted LSM510 microscope. The pictures were taken at a magnification of 40×.

Cell Viability Assays

Lin⁻CD34⁺ cells isolated from either umbilical cord blood or primary AML patient bone marrow aspirates were transduced as above, sorted for GFP⁺ and cultured in 96-well plates at 100,000 cells/100 uL/well in duplicates. The drugs Daunorubicin, Cytarabine, Nutlin3a and M1773 were dissolved in DMSO. Cytarabine and Daunorubicin were added at concentrations of 1 µM and 0.5 µM, respectively. After 1 hour of incubation with Daunorubicin, cells were collected and transferred into fresh media to remove Daunorubicin from the media. The MDM2 pathway inhibitors, Nutlin3a and M1773 were added at concentrations of 1 µM.

Statistics

All data were expressed as mean±SEM or SD. Data was analyzed using Prism 6.0 (GraphPad Software). Two-way Anova measured statistical significance between the conditions. A p value <0.05 was used as a cut-off to indicate statistical significance.

Results & Discussion

Global levels of the repressive histone mark H3K27me3 levels were analyzed within CD34⁺CD38⁻ cells isolated from 32 blinded diagnostic AML BM aspirates isolated from patients who underwent induction therapy (Table 2-4).

Table 2 depicts clinical characteristics of responders versus non-responders within local AML cohort.

TABLE 2

|  | Responder (n = 20) | Non-responder (n-12) |
| --- | --- | --- |
| Median age (years) [range] | 57.3 [28.2-71.1] | 62.7 [22.4-67.9] |
| WBC at diagnosis [range] | 11.2 [1.4-138.4] | 5.5 [0.7-122] |
| Median bone marrow blast % at diagnosis [range] | 90 [29-100] | 71.5 [22-95] |
| Cytogenetic Risk group Favorable/intermediate/adverse | 7/12/1 | 2/5/5 |
| MTF2 Basal/low | 14/6 | 1/11 |
| % Complete remission | 100 | 0 |
| # alloHCT | 5 | 9 |
| # deaths | 7 | 11 |
| Median overall survival (days) | 771 [149-1951] | 322 [41-972] |

Table 3 depicts clinical characteristics of MTF2 Basal versus MTF2 Low patients within local AML cohort.

TABLE 3

|  | All (n = 32) | MTF2 Basal (n = 15) | MTF2 Low (n = 17) |
| --- | --- | --- | --- |
| age | 58.4 [22.4-71.1] | 58.8 [28.2-68] | 56.1 [22.4-71.1] |
| WBC at diagnosis [range] | 8.05 [0.7-138.4] | 10.8 [1.4-138.4] | 5.5 [0.7-122] |
| Median bone marrow blast % at diagnosis [range] | 85 [22-100] | 85 [29-100] | 85 [22-95] |
| Cytogenetic risk group (fav/inter/adverse) | 9/17/6 | 5/10/0 | 4/7/6 |
| Response to first induction n (%) | 20 (62.5) | 14 (93.3) | 6 (35.3) |
| # alloHCT (%) | 14 (43.8) | 7 (46.6) | 7 (41.2) |
| # of deaths (%) | 18 (56.3) | 6 (40) | 12 (70.6) |
| Died from leukemia n(%) | 15 (46.7) | 3 (20) | 12 (70.6) |
| Median Overall Survival (days) | 729 [41-1951] | 1548 [41-1951] | 519 [53-1030] |

Table 4 summarizes patient data.

TABLE 4

(Part 1)

| Patient # | age at diagnosis | date of diagnosis | WBC at diagnosis | % bone marrow blasts at diagnosis | molecular | genetic risk group |
| --- | --- | --- | --- | --- | --- | --- |
| 1 | 63.0 | 15-Dec-11 | 114.6 | 69 | −y, add(14) | inter |
| 2 | 60.6 | 23-Apr-14 | 18 | 95 | del(11) | inter |
| 3 | 22.4 | 30-Jun-14 | 4.2 | 95 | 11q23 | adverse |
| 4 | 66.1 | 05-Nov-12 | 10.8 | 95 | del(13) | inter |
| 5 | 62.6 | 13-Jun-11 | 5.3 | 95 | −7 | adverse |
| 6 | 28.2 | 29-May-14 | 113.6 | 70 | inv(16) | fav-cbf |
| 7 | 56.1 | 25-May-12 | 6.9 | 30 | complex | adverse |
| 8 | 31.9 | 15-Oct-12 | 122 | 80 | Npm | fav-npm |
| 9 | 41.4 | 13-Mar-14 | 1.2 | 90 | t(15;17) | fav-apl |
| 10 | 59.5 | 23-Oct-12 | 2.6 | 33 | normal | inter |
| 11 | 71.1 | 16-Jul-13 | 2.4 | 50 | normal | inter |
| 12 | 65.5 | 06-Jul-12 | 5.7 | 40 | complex | adverse |
| 13 | 66.2 | 27-Jun-11 | 12 | 85 | normal | inter |
| 14 | 50.5 | 12-Sep-11 | 15.5 | 90 | Npm | fav-npm |
| 15 | 58.8 | 08-Nov-11 | 1.9 | 85 | Npm | fav-npm |
| 16 | 64.5 | 22-Jul-13 | 57 | 90 | Npm | fav-npm |
| 17 | 51.1 | 25-Oct-12 | 11.5 | 90 | Npm | fav-npm |
| 18 | 34.2 | 16-May-11 | 9.2 | 70 | t(6;22) | inter |
| 19 | 52.1 | 10-Jul-12 | 4.1 | 22 | complex | adverse |
| 20 | 67.9 | 20-Dec-13 | 3.4 | 26 | del(12) | inter |
| 21 | 29.5 | 21-Nov-13 | 2.1 | 95 | −y | inter |
| 22 | 68.0 | 25-Nov-13 | 14.6 | 68 | inv(16) | fav-cbf |
| 24 | 32.9 | 16-Jun-15 | 26 | 90 | normal | inter |
| 31 | 62.9 | 26-May-15 | 0.7 | 63 | normal | inter |
| 32 | 46.1 | 29-May-15 | 2.7 | 38 | t(8;21) | fav-cbf |
| 23 | 42.1 | 14-Mar-16 | 81.3 | 95 | del(5q) | adverse |
| 25 | 69.8 | 26-Sep-16 | 17.5 | 86 | add(2) | inter |
| 26 | 57.9 | 11-Mar-16 | 1.4 | 90 | add(15) | inter |
| 27 | 53.5 | 24-Jul-14 | 0.8 | 63 | normal | inter |
| 28 | 68.0 | 11-Apr-16 | 138.4 | 100 | normal | inter |
| 29 | 63.8 | 14-Apr-16 | 88.6 | 92 | −y | inter |
| 30 | 56.7 | 22-Apr-16 | 1.8 | 29 | normal | inter |

(Part 2)

| Patient # | treatment | responder | MTF2 status | H3k27me3 Status | BMT (y/n) | date of BMT |
| --- | --- | --- | --- | --- | --- | --- |
| 1 | I | y | b | b | y | 22-Dec-14 |
| 2 | I | y | b | b | y | 15-Oct-14 |
| 3 | I | n | L | L | y | 02-Oct-14 |
| 4 | I | y | b | b | y | 04-Apr-13 |
| 5 | I | n | L | L | n | n/a |
| 6 | I | y | b | b | n | n/a |
| 7 | I | n | L | L | n | n/a |
| 8 | I | n | L | L | y | 31-May-13 |
| 9 | I | y | L | L | n | n/a |
| 10 | I | y | b | L | y | 02-May-13 |
| 11 | I | y | L | L | n | n/a |
| 12 | I | n | L | L | n | n/a |
| 13 | I | n | L | L | y | 28-Feb-12 |
| 14 | I | y | L | L | n | n/a |
| 15 | I | y | b | b | n | n/a |
| 16 | I | n | L | L | n | n/a |
| 17 | I | y | b | b | n | n/a |
| 18 | I | y | b | b | y | 07-Sep-11 |
| 19 | I | n | L | L | y | 13-Dec-12 |
| 20 | I | n | L | L | y | 05-Jun-14 |
| 21 | I | y | b | b | y | 26-Mar-14 |
| 22 | I | y | b | b | n | n/a |
| 24 | i | y | L | L | y | 06-Nov-15 |
| 31 | i | n | L | L | n | n/a |
| 32 | i | y | b | b | n | n/a |
| 23 | I | y | L | L | y | 04-Aug-16 |
| 25 | i | y | L | L | n | n/a |
| 26 | i | y | b | b | y | aug 3 2016 |
| 27 | i | n | L | L | n | n/a |
| 28 | i | y | b | b | n | n/a |
| 29 | i | n | b | b | n | n/a |
| 30 | i | y | b | b | n | n/a |

TABLE 4-continued (Part 3)

| Patient # | date of relapse | date of death | date of last f/u | OS | dead/alive (1/0) | cause |
|---|---|---|---|---|---|---|
| 1 | 17/Sep/14 | 11-Mar-16 | 11-Mar-16 | 1548.0 | 1 | other |
| 2 | n/a | 15-Jul-16 | 15-Jul-16 | 814.0 | 1 | other |
| 3 | n/a | 11-Mar-15 | 11-Mar-15 | 254.0 | 1 | leuk |
| 4 | n/a | n/a | 21-Nov-16 | 1477.0 | 0 | n/a |
| 5 | 1/Nov/11 | 27-Nov-11 | 27-Nov-11 | 167.0 | 1 | leuk |
| 6 | n/a | n/a | 21-Mar-17 | 1027.0 | 0 | n/a |
| 7 | n/a | 17-Jul-12 | 17-Jul-12 | 53.0 | 1 | leuk |
| 8 | 4/Sep/13 | 14-Sep-13 | 14-Sep-13 | 334.0 | 1 | leuk |
| 9 | n/a | n/a | 06-Jan-17 | 1030.0 | 0 | n/a |
| 10 | 3/Oct/13 | 27-Feb-14 | 27-Feb-14 | 492.0 | 1 | leuk |
| 11 | 15/May/14 | 15-Jul-15 | 15-Jul-15 | 729.0 | 1 | leuk |
| 12 | n/a | 23-Feb-13 | 23-Feb-13 | 232.0 | 1 | leuk |
| 13 | n/a | 23-Jun-03 | 23-Jun-13 | 727.0 | 1 | leuk |
| 14 | 22/Sep/12 | 12-Feb-13 | 12-Feb-13 | 519.0 | 1 | leuk |
| 15 | n/a | n/a | 12-Mar-17 | 1951.0 | 0 | n/a |
| 16 | n/a | 12-Jan-15 | 12-Jan-15 | 539.0 | 1 | leuk |
| 17 | n/a | n/a | 22-Feb-17 | 1581.0 | 0 | n/a |
| 18 | n/a | n/a | 21-Feb-16 | 1742.0 | 0 | n/a |
| 19 | 9/Jul/14 | 15-Aug-14 | 15-Aug-14 | 766.0 | 1 | leuk |
| 20 | 6/Jul/14 | 26-Oct-14 | 26-Oct-14 | 310.0 | 1 | leuk |
| 21 | n/a | n/a | 19-Dec-16 | 1124.0 | 0 | n/a |
| 22 | n/a | n/a | 27-Mar-17 | 1218.0 | 0 | n/a |
| 24 | n/a | n/a | 20-Mar-17 | 643.0 | 0 | n/a |
| 31 | n/a | 25-May-16 | 25-May-16 | 365.0 | 1 | leuk |
| 32 | n/a | n/a | 29-Nov-16 | 550.0 | 0 | n/a |
| 23 | n/a | n/a | 06-Mar-17 | 357.0 | 0 | n/a |
| 25 | n/a | n/a | 22-Mar-17 | 177.0 | 0 | n/a |
| 26 | n/a | n/a | 13-Mar-17 | 367.0 | 0 | n/a |
| 27 | n/a | n/a | 19-Mar-17 | 969.0 | 0 | n/a |
| 28 | 8/Sep/16 | 09-Jun-16 | 14-Nov-16 | 217.0 | 1 | leuk |
| 29 | n/a | 25-May-16 | 25-May-16 | 41.0 | 1 | other |
| 30 | 30/Aug/16 | 18-Sep-16 | 18-Sep-16 | 149.0 | 1 | leuk |

Figure 2:
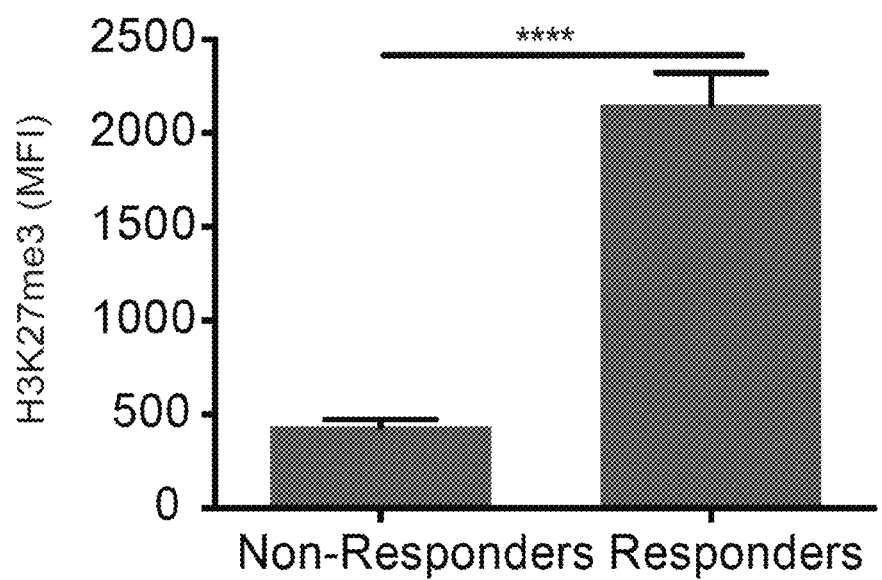
FIG. 2 depicts H3K27me3 mean fluorescence intensity (MFI) obtained from flow cytometry analysis of 32 diagnostic BM samples demonstrates that reduced levels of H3K27me3 correlates with poor response to induction therapy.
Figure 3:
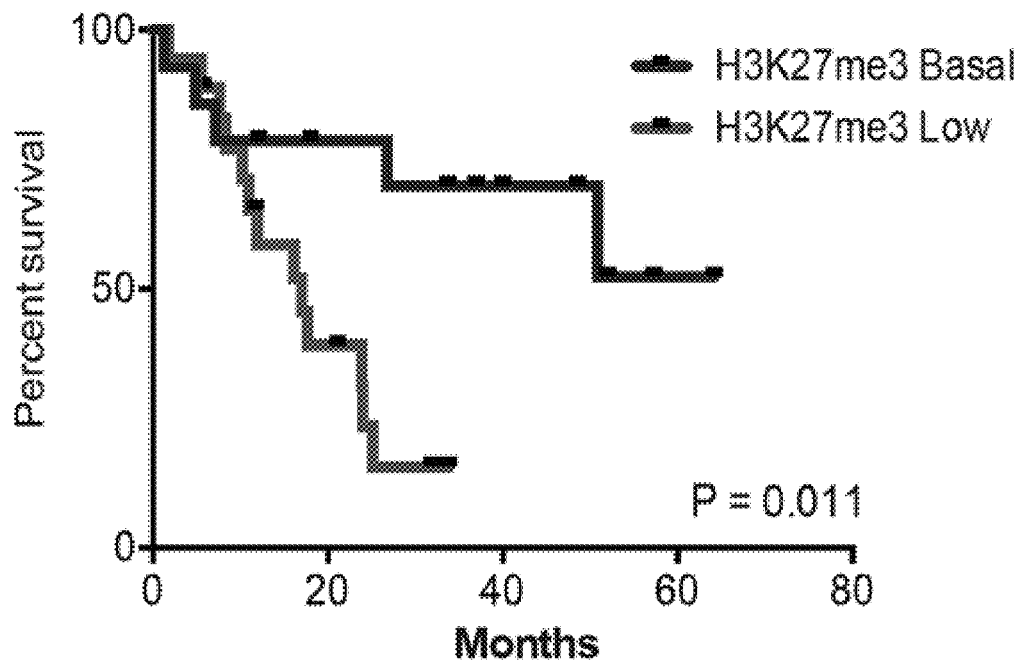
FIG. 3 depicts survival analysis of the 32 AML patients treated by induction therapy shows H3K27me3 levels within patient $CD34^+CD38^-$ cells correlated with patient outcome; P value was calculated using Log-rank (Mantel-Cox) test.
Figure 4:
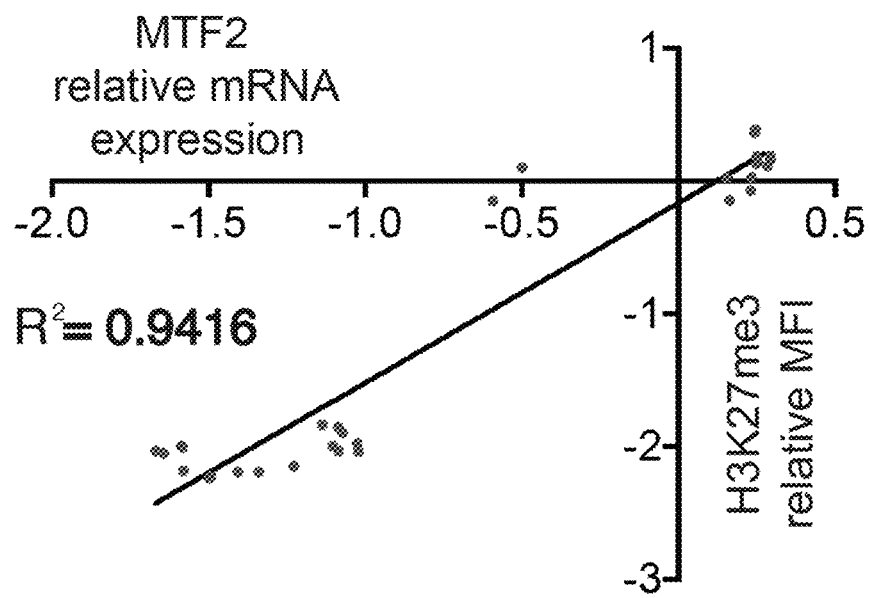
FIG. 4 depicts linear regression analysis of PRC2 complex member MTF2 relative to H3K27me3 expression.
Figure 5:
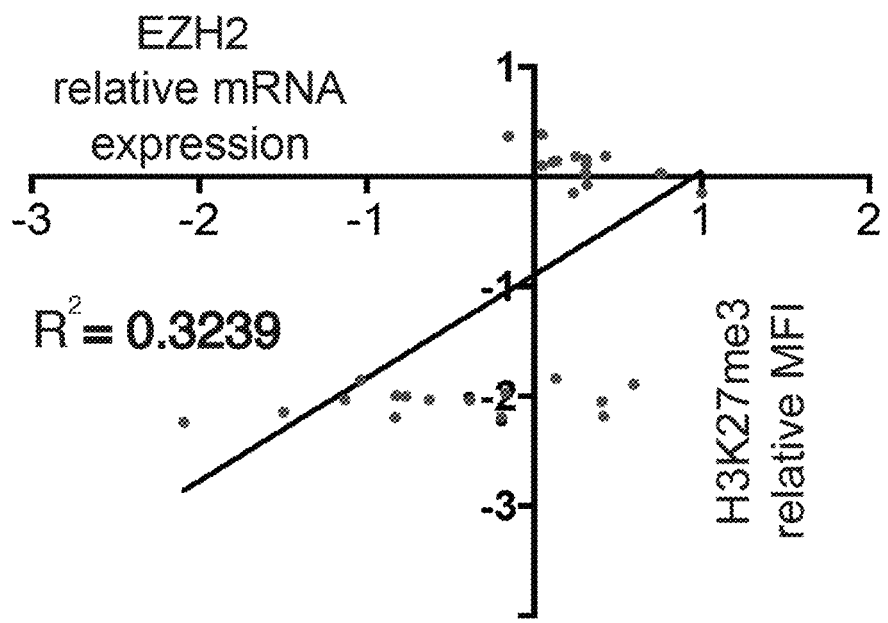
FIG. 5 depicts linear regression analysis of PRC2 complex member EZH2 relative to H3K27me3 expression.
Figure 6:
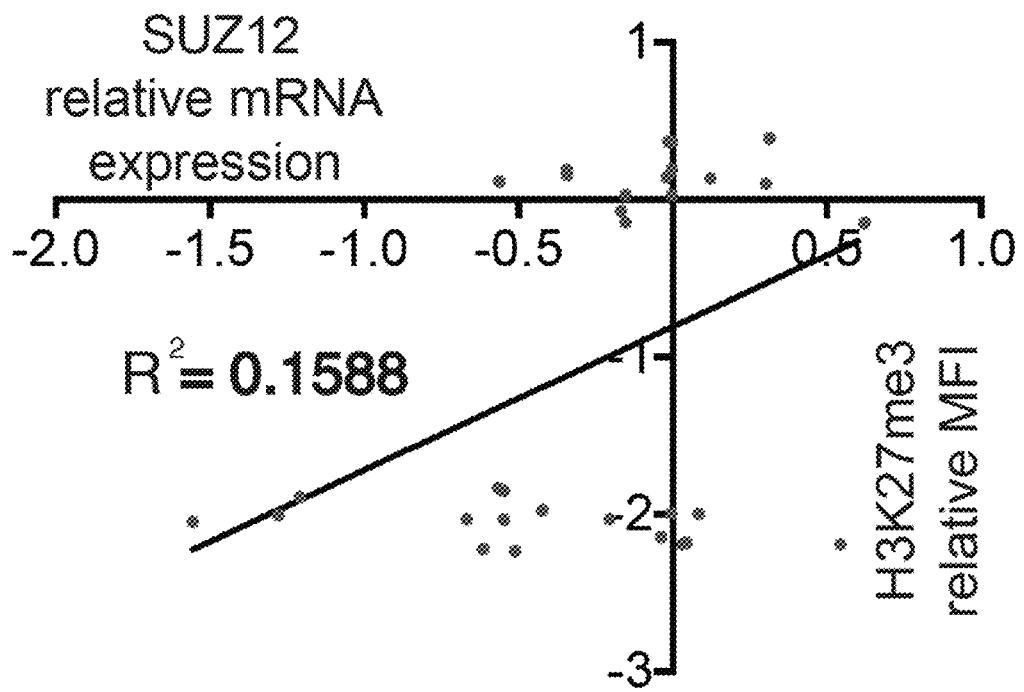
FIG. 6 depicts linear regression analysis of PRC2 complex member SUZ12 relative to H3K27me3 expression.
Figure 7:
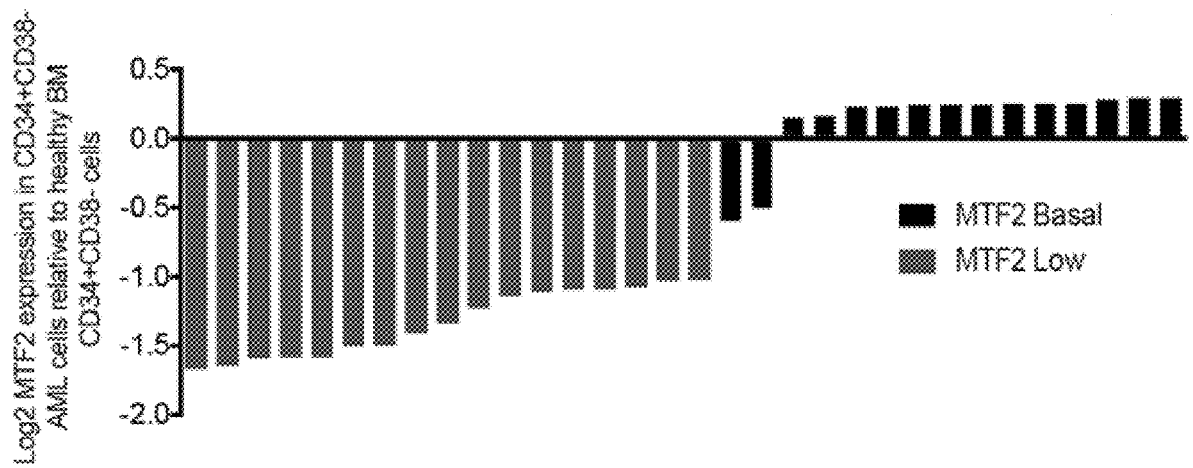
FIG. 7 depicts MTF2 expression within $CD34^+CD38^-$ cells isolated from 32 diagnostic AML BM aspirates compared to $CD34^+CD38^-$ HSPCs from 7 healthy BM aspirates assessed by RT-qPCR. 17 aspirates were determined to have low levels of MTF2 expression (Log 2 expression <−1) and 15 aspirates were determined to have basal levels of MTF2 expression (Log 2 expression −1 to +1).
Figure 8:
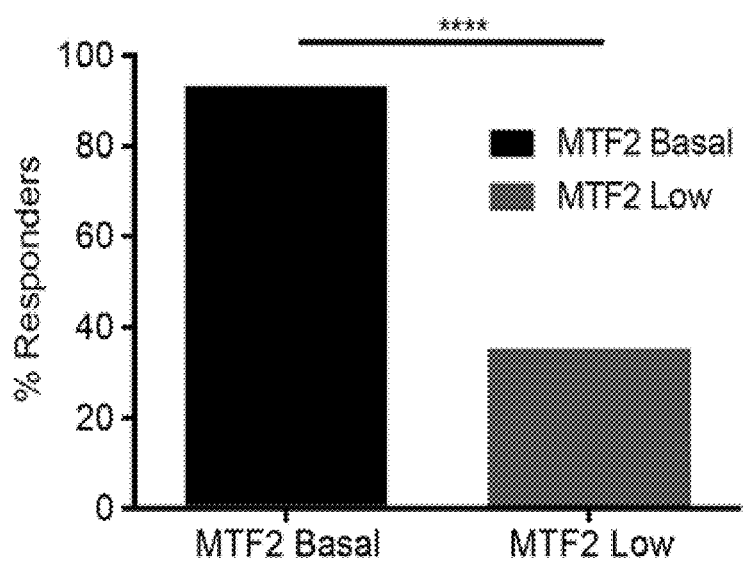
FIG. 8 depicts a double blinded drug response analysis determined that patients within our cohort with low MTF2 expression responded poorly to standard induction chemotherapy.
Figure 36:
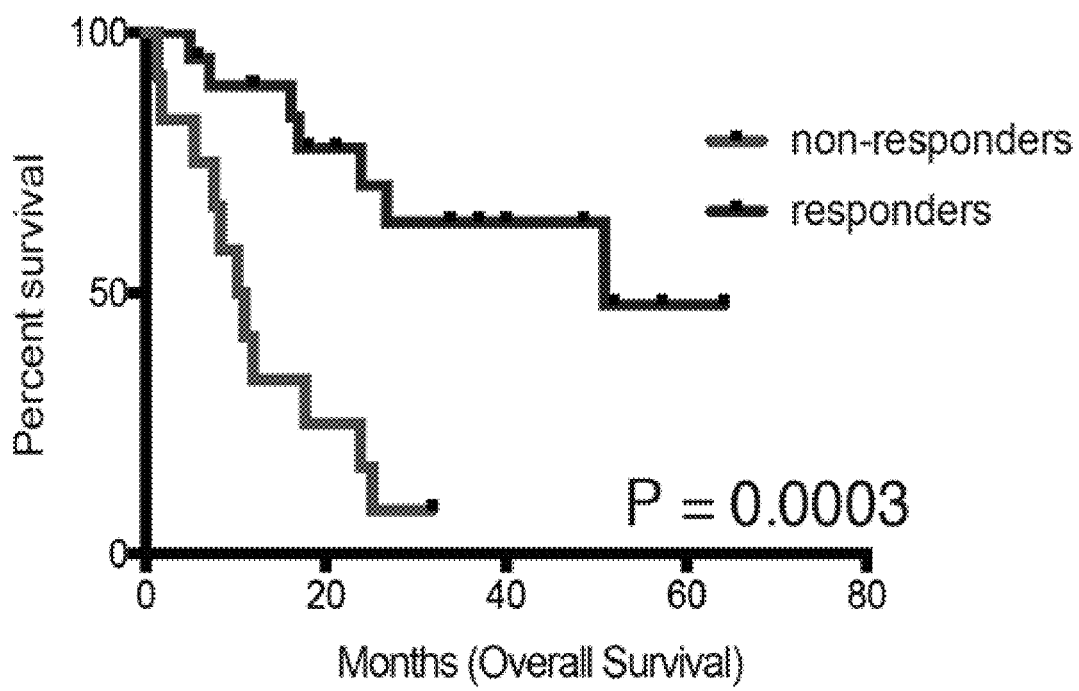
FIG. 36 depicts results of MTF2 mRNA expression analyzed within CD34⁺CD38⁻ LSC enriched cells from the local patient cohort (n=32) at diagnosis and normalized to MTF2 mRNA expression within CD34⁺CD38⁻ cells isolated from healthy bone marrow aspirates (n=7). Kaplan-Meier analysis of local patient cohort (n=32) shows that patients who do not respond to traditional induction chemotherapy regimen have significantly reduced overall survival compared to patients who respond to treatment.
Figure 37:
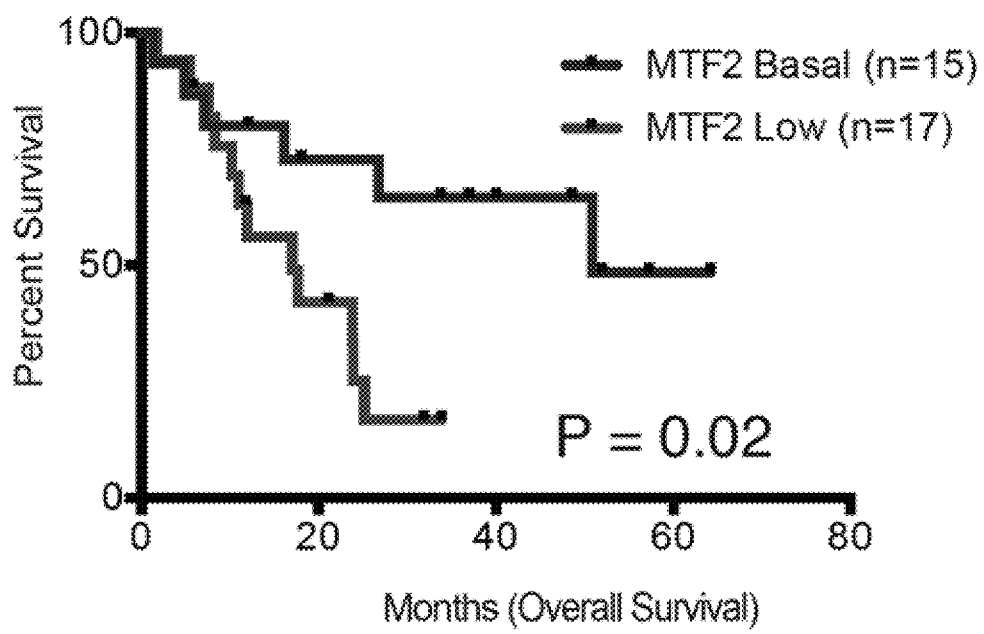
FIG. 37 depicts a Kaplan-Meier analysis of local patient cohort (n=32) treated with traditional induction chemotherapy regimen, which shows that patients expressing low MTF2 (n=17) at diagnosis have poor survival rate (P=0.02).
Figure 38:
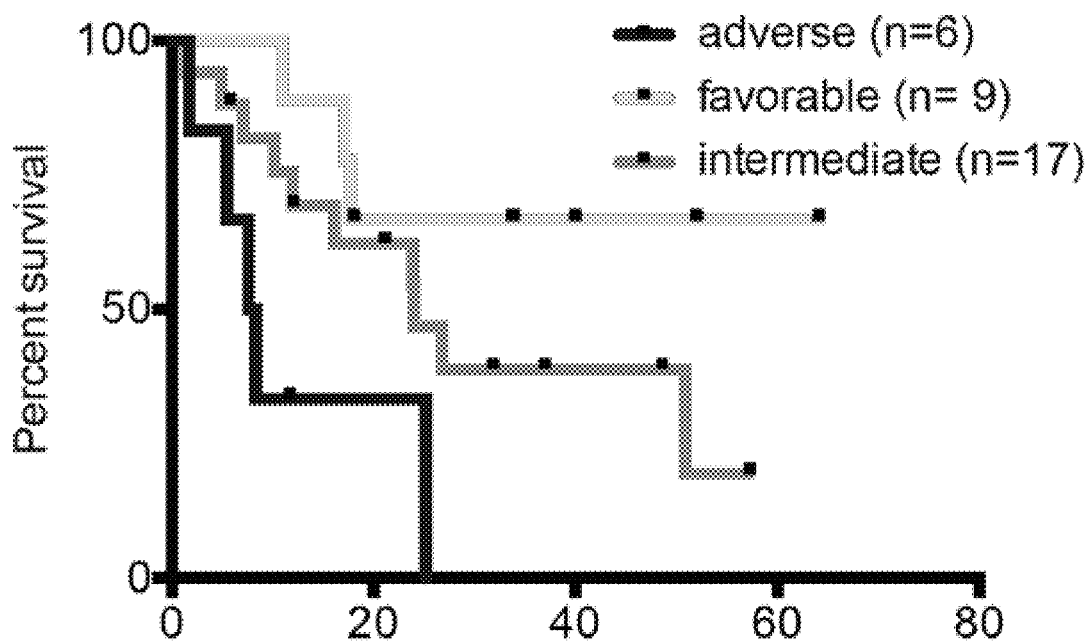
FIG. 38 depicts a Kaplan-Meier analysis showing that stratification of the local patient cohort using ELN Cytogenetic metrics divides the patients into 3 risk groups that predict survival.
Figure 39:
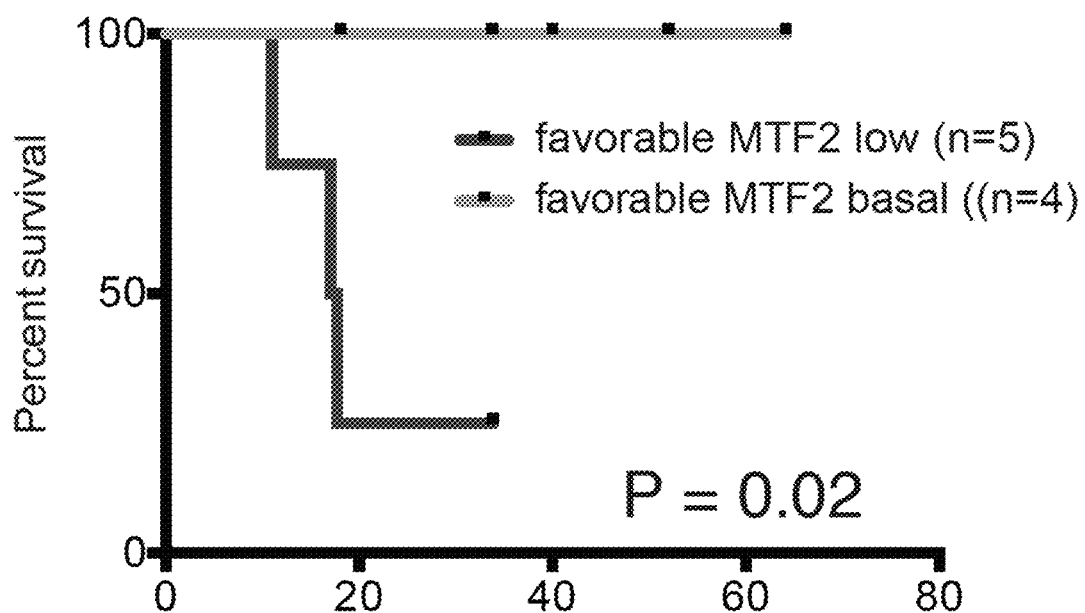
FIG. 39 depicts a Kaplan-Meier analysis of the local patient cohort showing that within the ELN favorable risk group based on cytogenetics, there was poor survival of patients with low MTF2 expression (P=0.02).
Figure 40:
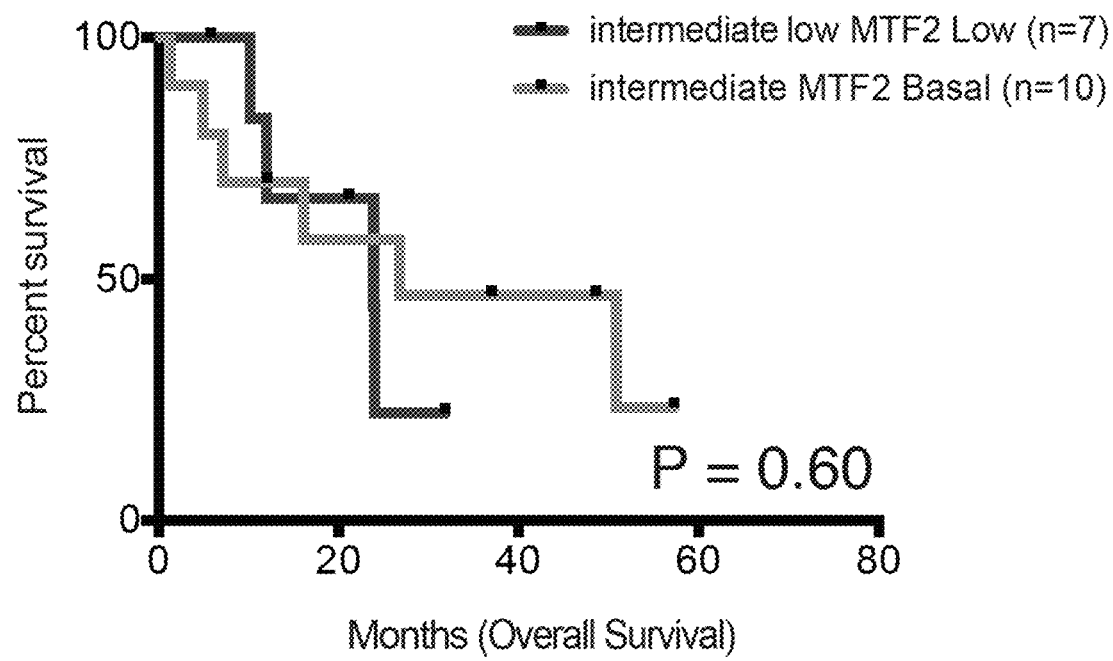
FIG. 40 depicts a Kaplan-Meier analysis of the local patient cohort showing no significant difference was observed within the intermediate risk group between patients with low or basal MTF2 expression (P=0.60).
Figure 41:
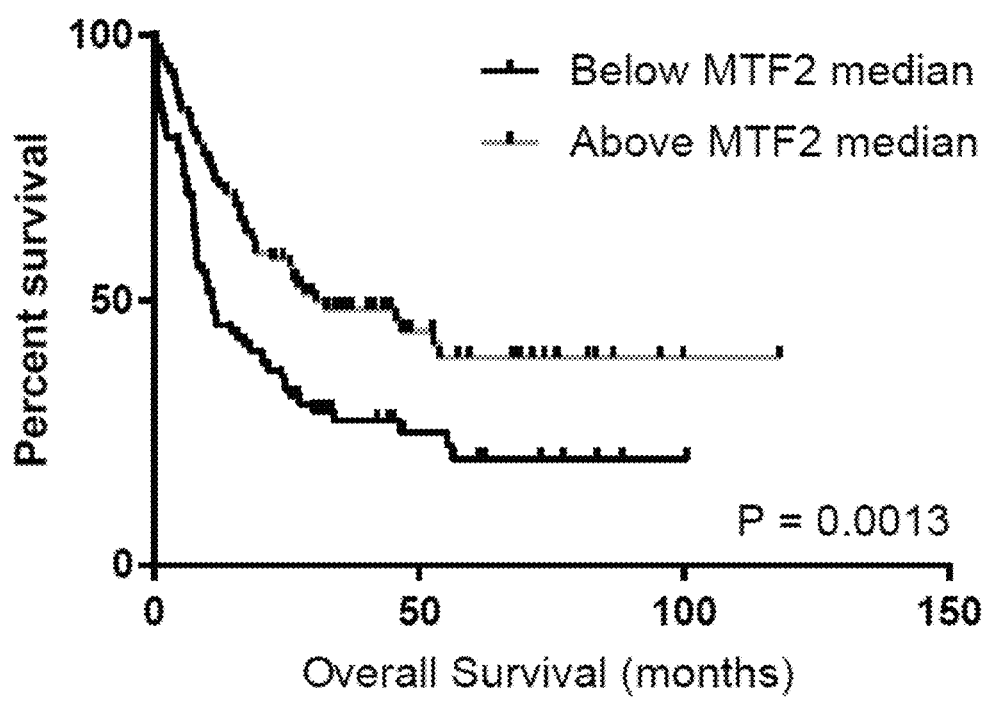
FIG. 41 shows that reduced MTF2 mRNA expression within the bulk AML bone marrow aspirates also predicts survival. Kaplan-Meier analysis was performed in patients belonging to the TCGA AML cohort (n=165) who underwent traditional 7+3 induction therapy. Patients expressing low MTF2 within the bulk AML bone marrow (n=82) at diagnosis have poor overall survival (P=0.0013). P value was calculated using Log-rank (Mantel-Cox) test.
Figure 42:
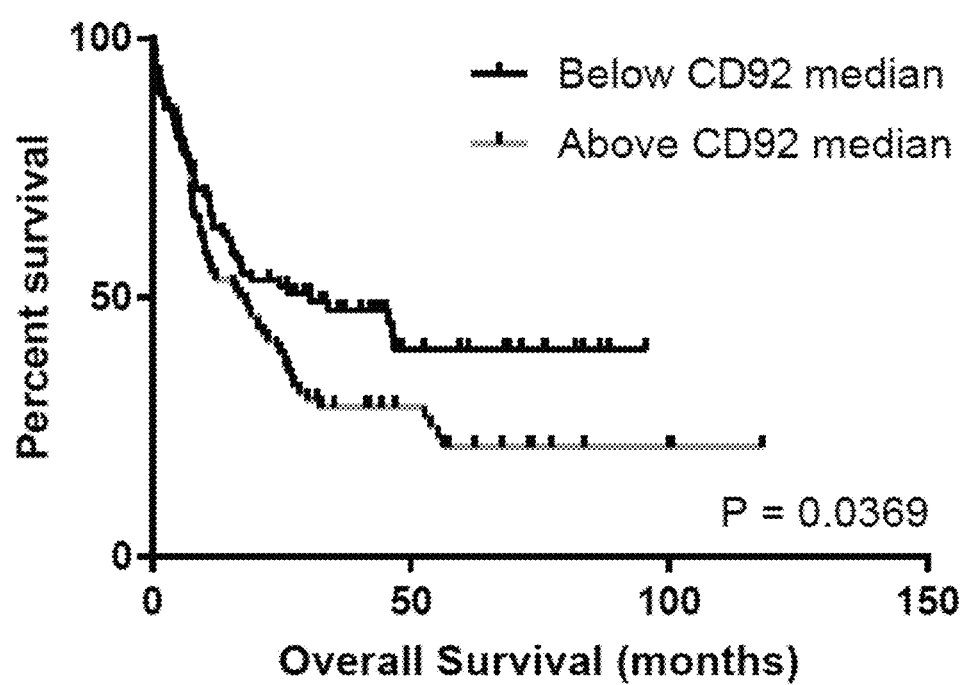
FIG. 42 presents a Kaplan-Meier analysis indicating that patients expressing high CD92 within the bulk bone marrow in the TCGA AML cohort also have poor overall survival (P=0.0369). P value was calculated using Log-rank (Mantel-Cox) test.
Figure 43:
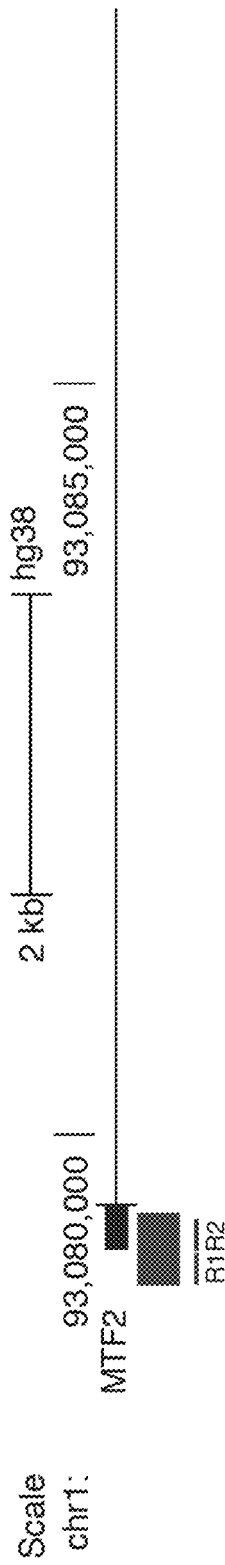
FIG. 43 shows the MTF2 gene locus, depicting the two CpG islands [R1 and R2] found within the promoter region.
Figure 44:
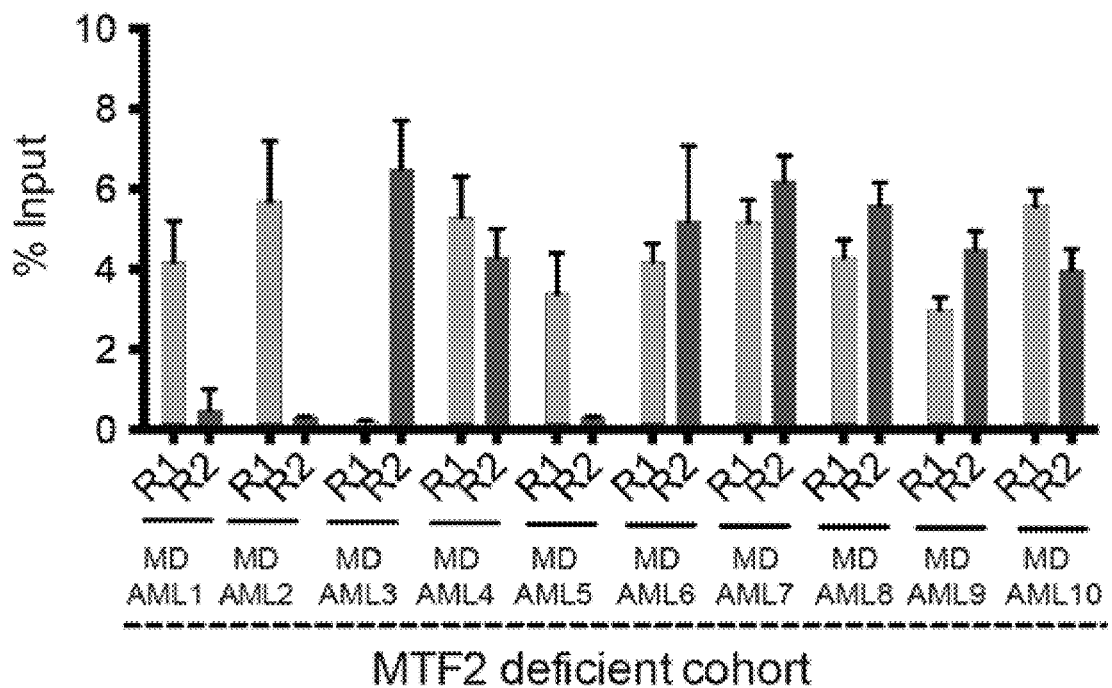
FIG. 44 shows that hypermethylation of at least one of the CpG islands is observed in MTF2 deficient AML [MD-AML].
Figure 45:
FIG. 45 shows that methylation of these islands is low in healthy BM [H-BM] sample.
Figure 46:
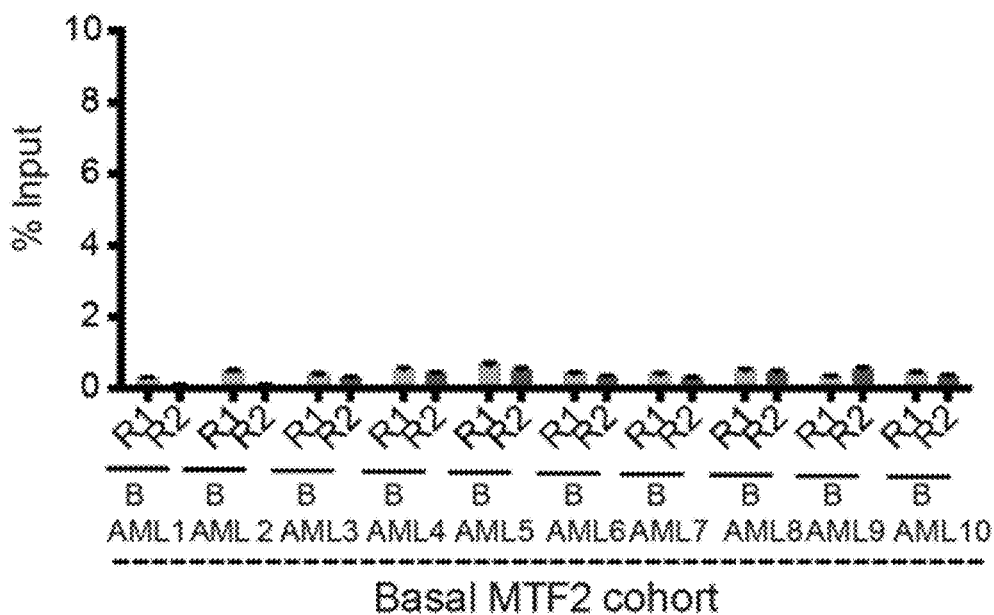
FIG. 46 shows that methylation of these islands is also low in MTF2 basal AML samples [B-AML].

Strikingly, two patient groups were identified based on total H3K27me3 levels; one with levels similar to control normal BM cells and another with markedly reduced levels. Independent clinical patient follow-up revealed that the H3K27me3-reduced LSC-enriched cohort was primarily comprised of patients failing to achieve complete remission, otherwise referred to as non-responders or refractory AML patients (FIGS. 1-2). Furthermore, reduced H3K27me3 levels within patient CD34$^+$CD38$^-$ cells predicted poor patient survival. In fact, the mean survival time of patients with normal levels of H3K27me3 was three times as long as patients with reduced H3K27me3 levels (FIG. 3, Table 2-4). Next, RT-qPCR was used to test whether there is a correlation between H3K27me3 levels and PRC2 member expression. Linear regression analysis revealed a highly significant correlation between H3K27me3 levels and MTF2 mRNA expression ($R^2$=0.9416) within the patient cohort CD34$^+$CD38$^-$ cells. However, the correlation for other PRC2 members was not as strong (FIG. 4-6). Reduced MTF2 mRNA expression within the patient CD34$^+$CD38$^-$ cells also was associated with poor response to standard induction chemotherapy (FIG. 7-8) and poor survival (FIG. 36-37). Cytogenetics analysis revealed that our cohort consisted of patients belonging to all the three European LeukemiaNet (ELN) risk categories (FIG. 38). Interestingly, even within the favorable cytogenetics category (FIG. 39), MTF2 levels were able to further stratify patients based on overall survival; although, this was not found to be the case in the intermediate cytogenetics category (FIG. 40). These results were further validated using the TCGA dataset[9], where AML patients received an induction therapy regimen identical to the treatment given to our cohort (methods). Kaplan-Meier analyses of the TCGA dataset revealed that patients with reduced levels of MTF2 and increased levels of CD92 within the bulk BM had reduced overall survival (FIG. 41-42, Table 5).

Table 5 depicts clinical characteristics of the TCGA AML cohort.

TABLE 5

| | All (n = 165) | Basal (n = 83) | Low (n = 82) |
|---|---|---|---|
| Median age (years)[range] | 58 [18-88] | 61 [22-81] | 55 [18-88] |
| WBC at diagnosis [range] | 14.3 [0.4-297.4] | 11.5 [0.5-297.4] | 18.9 [0.4-137.2] |
| Median bone marrow blast % at diagnosis [range] | 73 [30-100] | 64 [30-100] | 79.5 [30-98] |
| Cytogenetic risk* group (fav/inter/adverse) | 33/95/37 | 24/37/22 | 9/58/15 |

TABLE 5-continued

|  | All (n = 165) | Basal (n = 83) | Low (n = 82) |
|---|---|---|---|
| # alloHSCT (%) | 72 (43.6) | 42 (50.6) | 30 (36.5) |
| # deaths (%) | 104 (63) | 44 (53) | 60 (73.2) |
| Median Overall Survival (days) | 578 [28-2859] | 822 [28-2859] | 335 [30-2099] |

*Cytogenetics were defined by the TCGA research network

Figure 9:
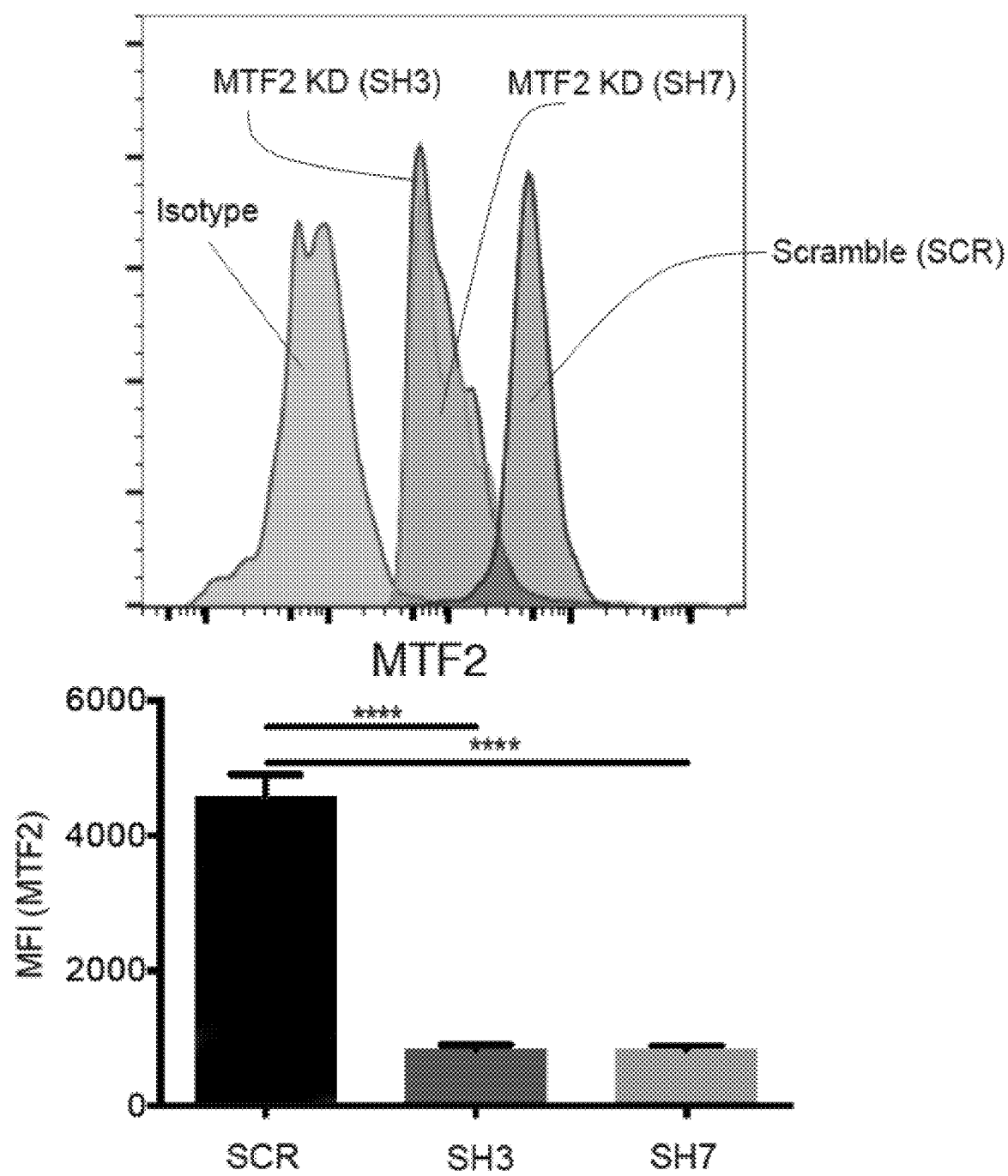
FIG. 9 depicts results shRNA scramble control (SCR) or knockdown of MTF2 (SH3 or SH7) within $CD34^+CD38^-$ HSPCs assessed by flow cytometry.
Figure 10:
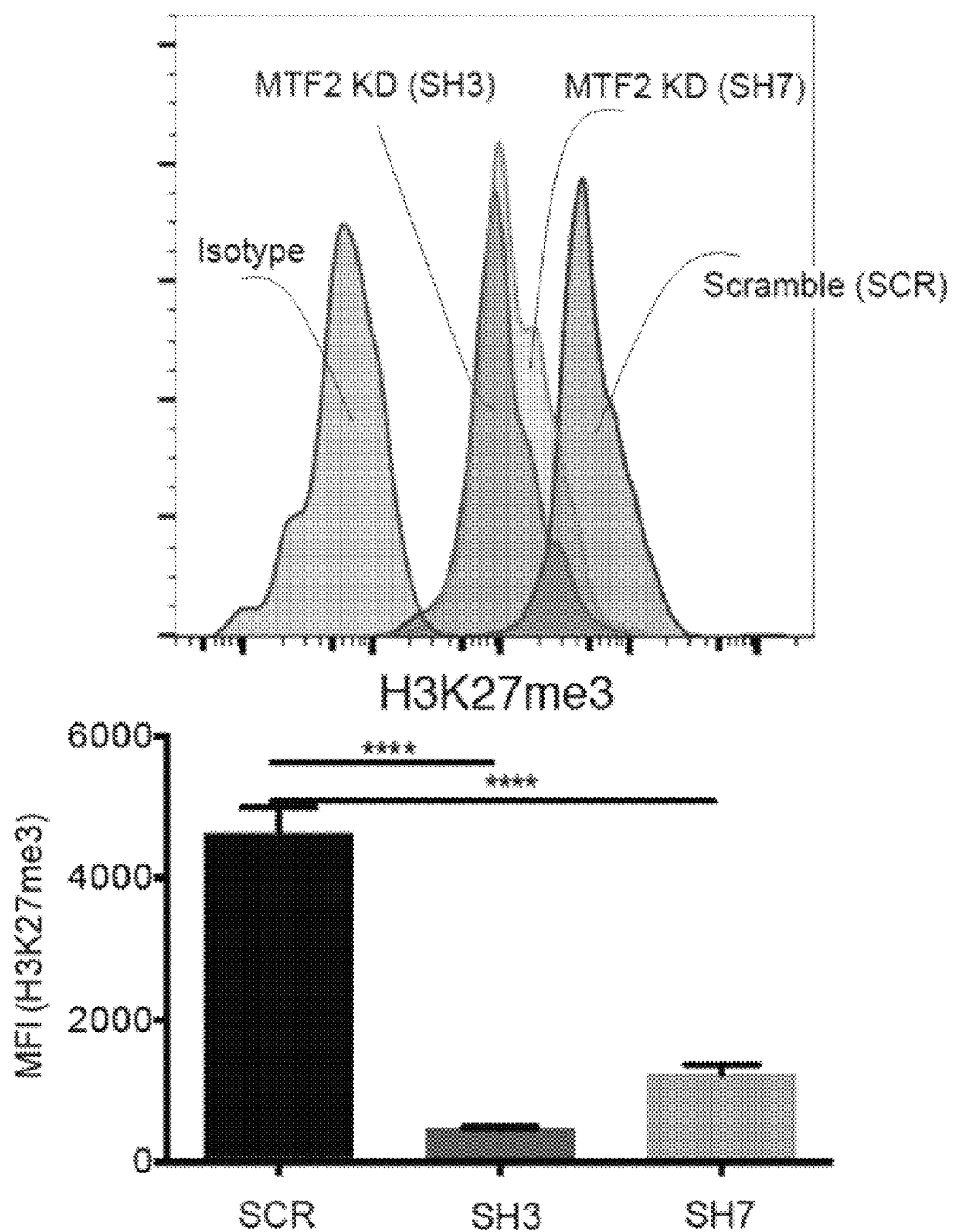
FIG. 10 shows that shRNA knockdown of MTF2 (SH3 or SH7) decreases H3K27me3 levels, assessed by flow cytometry.
Figure 47:
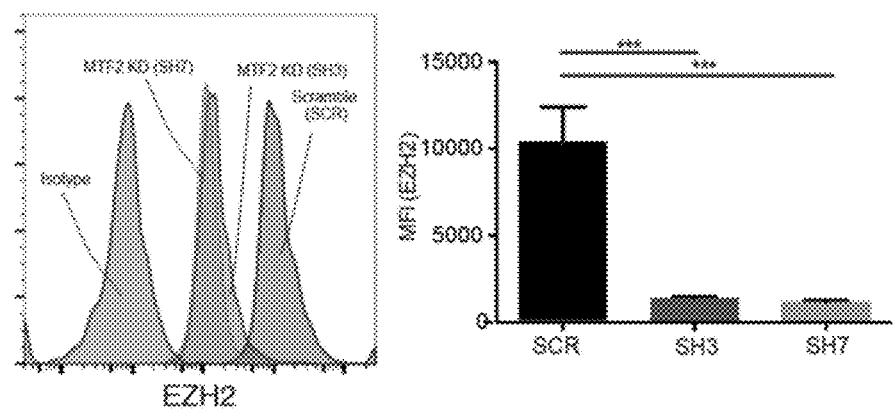
FIG. 47 shows that knockdown of MTF2 with two independent shRNA clones (SH3 or SH7) within CD34$^+$CD38$^-$ hematopoietic stem and progenitor cells results in decreased core PRC2 members EZH2 and SUZ12 measured by flow cytometric analysis.
Figure 47:
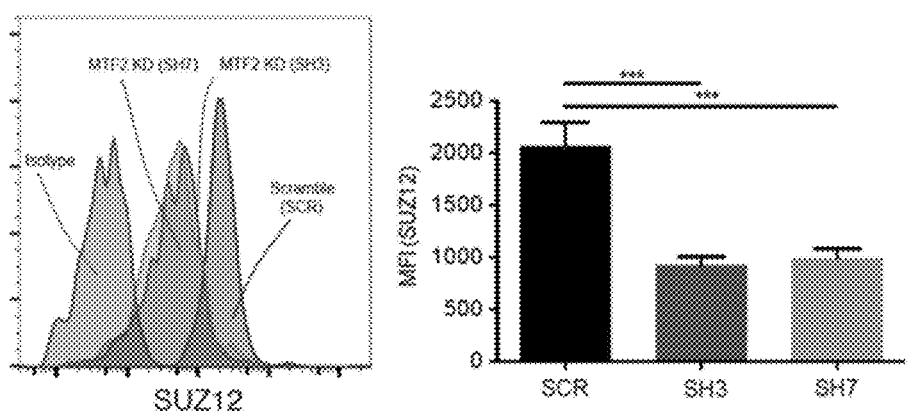
Figure 48:
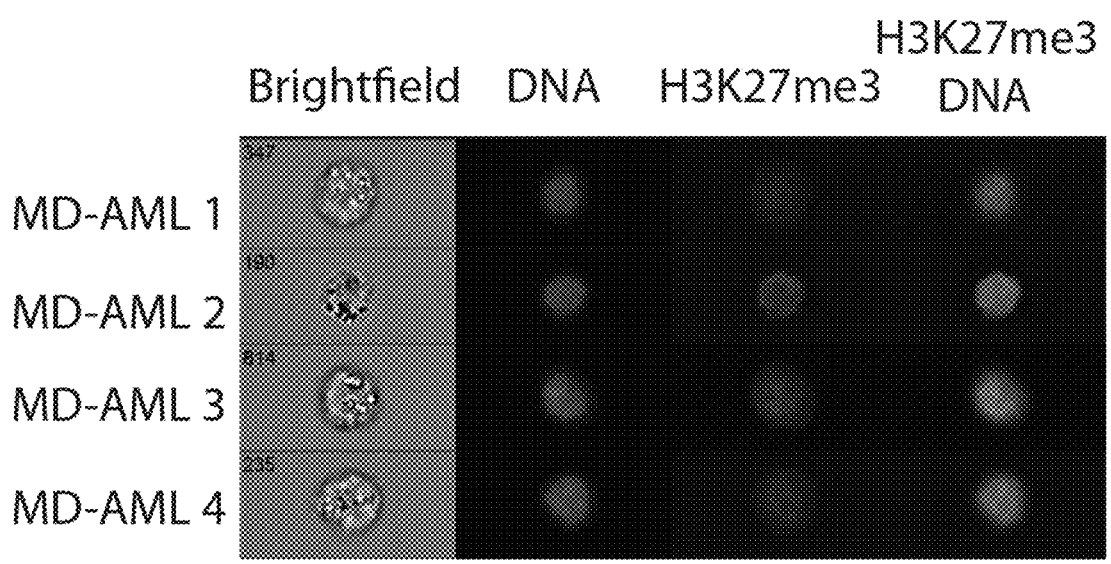
FIG. 48 shows that CD34$^+$CD38$^-$ cell samples from 4 different AML patients with MTF2 deficiency [MD-AML 1-4] analyzed by imaging flow cytometry show low levels of H3K27me3 at diagnosis. Expression levels of H3K27me3 were assessed by measuring the mean fluorescence intensity (MFI) within the nucleus by a preset algorithm in the IDEAS software (Amnis).
Figure 49:
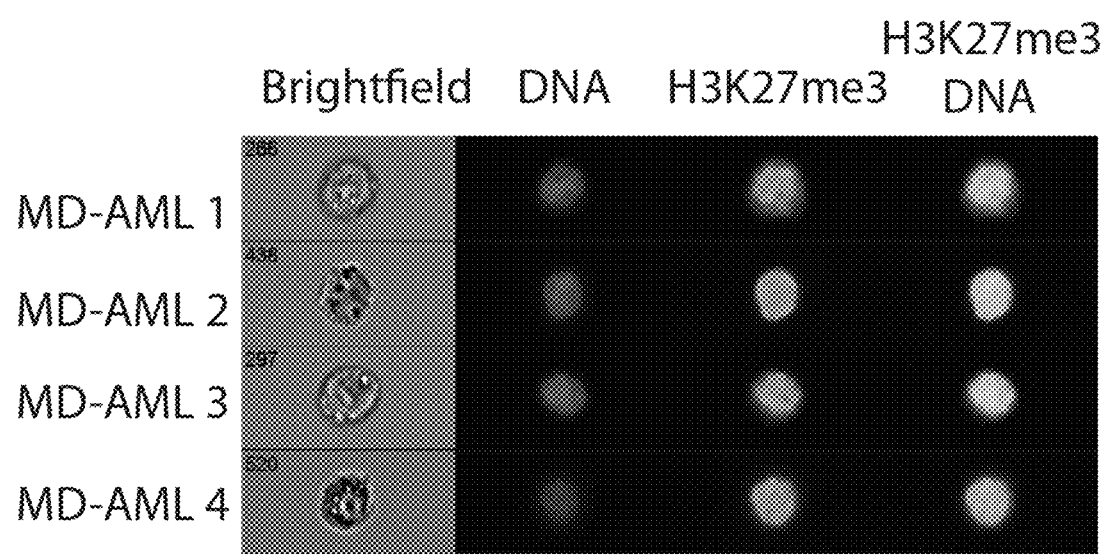
FIG. 49 shows that H3K27me3 expression is re-established in 4 AML patient CD34$^+$CD38$^-$ samples with MTF2 deficiency when MTF2 levels are rescued by lentivirus-mediated overexpression. Expression levels of H3K27me3 were assessed by measuring the mean fluorescence intensity (MFI) within the nucleus by a preset algorithm in the IDEAS software (Amnis).
Figure 50:
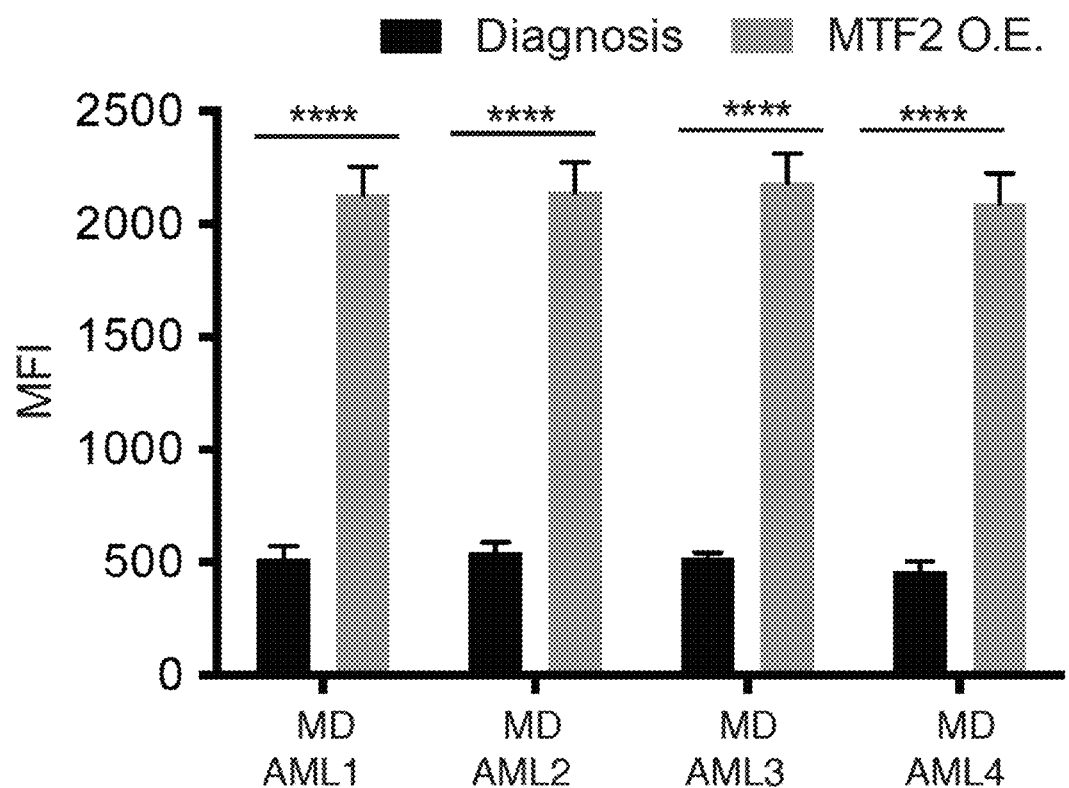
FIG. 50 also shows that H3K27me3 levels are re-established 4 AML patient CD34$^+$CD38$^-$ samples with MTF2 deficiency when MTF2 levels are rescued by lentivirus-mediated overexpression.
Figure 51:
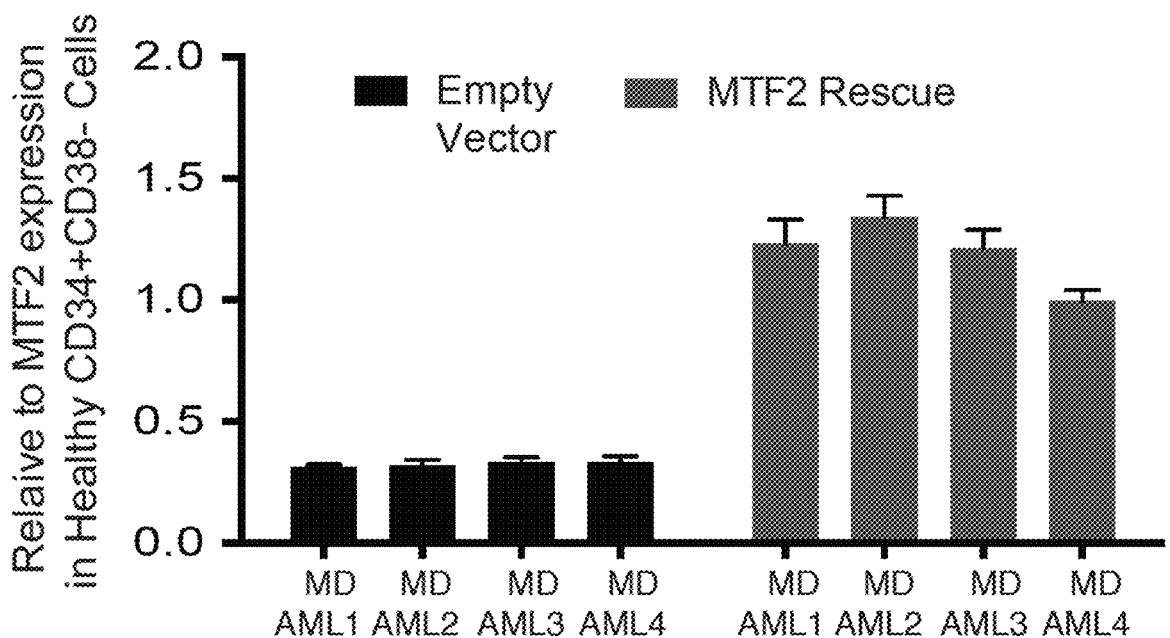
FIG. 51 depicts RT-qPCR validation of MTF2 expression in rescued MD-AML patient CD34$^+$CD38$^-$ samples.
Figure 52:
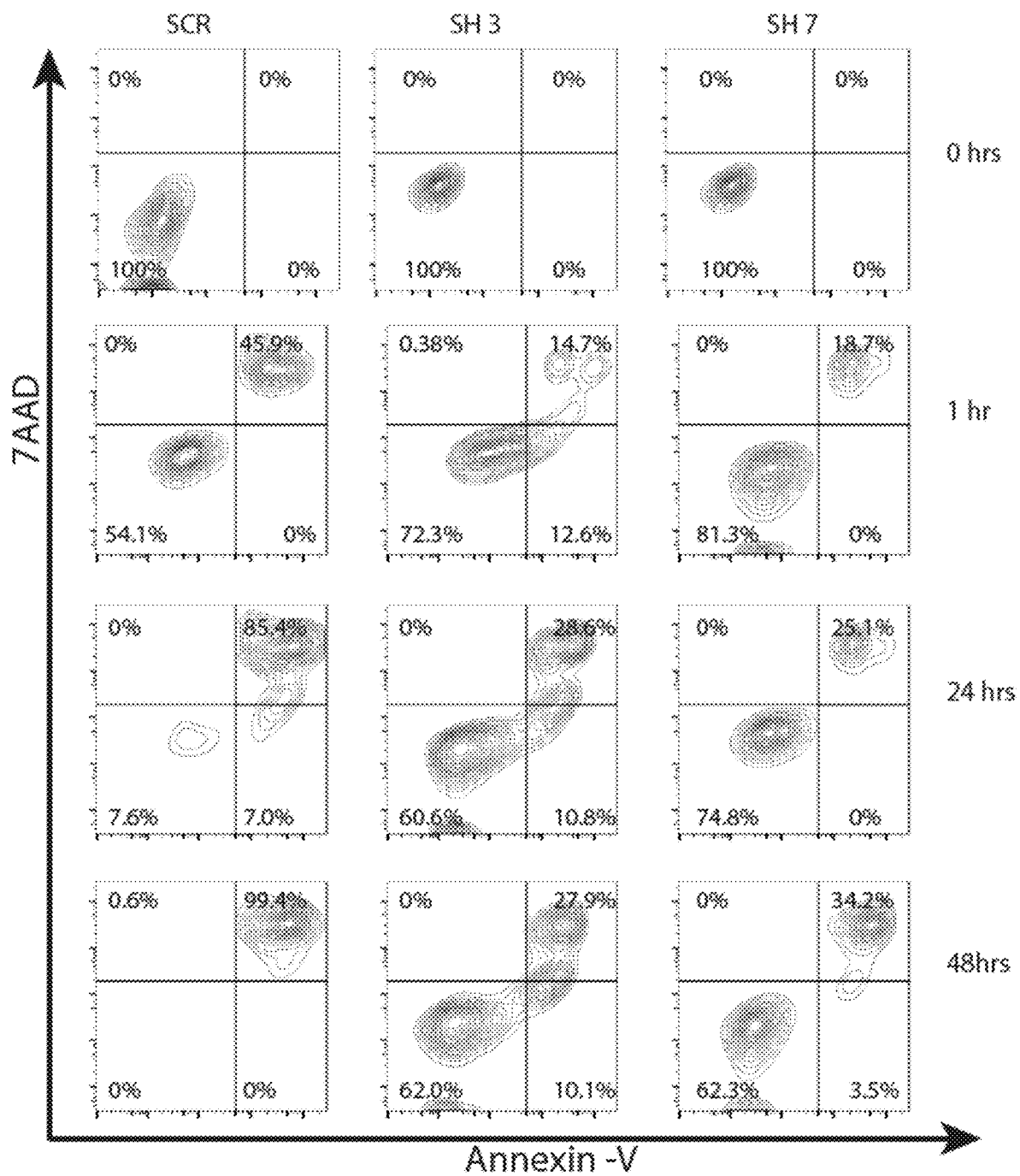
FIG. 52 shows results of experiments in which cord blood Lin$^-$CD34$^+$ cells were transduced with GFP-tagged lentivirus encoding Scramble (SCR) or MTF2 (SH3, SH7) shRNA. Viable GFP$^+$ transduced cells were sorted and treated with induction drugs. Flow cytometry plots measuring apoptotic cells treated with 0.5 μM Daunorubicin are shown.
Figure 53:
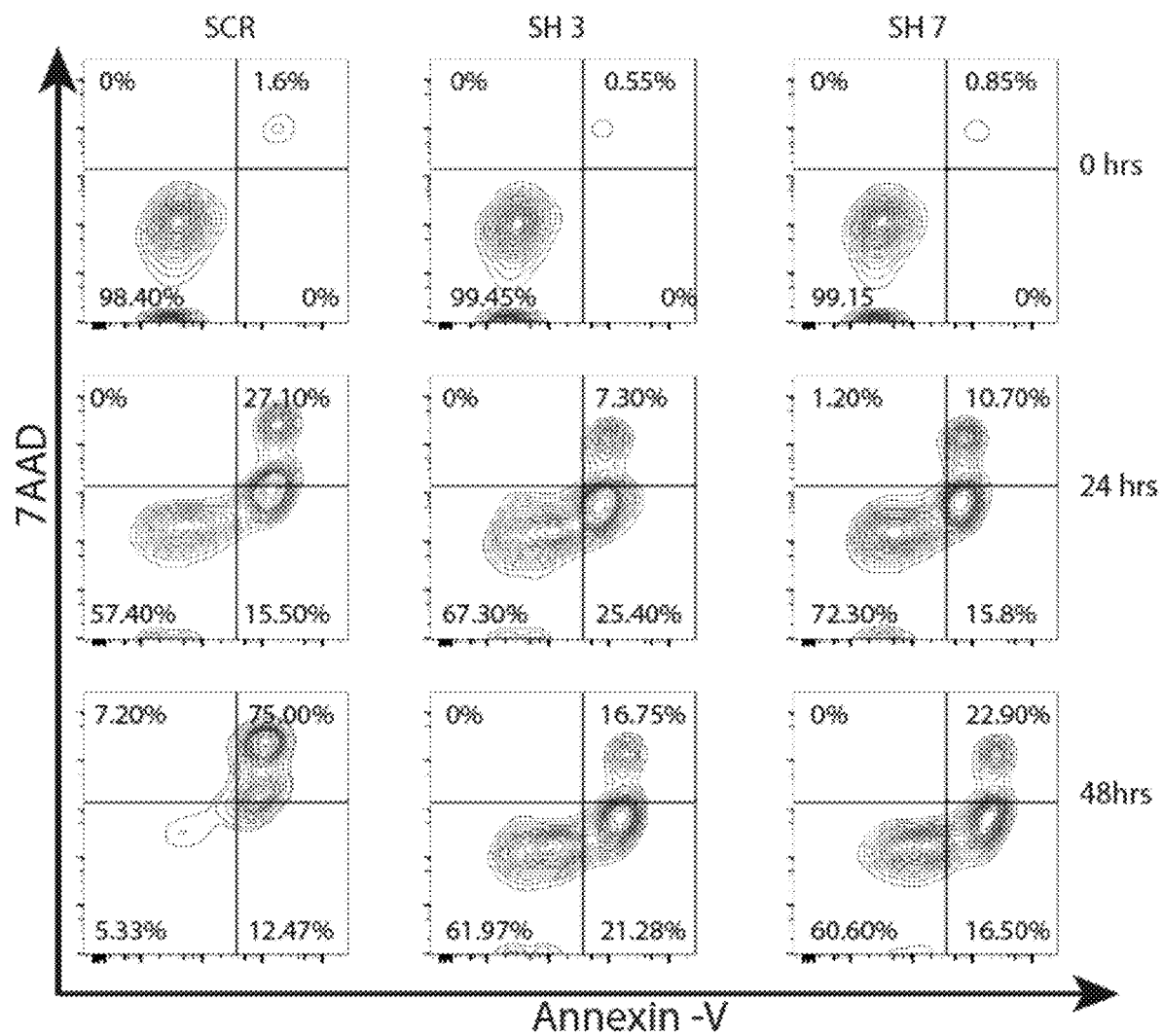
FIG. 53 depicts flow cytometry plots measuring apoptotic Lin$^-$CD34$^+$ cells treated with 1 μM Cytarabine. Viable cells were determined at different time points by the percent of Annexin V-negative/7-AAD-negative cells, while early-apoptotic cells were measured by the percentage of the Annexin V-positive/7-AAD-negative cells. Percentage of late apoptotic, dead cells was obtained by the positive dual staining of Annexin V-positive/7-AAD-positive.
Figure 54:
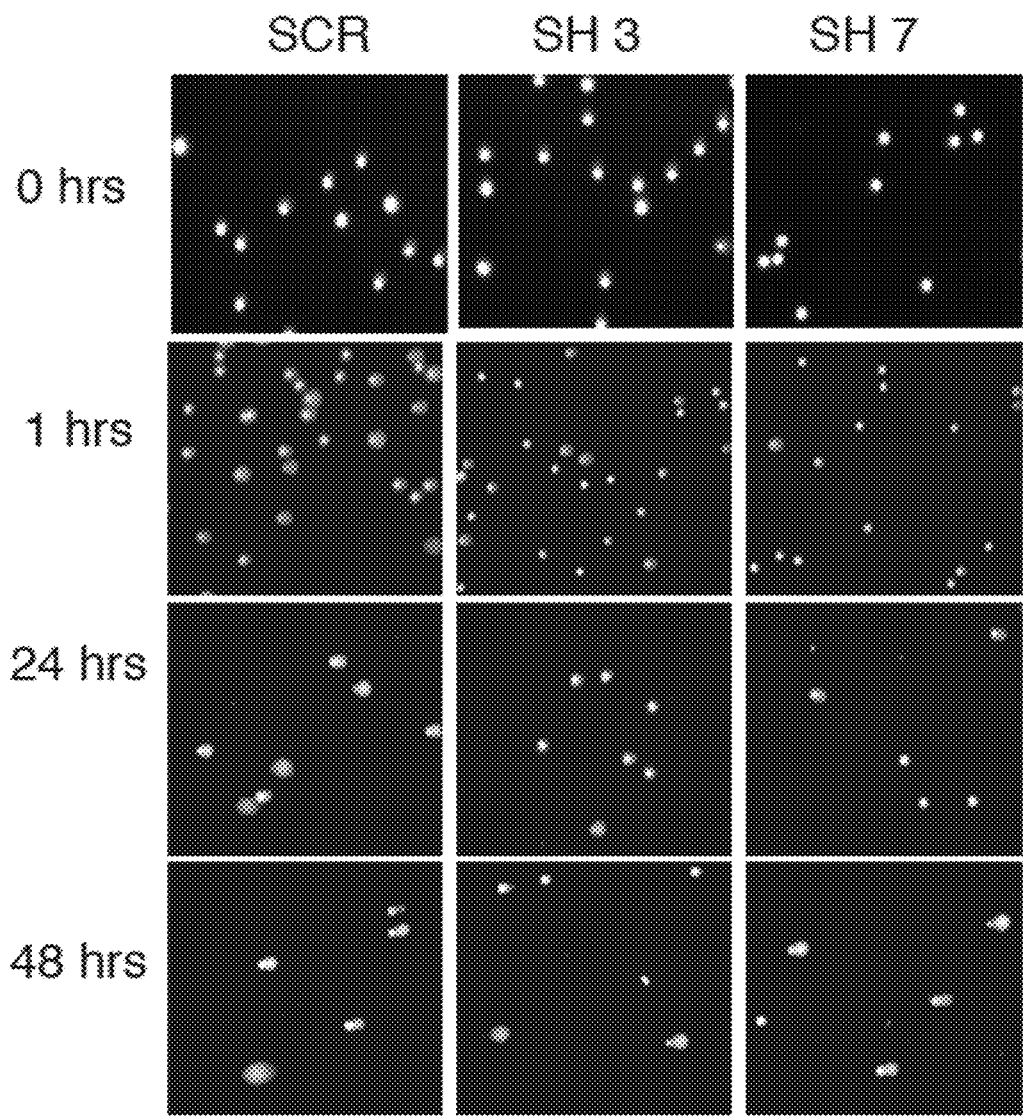
FIG. 54 shows representative comet images depicting damage accumulation within CD34$^+$CD38$^-$ HSPCs transduced with scramble control (SCR) or MTF2 knockdown (SH3 or SH7) shRNA post-treatment with 0.5 μM Daunorubicin.
Figure 55:
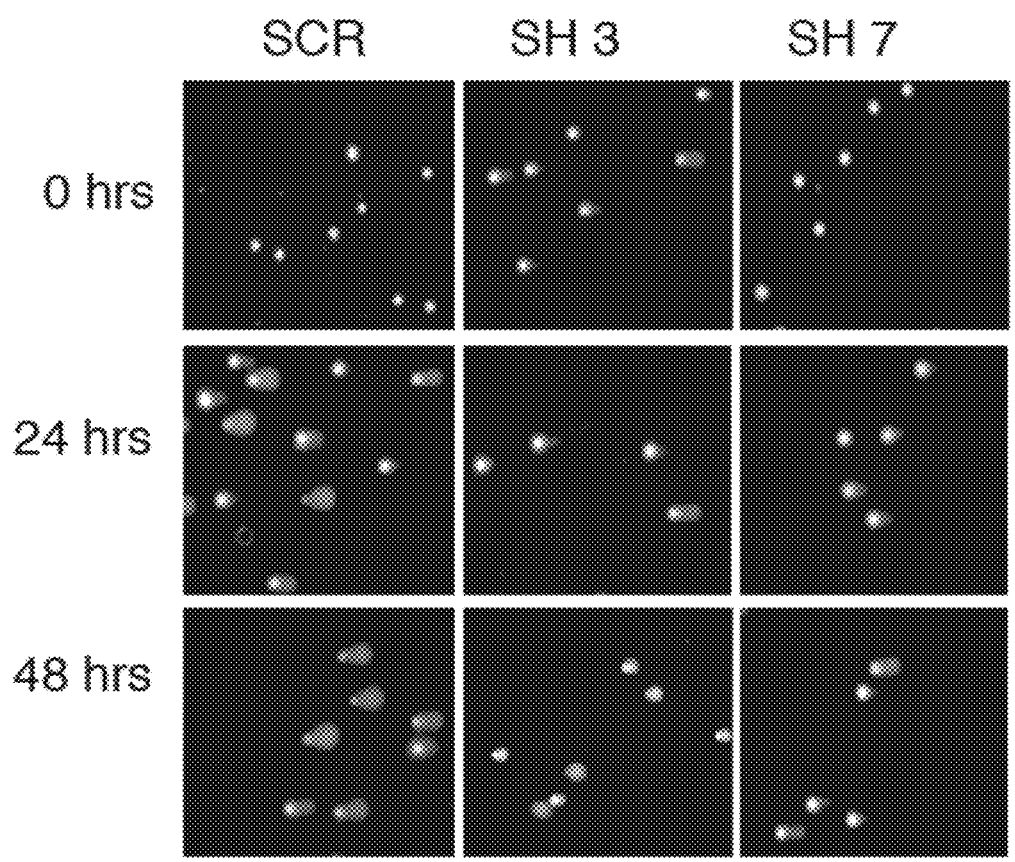
FIG. 55 shows representative comet images depicting damage accumulation within CD34$^+$CD38$^-$ HSPCs transduced with scramble control (SCR) or MTF2 knockdown (SH3 or SH7) shRNA post-treatment with 1 μM Cytarabine. With time, an increase in comet-like nuclei indicating an accumulation of damaged DNA is observed over 48 hours. Blinded analysis of >200 comets were scored per condition and time point using a comet assay ImageJ OpenComet application.
Figure 56:
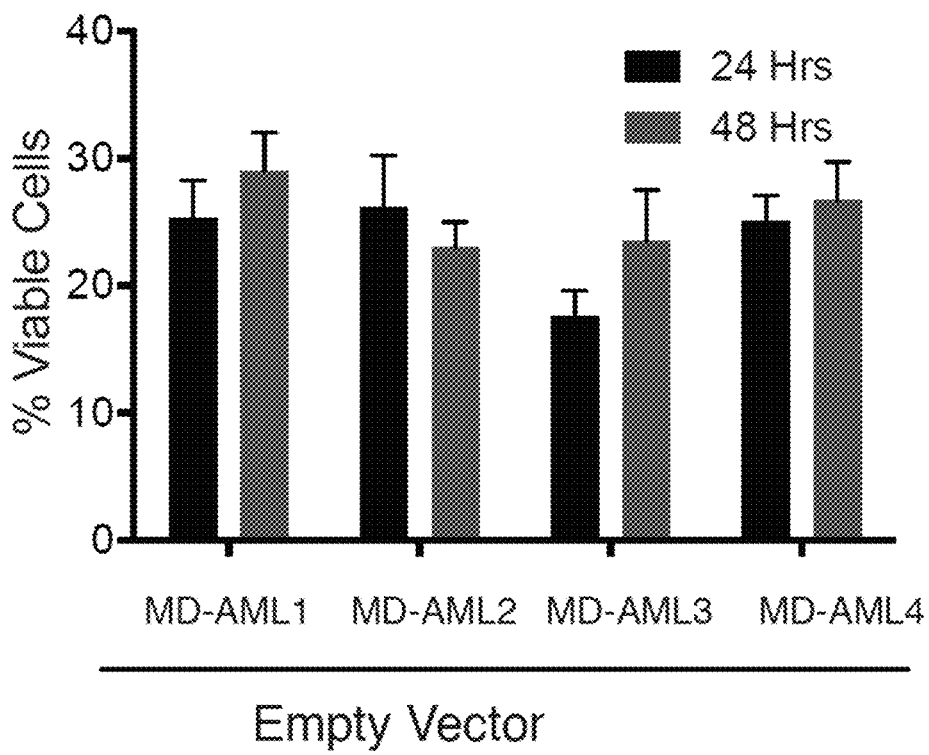
FIG. 56 shows that a subpopulation of CD34$^+$CD38$^-$ cells from AML patients with MTF2 deficiency [MD-AML] treated with 0.5 μM Daunorubicin remain viable over 48 hours.
Figure 57:
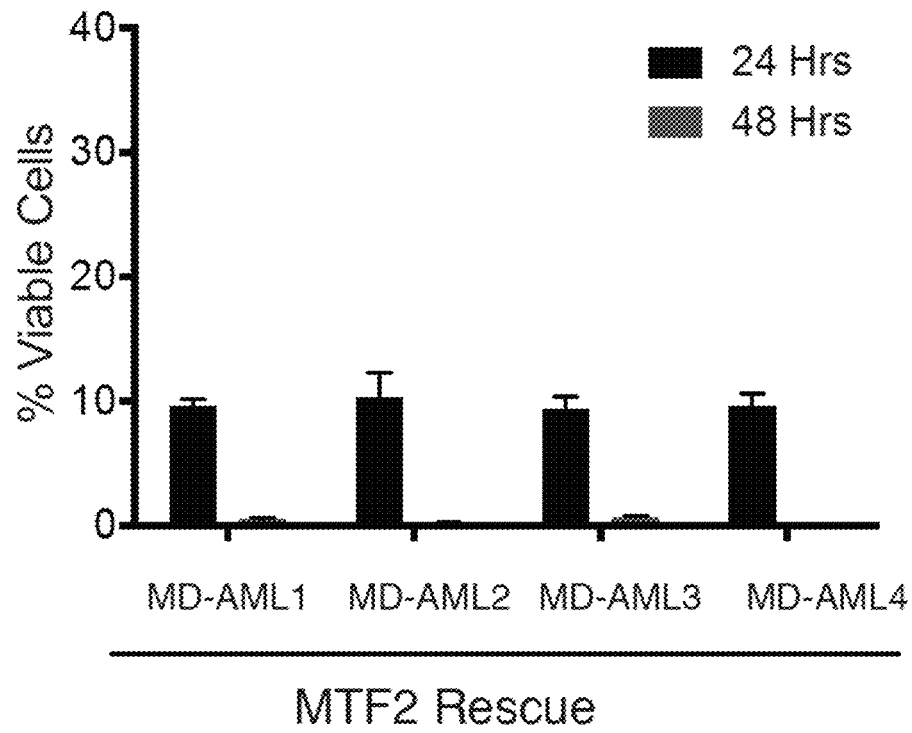
FIG. 57 shows restoration of MTF2 in MD-AML patient CD34$^+$CD38$^-$ cells via lentiviral-induced expression sensitized the cells to Daunorubicin.
Figure 58:
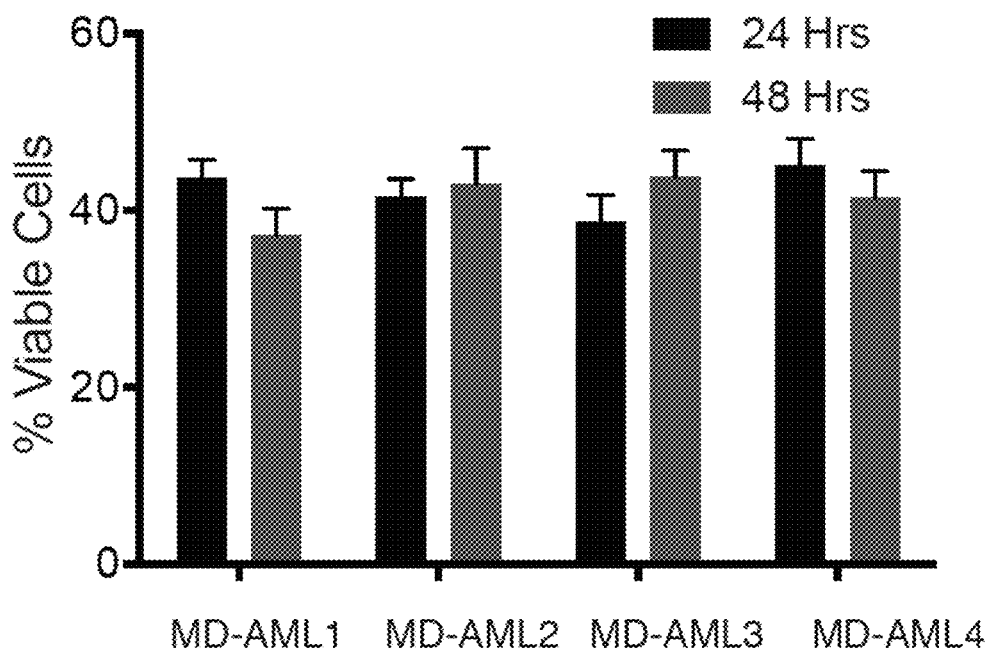
FIG. 58 shows that a subpopulation of CD34$^+$CD38$^-$ cells isolated from MTF2 deficient AML (MD-AML) patient bone marrow treated with 1 μM Cytarabine remain viable over 48 hours.
Figure 59:
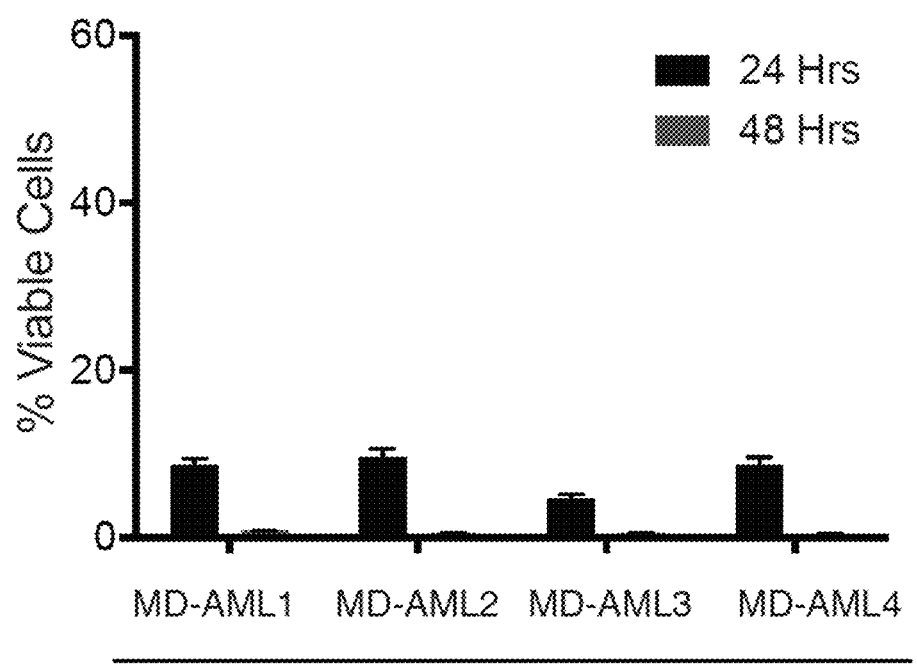
FIG. 59 shows that MTF2 restoration in CD34$^+$CD38$^-$ cells isolated from MTF2 deficient AML (MD-AML) patient bone marrow abolished the chemoresistance to Cytarabine when observed within 48 hours post-treatment. Cells were analyzed by flow cytometry using viability and apoptosis markers 7AAD and Annexin V.

Considering MTF2 is rarely mutated in AML, the MTF2 promoter was analyzed for evidence of hypermethylation and it was discovered that at least one of the two CpG islands in the MTF2 promoter was hypermethylated in all MTF2-deficient AML samples, while neither CpG island is methylated in healthy BM (H-BM) or AML samples with normal (basal) MTF2 levels (B-AML) (FIGS. 43 to 46). The close correlation between MTF2 expression and H3K27me3 levels led to testing of whether downregulation of MTF2 is sufficient to reduce H3K27me3 levels. Thus, umbilical cord-derived CD34$^+$CD38$^-$ cells were transduced with 2 different MTF2 shRNA GFP-encoded lentiviruses. Flow cytometry analysis of H3K37me3 levels in GFP$^+$ cells revealed markedly reduced H3K27me3 within 96 hours of MTF2 knockdown (FIG. 9-10). Further investigation showed reduced SUZ12 and EZH2 levels by MTF2 knockdown (FIG. 47), suggesting that reduced MTF2 impacts PRC2 levels resulting in decreased H3K27me3. In contrast, ectopic expression of MTF2 in MTF2-deficient CD34$^+$CD38$^-$ leukemic cells rescued MTF2 expression and re-established global H3K27me3 levels (FIG. 48-50), further demonstrating that MTF2 proportionately dictates H3K27me3 levels.

Figure 11:
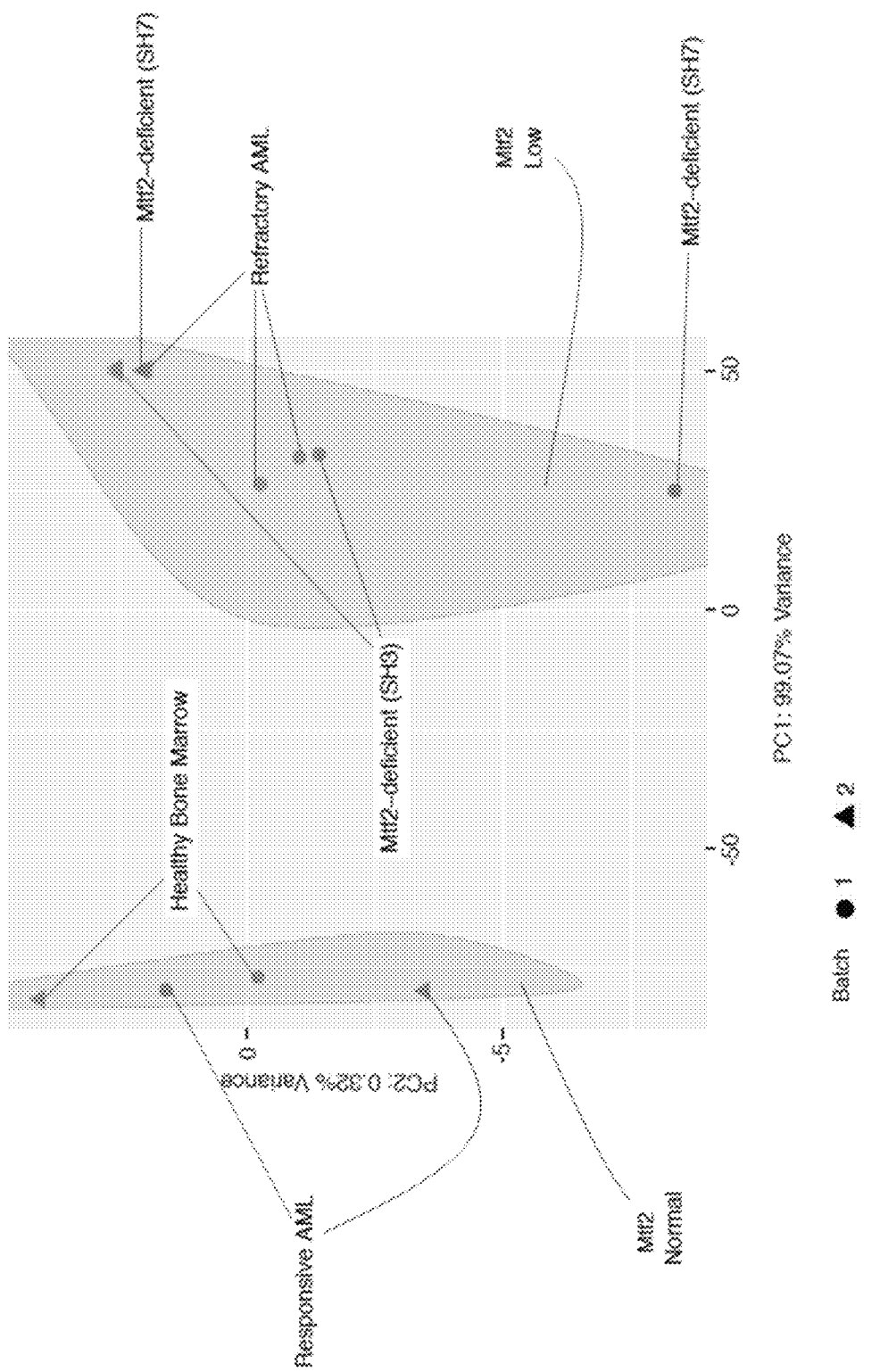
FIG. 11 shows principal component analysis of spike-in normalized H3K27me3 ChIP-seq data from $CD34^+CD38^-$ BM cells isolated from refractory AML patients (n=4 samples), responsive AML patients (n=2 samples) or healthy BM transduced with MTF2 (n=4 samples) or scramble (n=2 samples) shRNA. The H3K27me3 ChIP sequencing was performed in 2 independent batches (batch 1=●, batch 2=▲).
Figure 12:
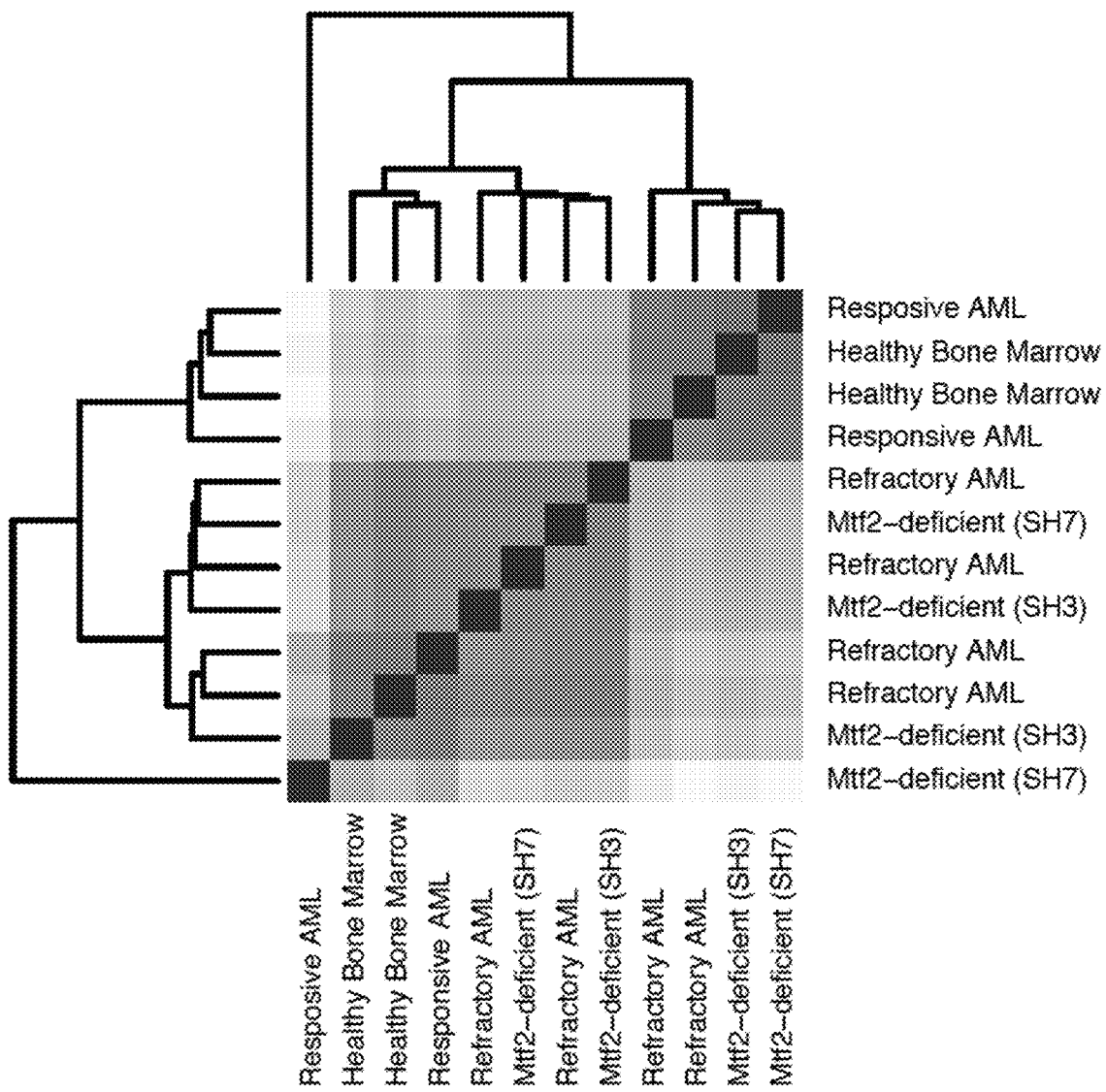
FIG. 12 depicts hierarchical clustering analysis, which demonstrated that the MTF2 deficient $CD34^+CD38^-$ BM population clusters closely to the $CD34^+CD38^-$ population isolated from refractory AML BM aspirates.
Figure 13:
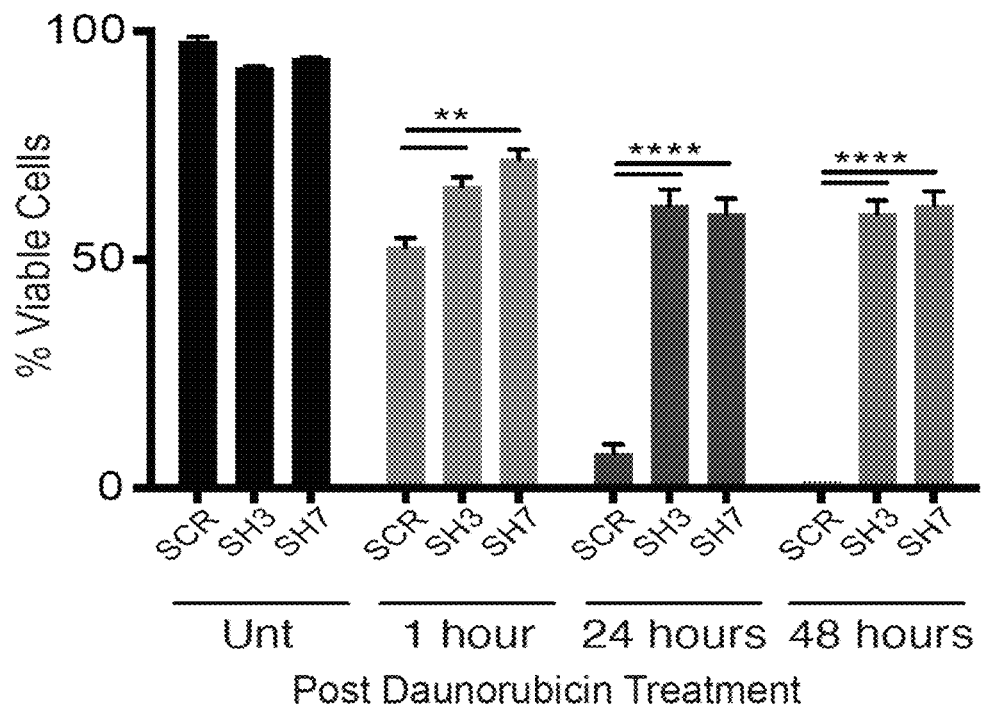
FIG. 13 depicts result of viability and apoptosis assessments of scramble control cells (SCR) and MTF2 shRNA knockdown (SH3 or SH7) $Lin^-CD34^+$ HSPCs assessed over a 48-hour time period post-treatment with Daunorubicin. Viable cells were determined by the percent of Annexin V-negative/7-AAD-negative cells.
Figure 14:
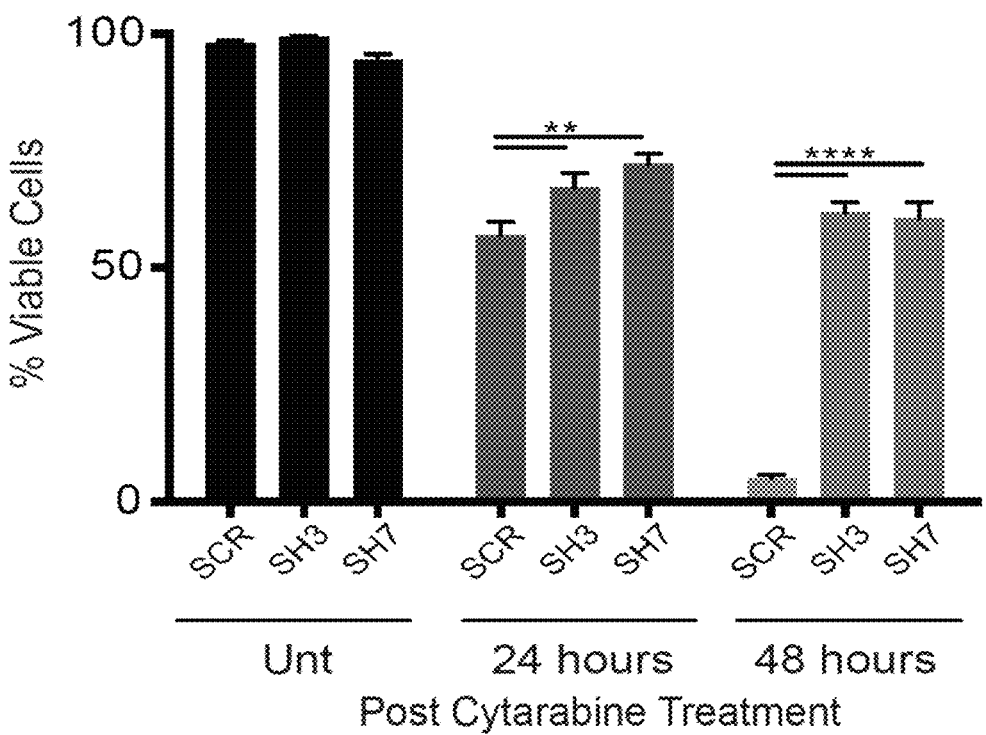
FIG. 14 depicts results of viability and apoptosis assessments of scramble control cells (SCR) and MTF2 shRNA knockdown (SH3 or SH7) Lin⁻CD34⁺ HSPCs assessed over a 48-hour time period post-treatment with Cytarabine. Viable cells were determined by the percent of Annexin V-negative/7-AAD-negative cells.

Next, chromatin immunoprecipitation-sequencing (ChIP-seq) was used to investigate the changes in H3K27me3 levels triggered by MTF2 deficiency. To aid in relative H3K27me3 quantification across samples, *Drosophila* chromatin spike-in controls were added to the samples and H3K27me3 signal was normalized to the *Drosophila* chromatin spike-in. Principal component analysis (PCA) of H3K27me3 revealed that MTF2-knockdown CD34$^+$CD38$^-$ BM cells cluster close to refractory patient CD34$^+$CD38$^-$ cells, while healthy CD34$^+$CD38$^-$ BM cells cluster with CD34$^+$CD38$^-$ BM cells from induction therapy-responsive patients (FIG. 11-12). Taken together, these results demonstrate that MTF2 deficiency and reduced H3K27me3 levels within LSC-enriched CD34$^+$CD38$^-$ cells correlate with refractory AML. Moreover, MTF2 deficiency within healthy CD34$^+$CD38$^-$ cells triggers an H3K27me3 landscape that is similar to that found within refractory LSCs.

Figure 15:
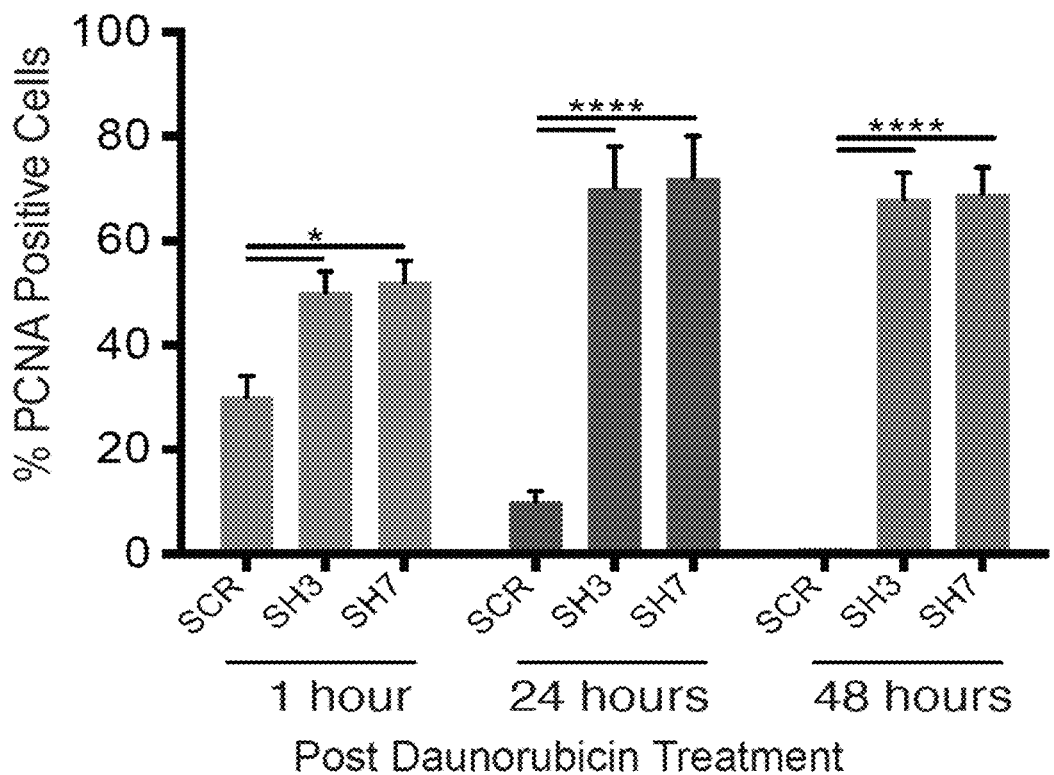
FIG. 15 depicts PCNA proliferation marker analysis of scramble control (SCR) and MTF2 shRNA knockdown (SH3, SH7) Lin⁻CD34⁺ HSPCs 48 hours post-Daunorubicin.
Figure 16:
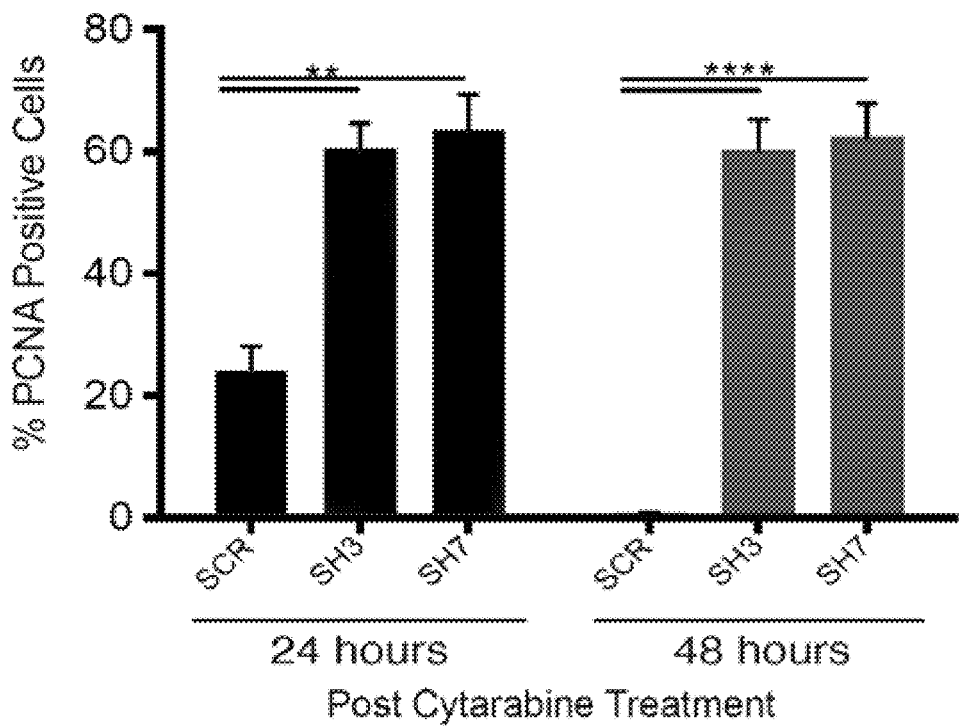
FIG. 16 depicts PCNA proliferation marker analysis of scramble control (SCR) and MTF2 shRNA knockdown (SH3, SH7) Lin⁻CD34⁺ HSPCs 48 hours post-Cytarabine.
Figure 17:
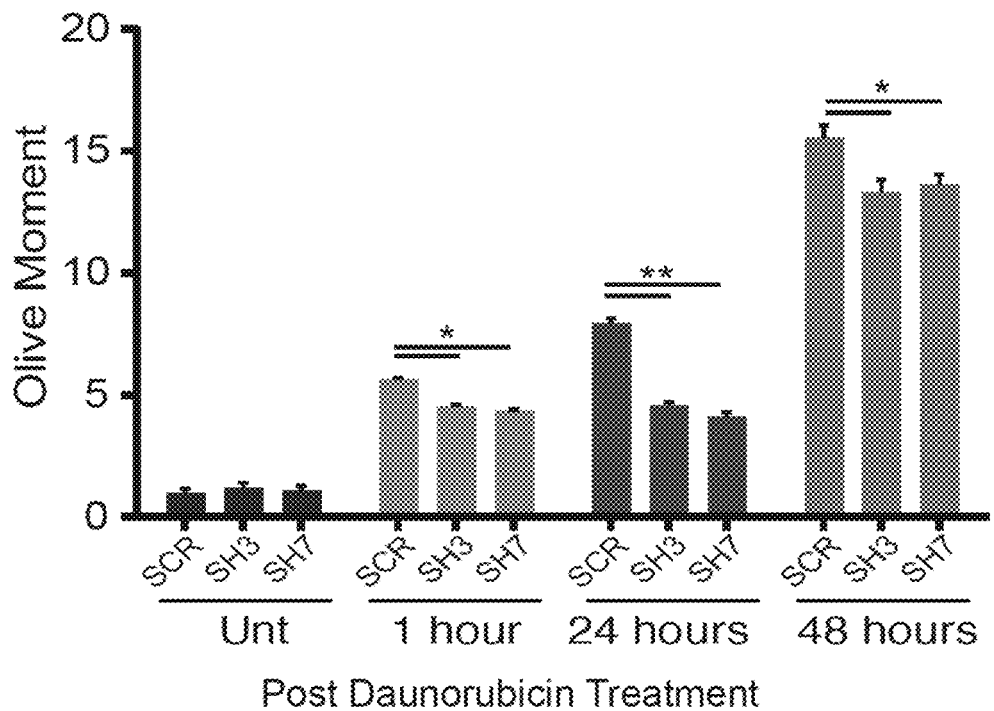
FIG. 17 shows DNA damage accumulation in scramble control (SCR) and MTF2 shRNA knockdown (SH3, SH7) Lin⁻CD34⁺ HSPCs post-induction treatment with Daunorubicin over 48 hours via the alkaline comet assay.
Figure 18:
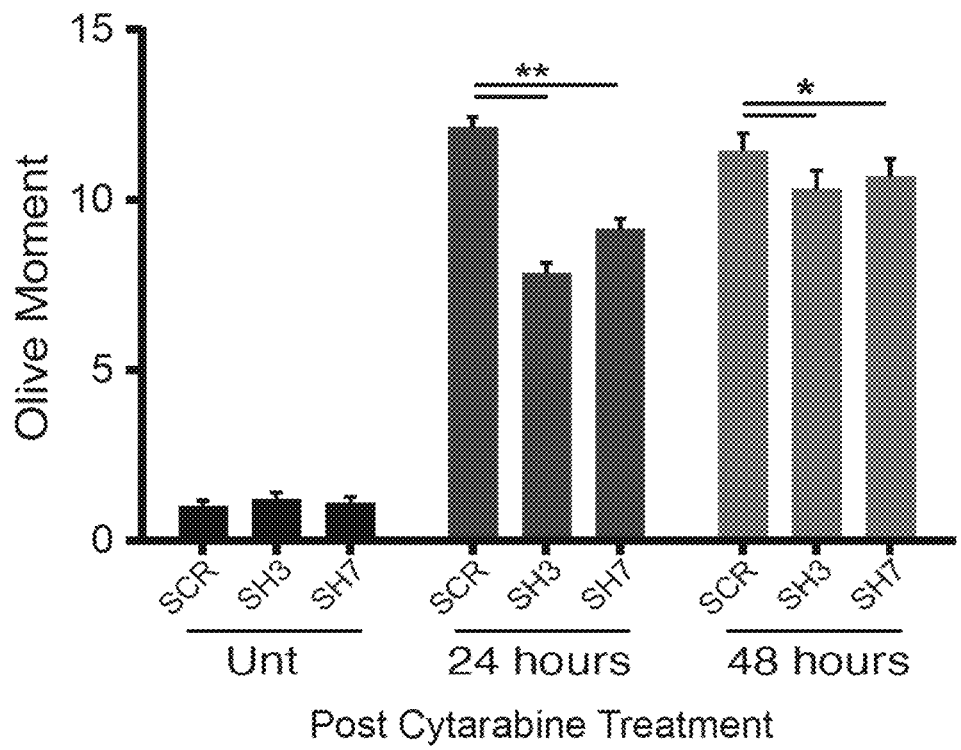
FIG. 18 shows DNA damage accumulation in scramble control (SCR) and MTF2 shRNA knockdown (SH3, SH7) Lin⁻CD34⁺ HSPCs post-induction treatment with Cytarabine assessed over 48 hours via the alkaline comet assay.

To test whether MTF2 deficiency confers resistance to standard induction therapy, hematopoietic stem and progenitor cells (HSPCs) were transduced with MTF2 shRNA GFP-tagged lentiviruses. GFP$^+$ viable cells were sorted 72-hours post-transduction, then treated with the induction therapy drugs Daunorubicin or Cytarabine. 48 hours later, less than 6% of the scramble shRNA control cells survived, while more than 60% of MTF2-deficient cells were viable (FIG. 13-14, FIG. 52-53). Furthermore, nearly two-thirds of the viable MTF2-deficient cells were PCNA$^+$, demonstrating that MTF2-deficient cells continue to proliferate despite chemotherapy treatment (FIG. 15-16). Considering both Daunorubicin and Cytarabine target proliferating cells by inducing DNA damage[10-12], DNA damage accumulation was examined in scramble and MTF2 shRNA transduced cells over a 48-hour period during which the samples were treated with either Daunorubicin or Cytarabine. DNA damage accumulation was assessed using the alkaline comet assay, where the Olive moment was measured using a blinded analysis[13]. Across all time points, the highest levels of DNA damage were found in the scramble control HSPCs (FIG. 17-18, FIG. 27-28, FIG. 54-55). Furthermore, rescuing MTF2 expression in CD34$^+$CD38$^-$ cells from refractory, MTF2 deficient AML cells (MD-AML) by lentivirus-induced MTF2 expression sensitized the cells to Daunorubicin and Cytarabine (FIG. 56-59). Thus, MTF2 deficiency confers a refractory phenotype since MTF2-deficient HSPCs are resistant to standard induction chemotherapy drugs and replicate despite DNA damage.

Figure 19:
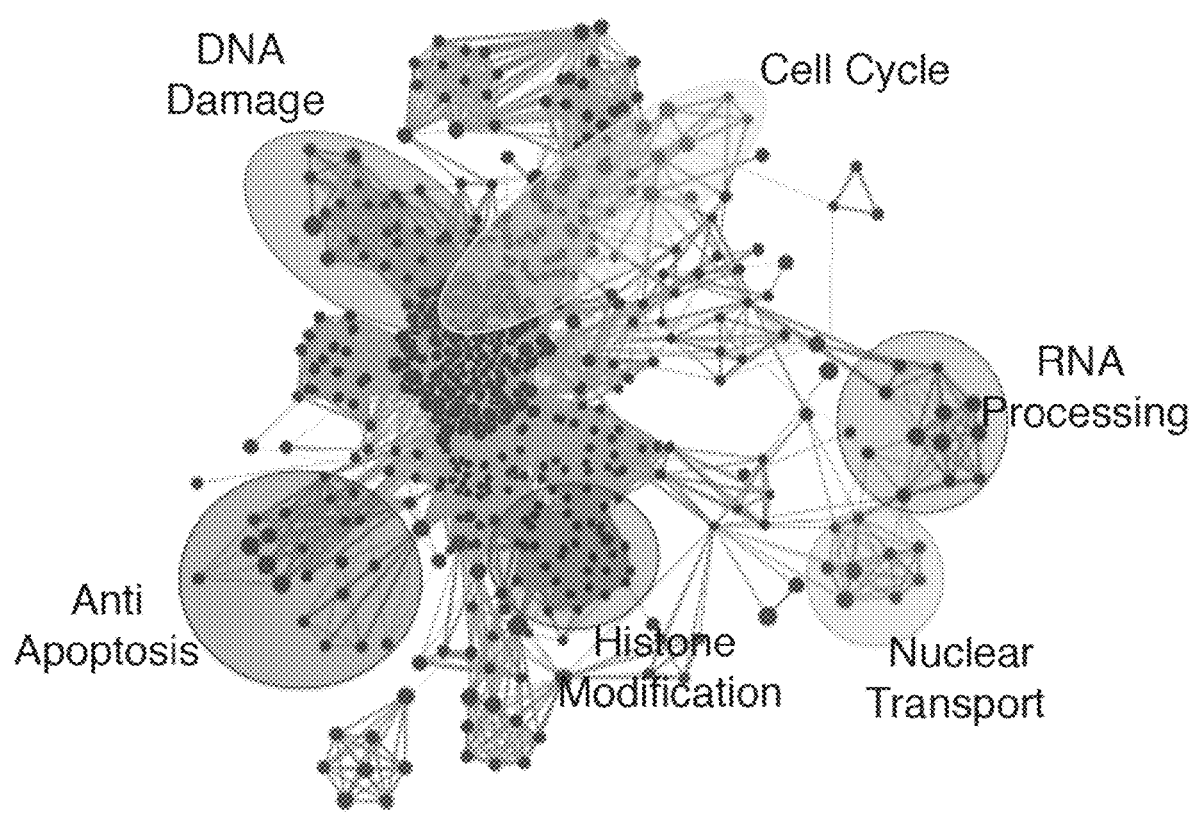
FIG. 19 depicts the results of gene ontology enrichment analysis of MTF2-deficient HSPCs RNAseq data that identified genes misregulated in processes such as cell cycle, RNA processing, nuclear transport, anti-apoptosis, histone modifications and DNA damage response (DDR).
Figure 20:
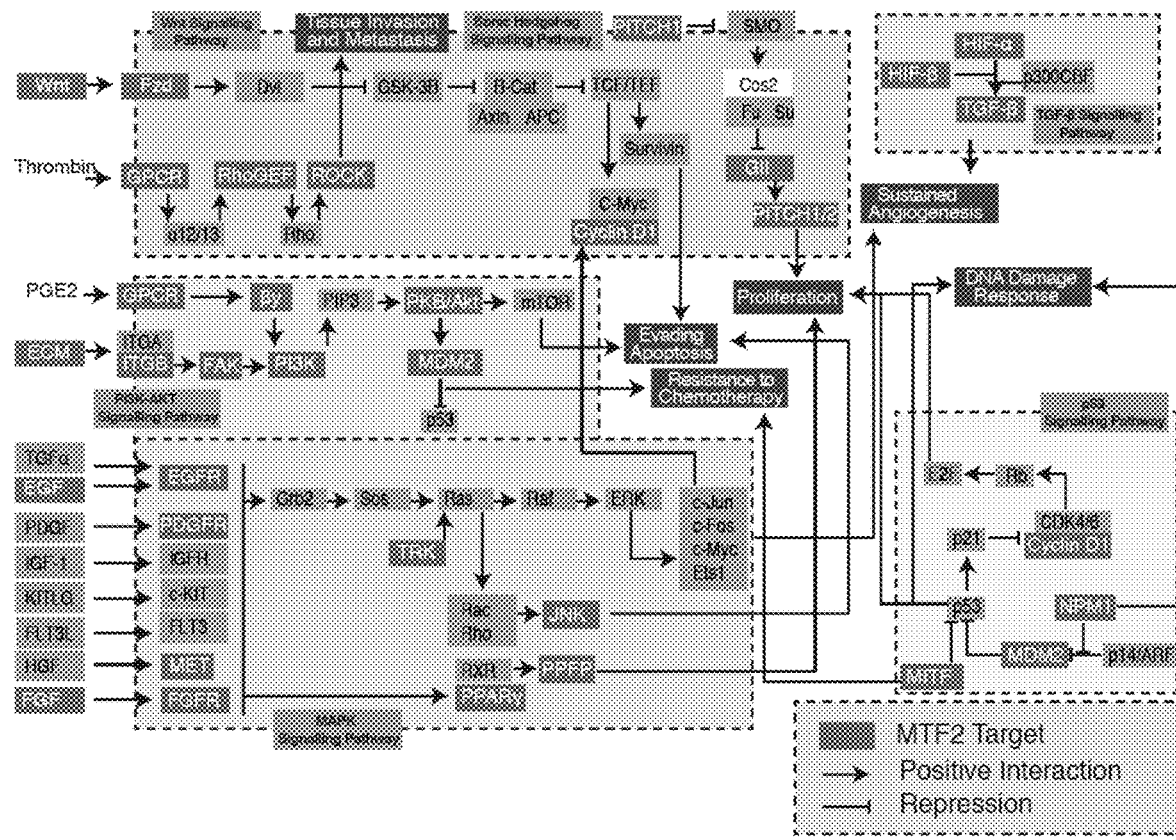
FIG. 20 depicts KEGG-pathway analysis of the MTF2-PRC2 gene regulatory network (GRN) from integrated RNA-seq and H3K27me3 ChIP-seq data in human HSPCs uncovered oncogenic pathways that are directly regulated by MTF2-PRC2.
Figure 60:
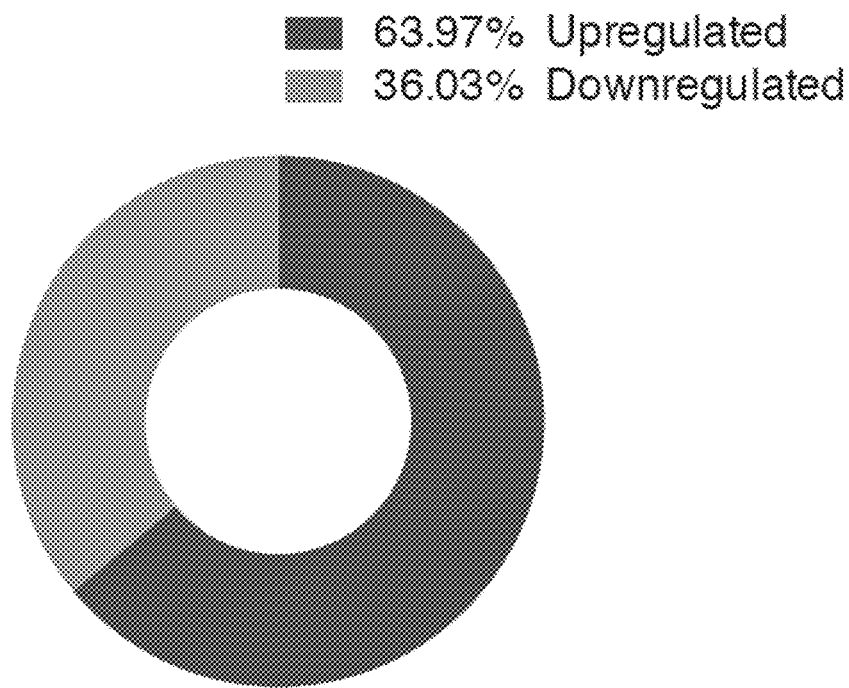
FIG. 60 shows that dissection of the DDR enrichment term from FIG. 19 revealed an upregulation in 63.97% (190 out of 297) of the genes associated with this GO term.
Figure 61:
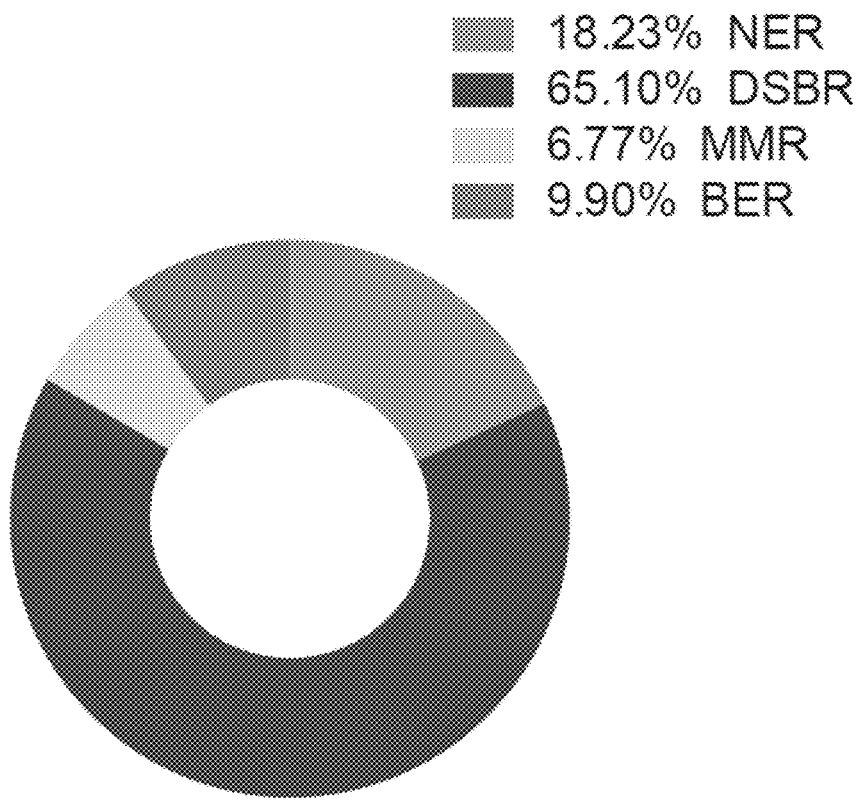
FIG. 61 shows further analysis of the upregulated DDR genes, revealing their role in Nucleotide Excision repair [NER] (35 genes), Double stranded break repair [DSBR] (123 genes), Mismatch Repair [MMR] (13 genes), and Base Excision Repair [BER] (19 genes).
Figure 93:
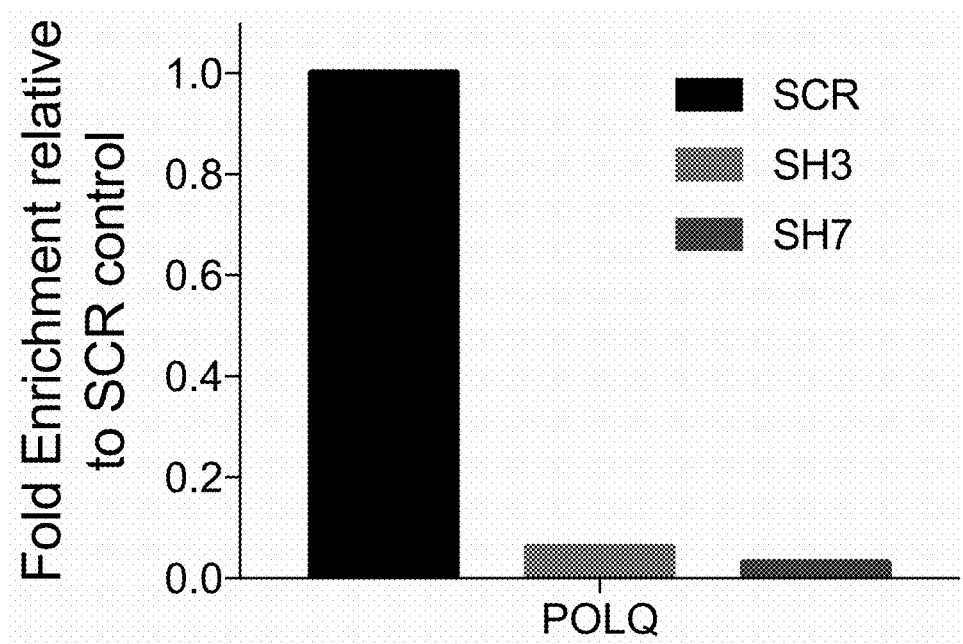
FIG. 93 shows ChIP-qPCR on MTF2 target POLQ gene.
Figure 94:
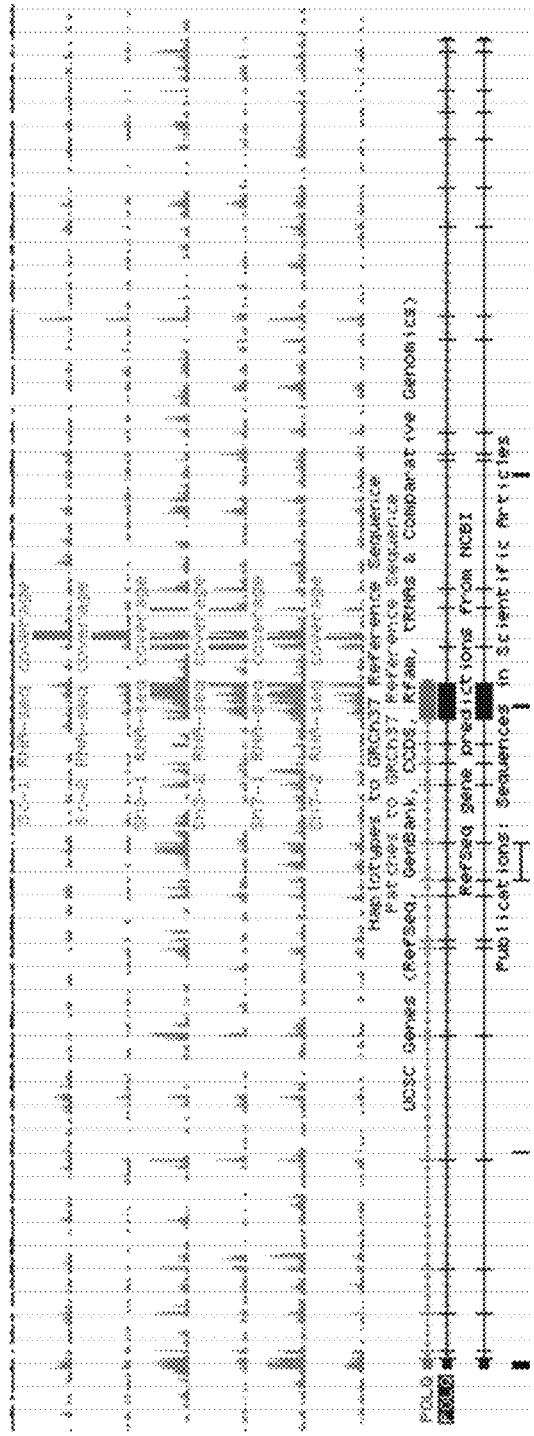
FIG. 94 shows RNA-seq traces displaying that decreased expression of MTF2 (shRNA knockdown) leads to upregulation of PolQ Polymerase, showing track hubs of the scrambled control shRNA in cord blood hematopoietic progenitors (hubs 1 &2), shRNA3 targetting MTF2 (hubs 3 &4) and shRNA7 targeting MTF2 (hubs 5 & 6), where increased peak height in tracks 3-6 confirm increased PolQ mRNA.

To understand the differences in DNA damage and uncover the molecular mechanisms underlying the poor therapeutic response in MTF2 deficient cells, MTF2 was knocked down in HSPCs by lentiviral transduction and RNA-seq was performed. Enrichment map analysis of the transcriptomic data revealed DNA damage response (DDR), anti-apoptosis and cell cycle pathways were affected (FIG. 19). Further dissection of the affected DDR transcripts showed numerous genes belonging to various DNA repair pathways were upregulated within the MTF2-deficient HSPCs compared to the scramble control, consistent with the reduced DNA damage observed in the MTF2-deficient HSPCs following induction treatment (FIG. 60-61). To identify targets of the MTF2-PRC2 complex, H3K27me3 ChIP-seq was performed. Overlaying our MTF2 knockdown transcriptomic and ChIP-seq data, a MTF2-PRC2 gene regulatory network (GRN) was drafted in human HSPCs, which revealed the oncogenic pathways repressed by MTF2 included the PI3 kinase and p53 pathways that regulate cell cycle, apoptosis, DDR and chemoresistance (FIG. 20). Some of the MTF2 targets were validated by RT-qPCR and ChIP-qPCR (FIG. 62-63), including POLQ (FIG. 93), which was also validated by RNA-seq traces (FIG. 94).

Figure 21:
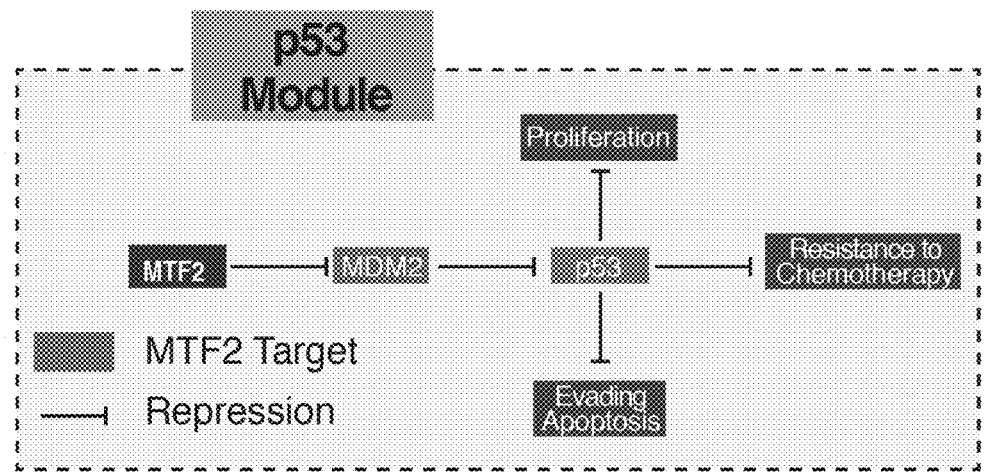
FIG. 21 depicts an oncogenic module within the MTF2-PRC2 GRN revealing that MTF2 directly represses MDM2, a master inhibitor of the p53 pathway.
Figure 22:
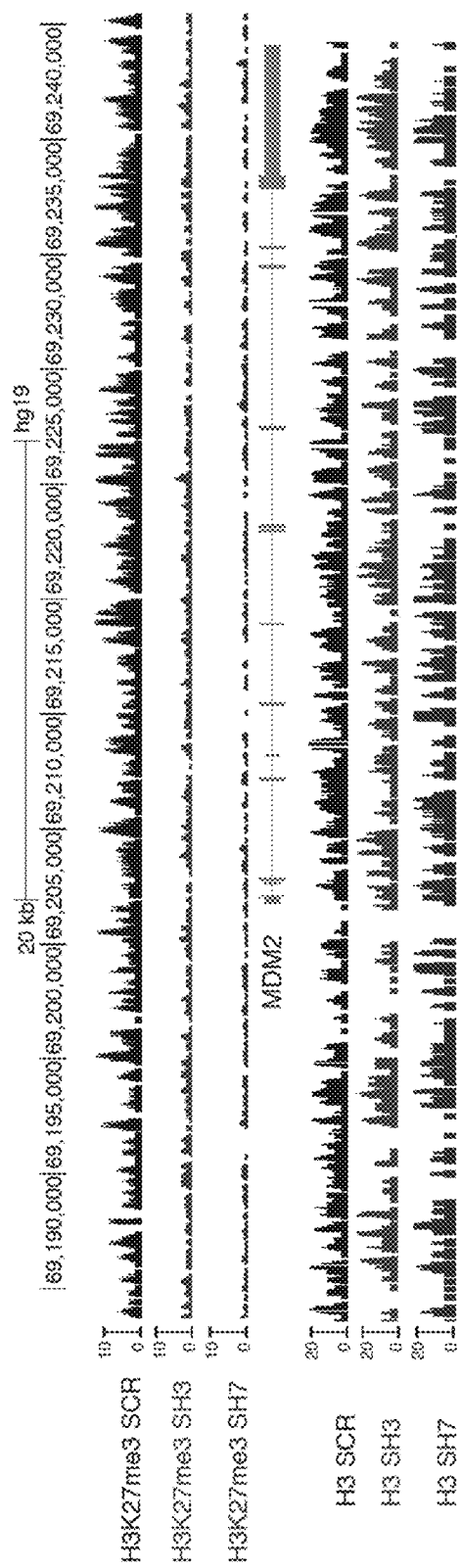
FIG. 22 depicts a Drosophila chromatin spike-in normalized ChIP-seq traces show loss of the repressive H3K27me3 marks at the MDM2 genomic locus in MTF2 knockdown (SH3, SH7) HSPCs relative to Histone 3 marks.
Figure 23:
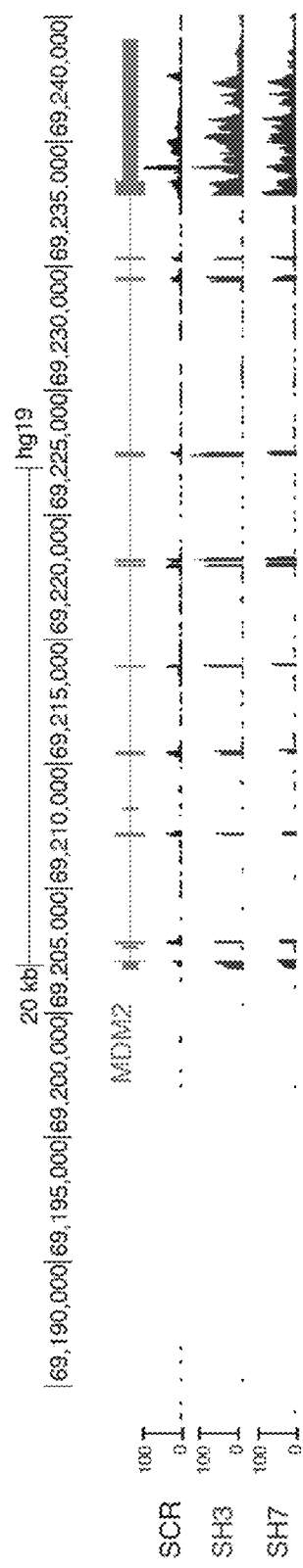
FIG. 23 shows RNA-seq traces displaying increased MDM2 mRNA levels in MTF2 knockdown (SH3 or SH7) HSPCs relative to scramble control (SCR) HSPCs.
Figure 24:
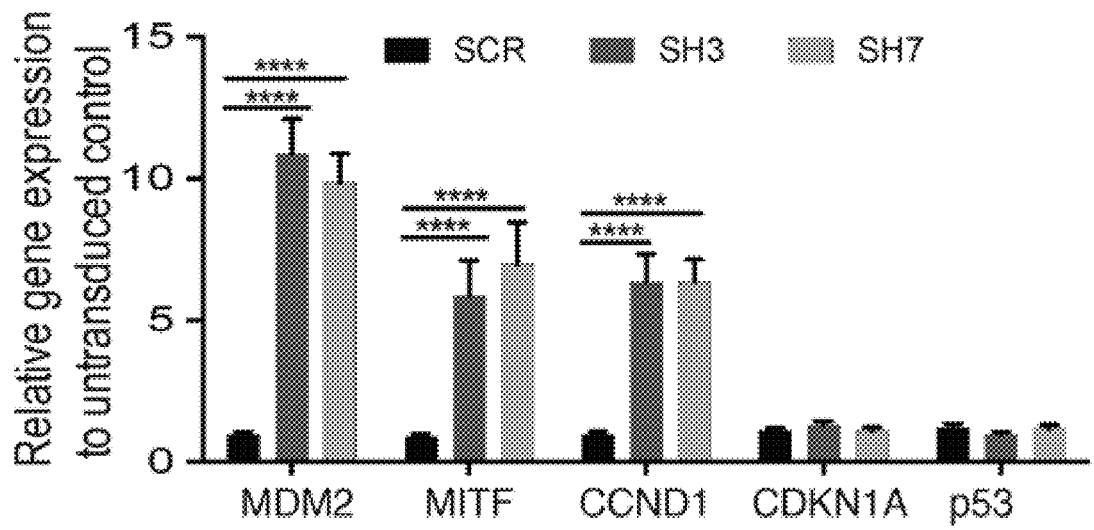
FIG. 24 shows that RT-qPCR performed on target genes validated the GRN.
Figure 25:
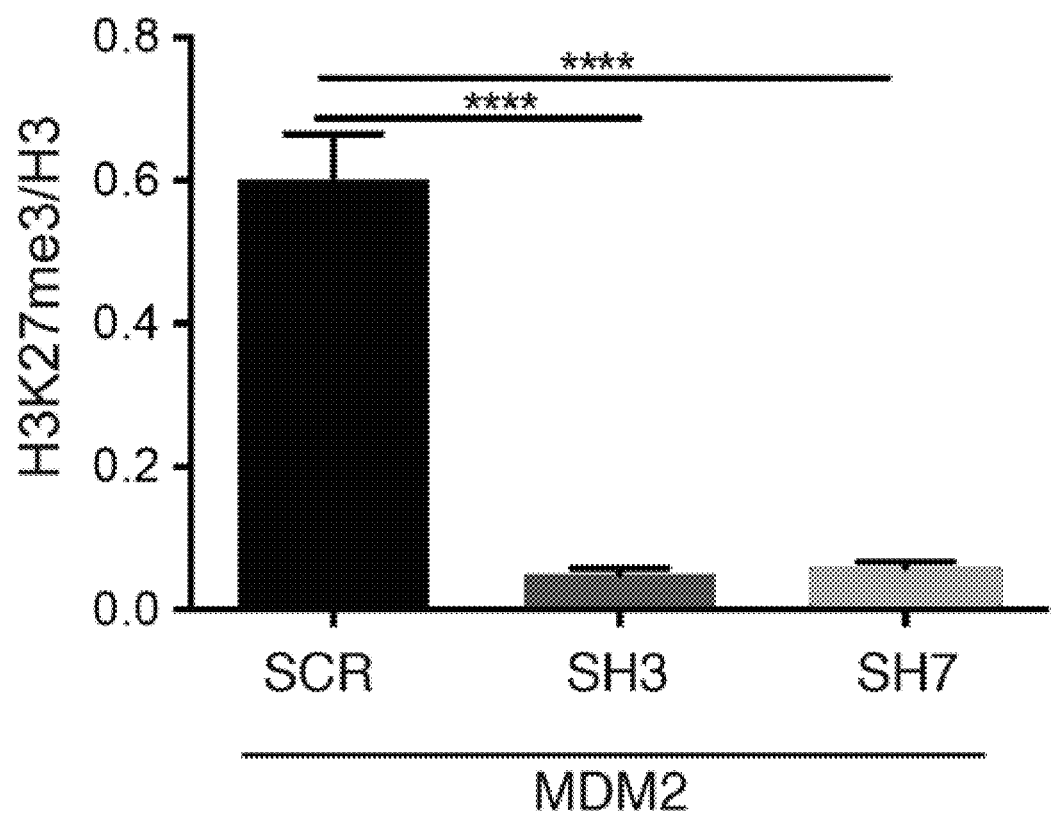
FIG. 25 shows that ChIP-qPCR performed on target genes validated loss of H3K27me3 repressive marks at the MDM2 locus in MTF2 deficient (SH3 or SH7) HSPCs.
Figure 26:
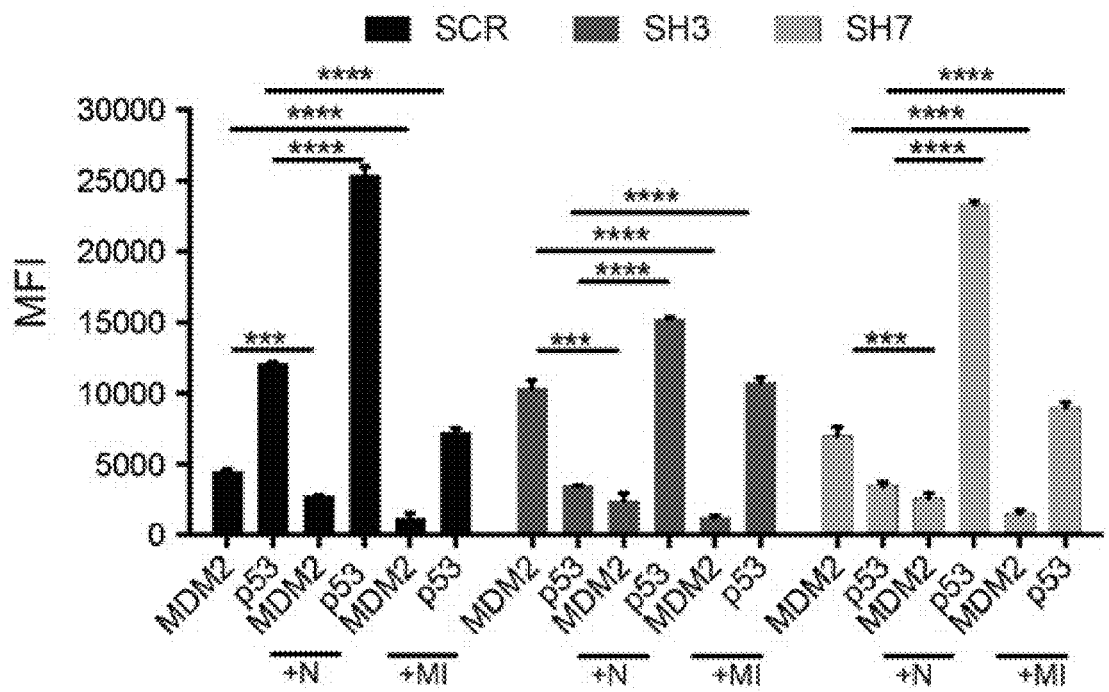
FIG. 26 depicts imaging flow cytometry analysis of MDM2 and p53, which revealed increased MDM2 and decreased p53 levels within MTF2 knockdown (SH3, SH7) HSPCs. Decreased p53 levels within MTF2 deficient HSPCs were rescued by treatment with MDM2 inhibitors Nutlin3a [N] or MI-773 [MI].

While p53 is not a direct target of MTF2-PRC2, the E3-ubiquitin ligase MDM2 that targets p53 for degradation[14] is a direct target. Thus, the p53 module within the MTF2 GRN predicts that MTF2 deficiency leads to MDM2 overexpression, resulting in p53 degradation (FIG. 21). Indeed, ChIP-seq analysis revealed that MTF2 deficiency leads to loss of H3K27me3 at the MDM2 locus, while total H3 levels were unaltered (FIG. 22), concomitant with increased MDM2 mRNA levels observed by RNA-seq (FIG. 23). These results were validated via RT-qPCR and ChIP-qPCR (FIG. 24-25). Functional validation using imaging flow cytometry revealed that MTF2-deficient HSPCs had high MDM2 and low p53 levels (FIG. 26). Therefore, it is hypothesized that MDM2 inhibitors would restore p53 levels in MTF2-deficient cells. Strikingly, p53 levels within MTF2-deficient HSPCs and Lin$^-$CD34$^+$ leukemic cells from refractory patient BM aspirates (MD-AML) were rescued by treatment with Nutlin3A or MI-773, which block MDM2-p53 interaction[15-17] (FIG. 26, 64-68).

Figure 69:
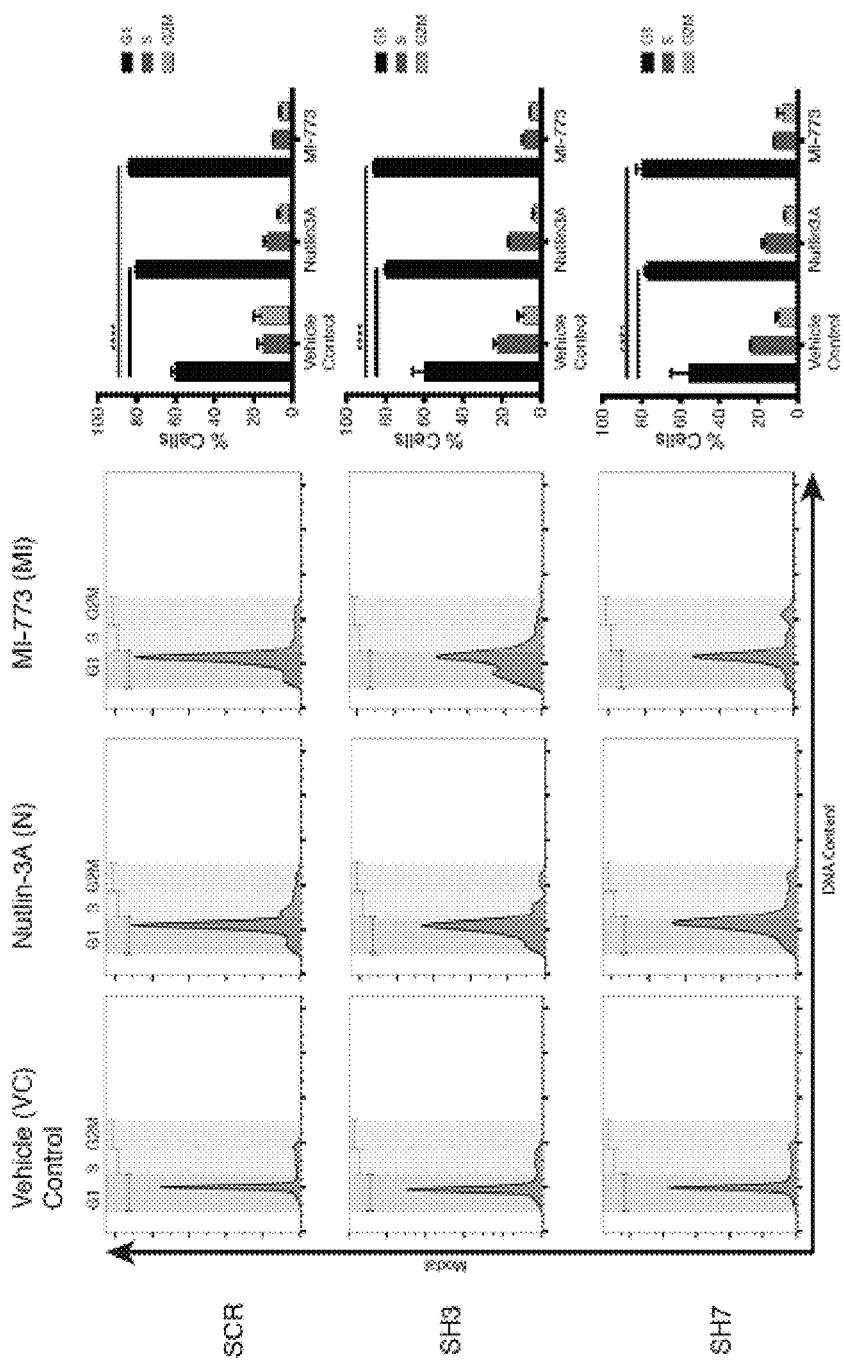
FIG. 69 depicts (at left) flow cytometric analysis of cell cycle profiles of vehicle control [VC], Nutlin3a [N], or MI-773 [MI] treated scramble (SCR) control or MTF2 shRNA knockdown (SH3 or SH7) HSPCs. Gating the individual cell cycle stages was performed by modeling the profile to the preset algorithm Dean Jett Fox. Right, quantification of the population distribution within the cell cycle stages demonstrates cells arresting in $G_0/G_1$ when treated with either 1 μM Nutlin3a or MI-773 for 24 hours.
Figure 70:
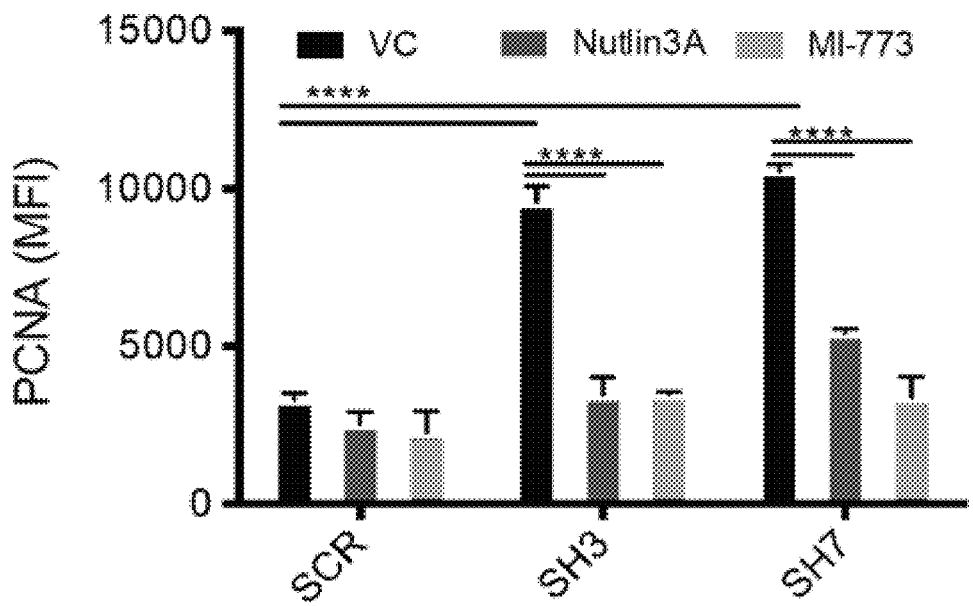
FIG. 70 depicts assessment of proliferation 24 hours post-treatment with either 1 μM Nutlin3a or MI-773 where a decrease in overall PCNA levels are observed in MTF2 deficient (SH3 or SH7) HSPCs (VC, vehicle control).

Furthermore, cell cycle and PCNA analyses revealed that rescuing p53 levels within MTF2-deficient HSPCs using MDM2 inhibitors decreased their proliferation rate and arrested the cells in the G0/G1 cell cycle stage (FIG. 69-70).

Figure 71:
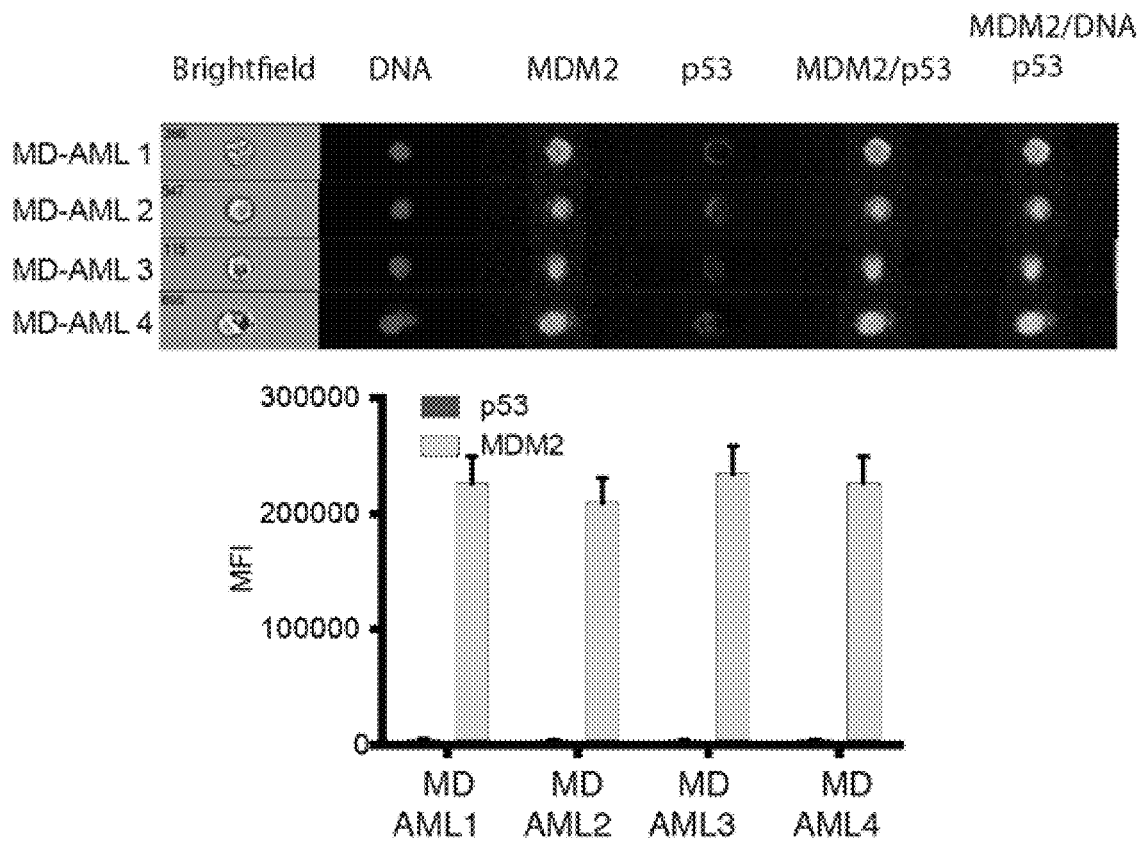
FIG. 71 shows assessment of MDM2 and p53 levels in Lin$^-$CD34$^+$ leukemic cells from MTF2 deficient refractory patient BM aspirates [MD-AML] by imaging flow cytometric analysis. Data indicated an overexpression of MDM2 and low p53 levels in MD-AML cells.
Figure 72:
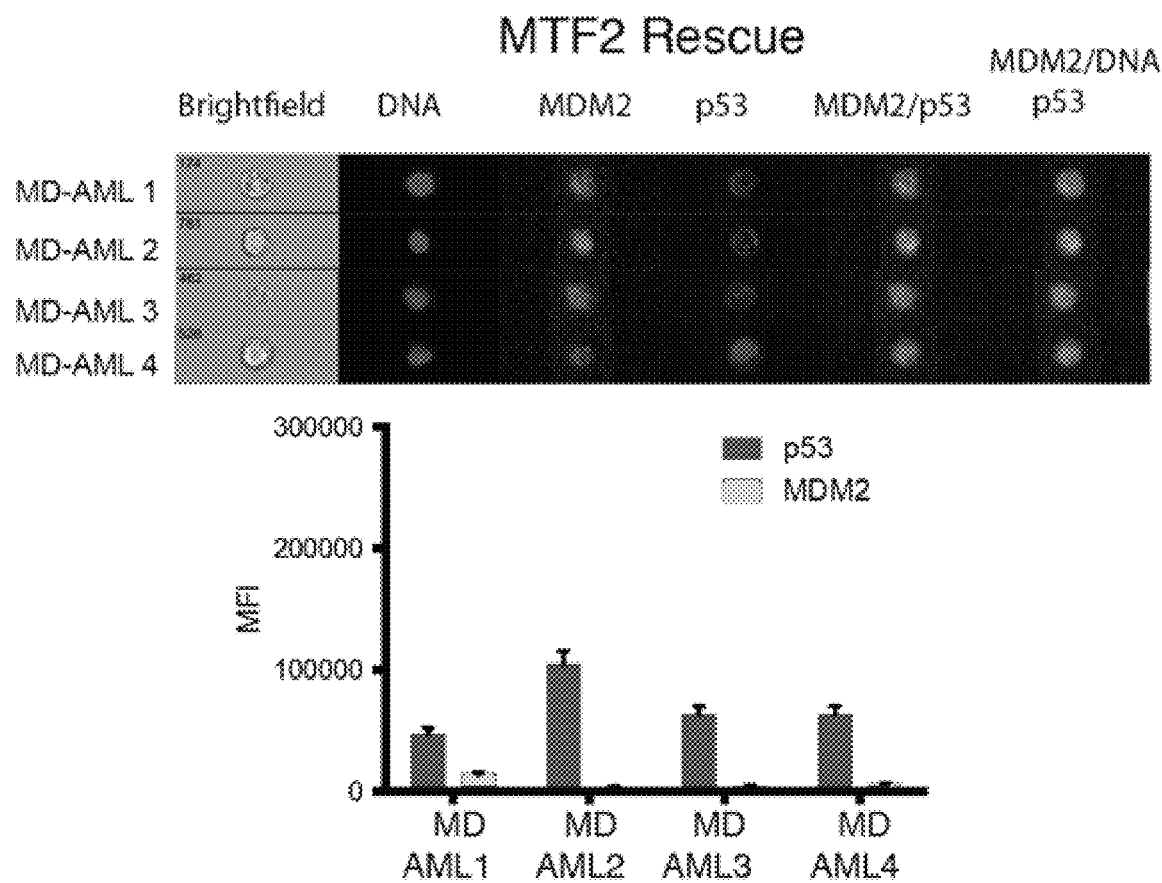
FIG. 72 depicts imaging flow cytometric analysis results indicating that high MDM2 and low p53 levels are reversed when MTF2 is overexpressed in MTF2 deficient AML [MD AML] Lin$^-$CD34$^+$ leukemic patient cells via lentiviral transduction, resulting in decreased MDM2 and increased p53 levels.
Figure 73:
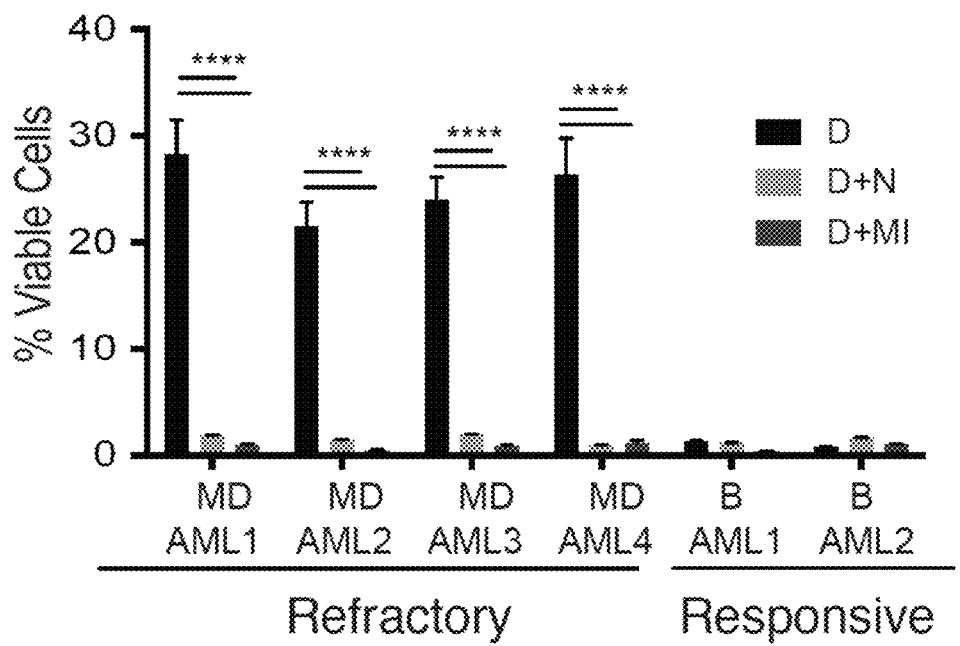
FIG. 73 shows that MTF2 deficient refractory AML patient cells [MD-AML] showed increased sensitivity to Daunorubicin (D) when treated in combination with MDM2 inhibitor MI-773 (MI) or Nutlin3A (N) for 48 hours that is comparable to MTF2 basal AML patient cells [B-AML].
Figure 74:
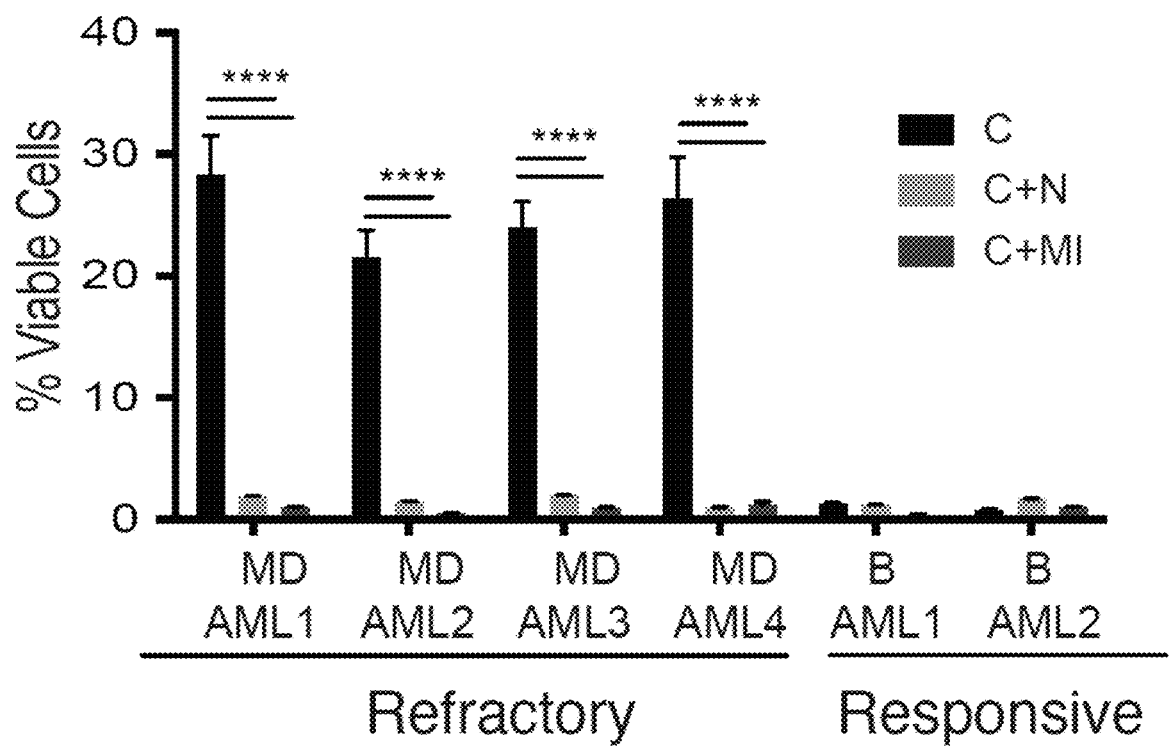
FIG. 74 shows that MTF2 deficient refractory AML patient cells [MD-AML] showed increased sensitivity to Cytarabine (C) when treated in combination with MDM2 inhibitor MI-773 (MI) or Nutlin3A (N) for 48 hours that is comparable to MTF2 basal AML patient cells [B-AML].
Figure 75:
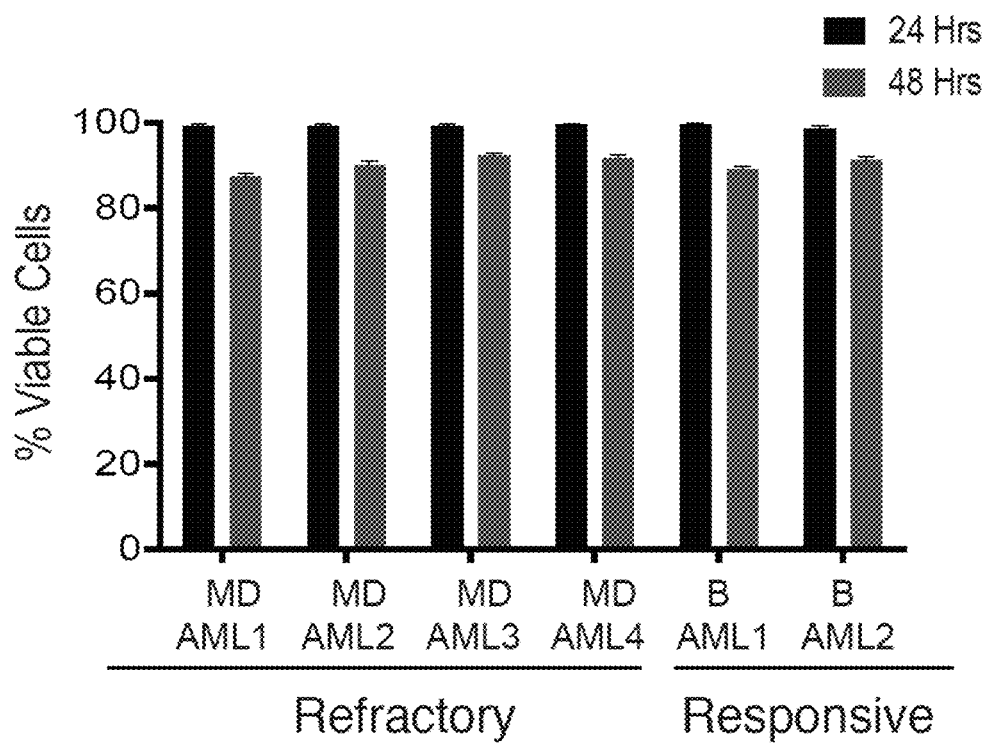
FIG. 75 shows that Treatment with Nutlin3a alone elicited a very low apoptotic effect over the course of 48 hours, reinforcing its low cytotoxic effect individually. Flow cytometry analysis was used to detect viable cells, which were determined by the percent of Annexin V-negative/7-AAD-negative cells.
Figure 76:
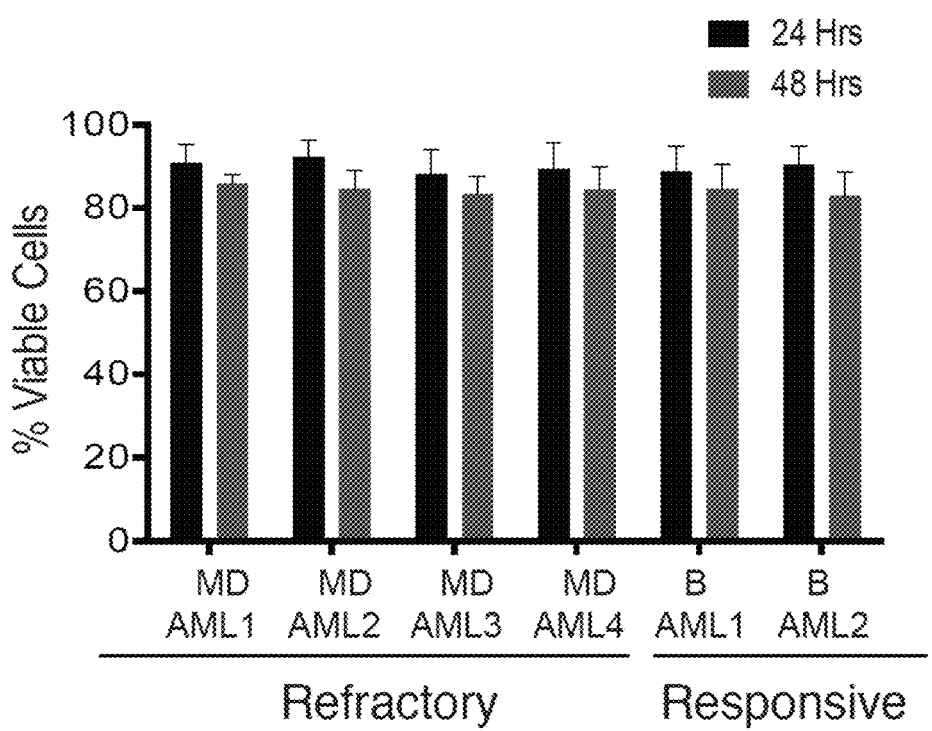
FIG. 76 shows that treatment with MI-773 alone elicited a very low apoptotic effect over the course of 48 hours, reinforcing its low cytotoxic effect individually. Flow cytometry analysis was used to detect viable cells, which were determined by the percent of Annexin V-negative/7-AAD-negative cells.

To test whether MTF2 regulates the MDM2-p53 axis in refractory AML patient BM cells, MTF2 expression was rescued within the MTF2-deficient Lin⁻CD34⁺ refractory patient BM aspirates (MD-AML) by lentivirus-mediated MTF2 expression; this resulted in MDM2 repression and elevated p53 protein levels (FIG. 71-72). Taken together, these results indicate that the MTF2 regulates p53 levels via transcriptional repression of MDM2 and that MDM2 inhibitors rescue p53 levels in MTF2-deficient cells.

Figure 27:
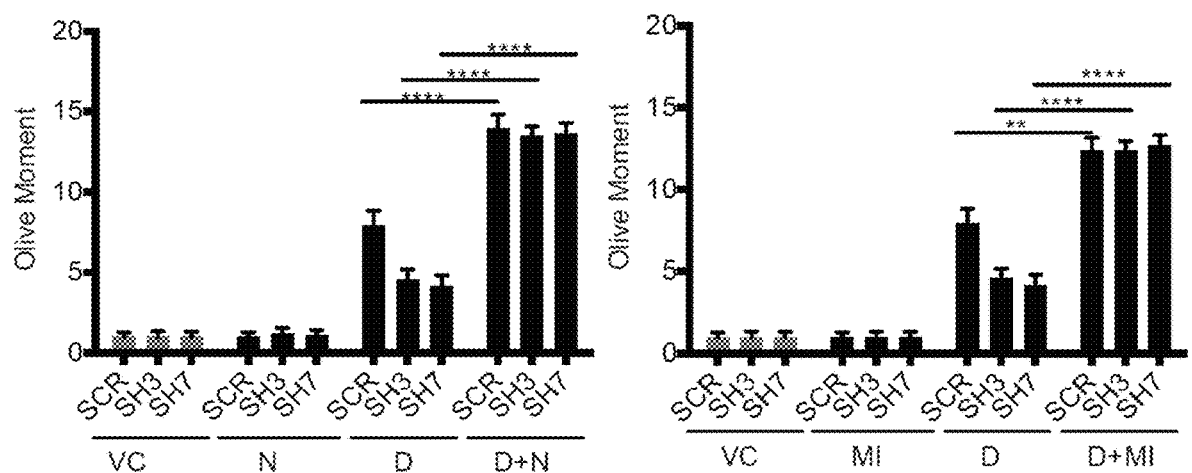
FIG. 27 depicts alkaline comet analysis of control (SCR) and MTF2 deficient (SH3, SH7) HSPCs treated with vehicle control [VC], Daunorubicin [D] in combination with one of two MDM2 inhibitors, Nutlin3A [N] or MI-773 [MI].
Figure 28:
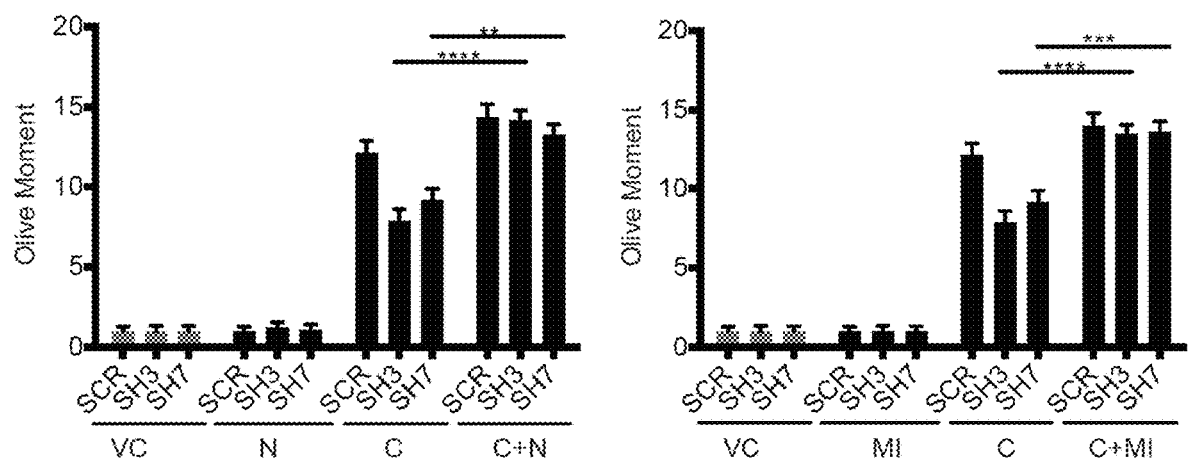
FIG. 28 depicts alkaline comet analysis of control (SCR) and MTF2 deficient (SH3, SH7) HSPCs treated with vehicle control [VC], Cytarabine [C] in combination with one of two MDM2 inhibitors, Nutlin3A [N] or MI-773 [MI].
Figure 29:
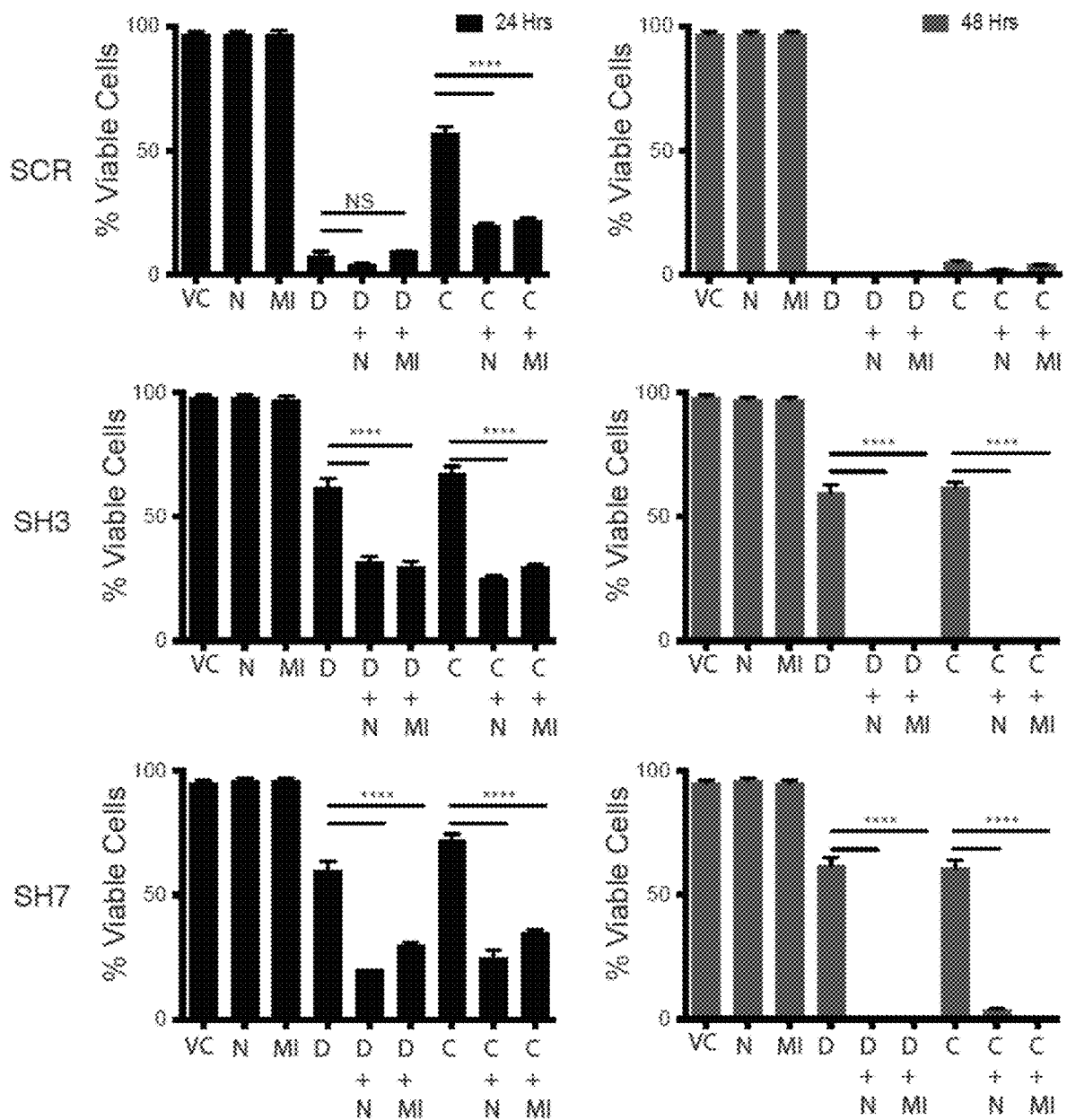
FIG. 29 depicts results of viability and apoptosis analysis to assess chemoresistance post-treatment with induction drugs, MDM2 inhibitors or both. MTF2 deficient (SH3, SH7) HSPCs undergo apoptosis post-combination treatment with induction drug plus MDM2 inhibitor, over 48 hours.
Figure 30:
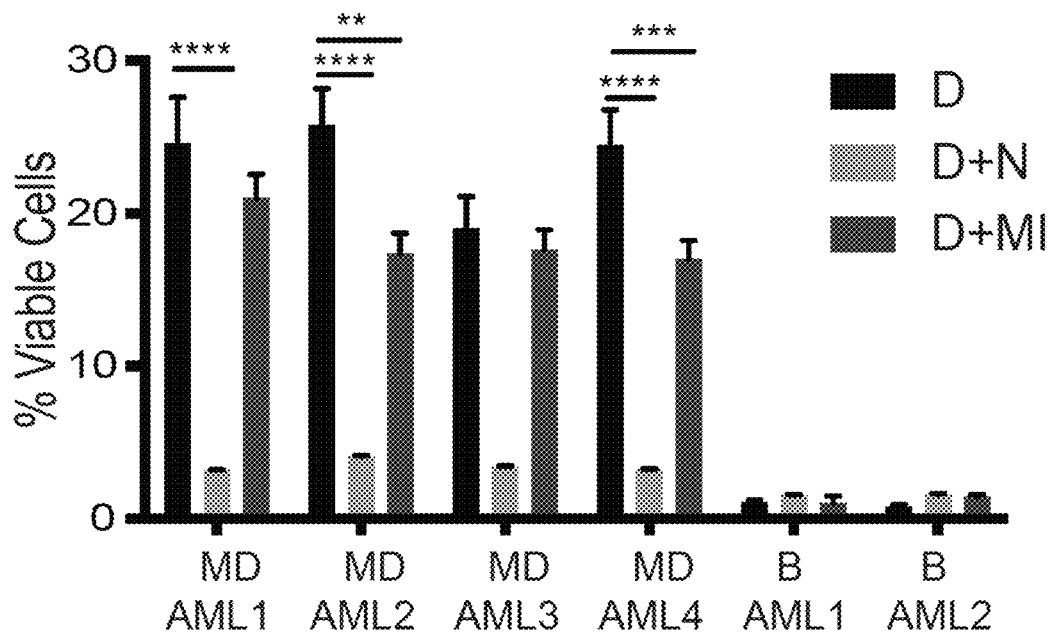
FIG. 30 shows that MTF2 deficient refractory AML cells [MD-AML] showed increased sensitivity to Daunorubicin when treated in combination with MI-773 [MI] or Nutlin3A [N] within 24 hours comparable to MTF2 basal AML samples [B-AML].
Figure 31:
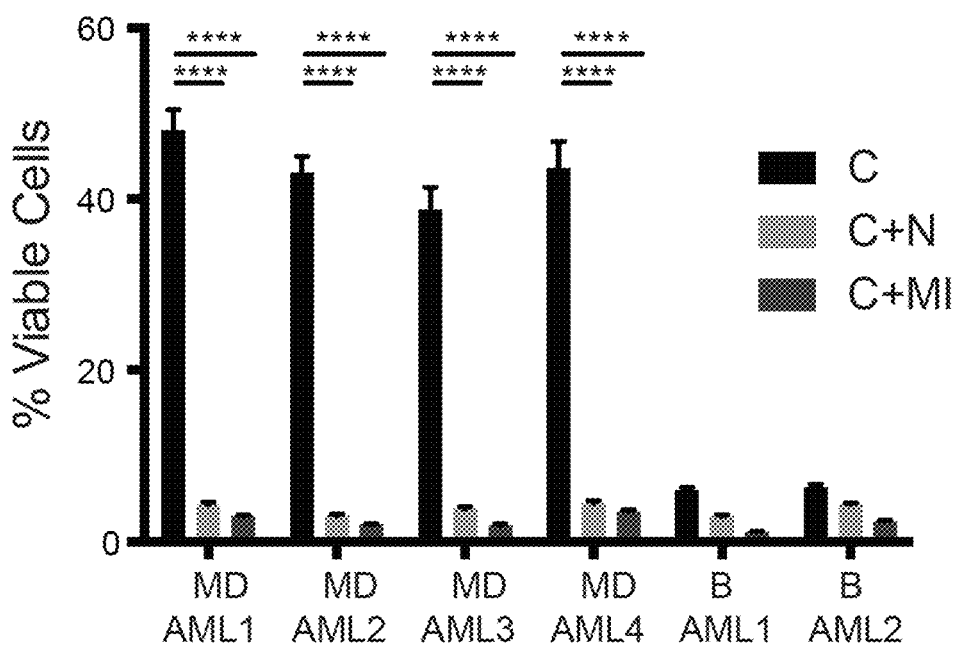
FIG. 31 shows that MTF2 deficient refractory AML cells [MD-AML] showed increased sensitivity to Cytarabine when treated in combination with MI-773 [MI] or Nutlin3A [N] within 24 hours comparable to MTF2 basal AML samples [B-AML].

Under normal circumstances, activation of the p53 pathway inhibits the propagation of cells that carry damaged DNA. In AML, inactivation of p53 is associated with chemoresistance, refractory disease, adverse risk group, and poor survival[9]. It was therefore hypothesized that rescuing p53 levels in MTF2-deficient HSPCs with MDM2 inhibitors would sensitize them to standard induction therapy drugs. To test this hypothesis, transduced viable GFP⁺ MTF2 knockdown HSPCs were sorted, as above, and treated with Cytarabine or Daunorubicin in combination with the MDM2 inhibitors Nutlin3A or MI-773, then assayed for DNA damage accumulation and cell viability. Importantly, MTF2-deficient HSPCs exposed to the combination treatment exhibited the same amount of DNA damage accumulation as that found within scramble controls and were sensitized to induction therapy drugs (FIG. 27-29). Moreover, MTF2-deficient refractory AML cells (MD-AML) underwent apoptosis when treated with Cytarabine or Daunorubicin in combination with Nutlin3A or MI-773, but not when treated with Nutlin3A or MI-773 alone (FIG. 30-31, 73-76). These in vitro results led us to further test this combination therapy regimen (standard induction drugs plus MDM2 inhibition) in vivo.

Figure 32:
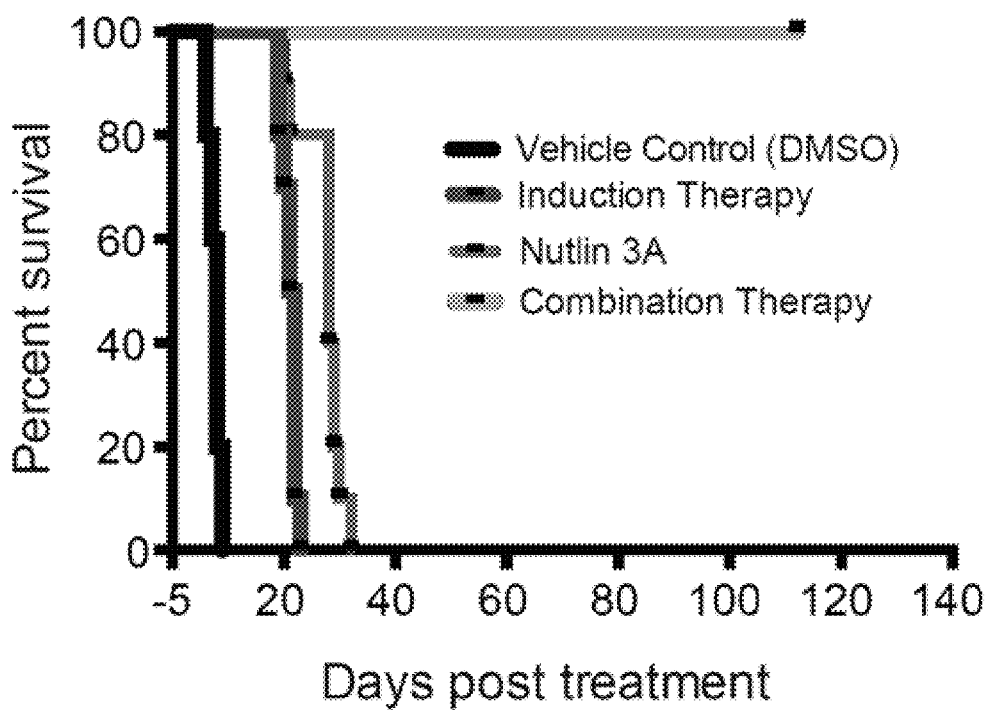
FIG. 32 depicts a Kaplan-Meier curve of AML patient-derived xenograft (PDX) NSG mice treated with either vehicle control, Nutlin3A alone, induction therapy or combination therapy (Nutlin 3A and induction drugs) (n=4 refractory AML samples; n=8 mice per treatment group).
Figure 33:
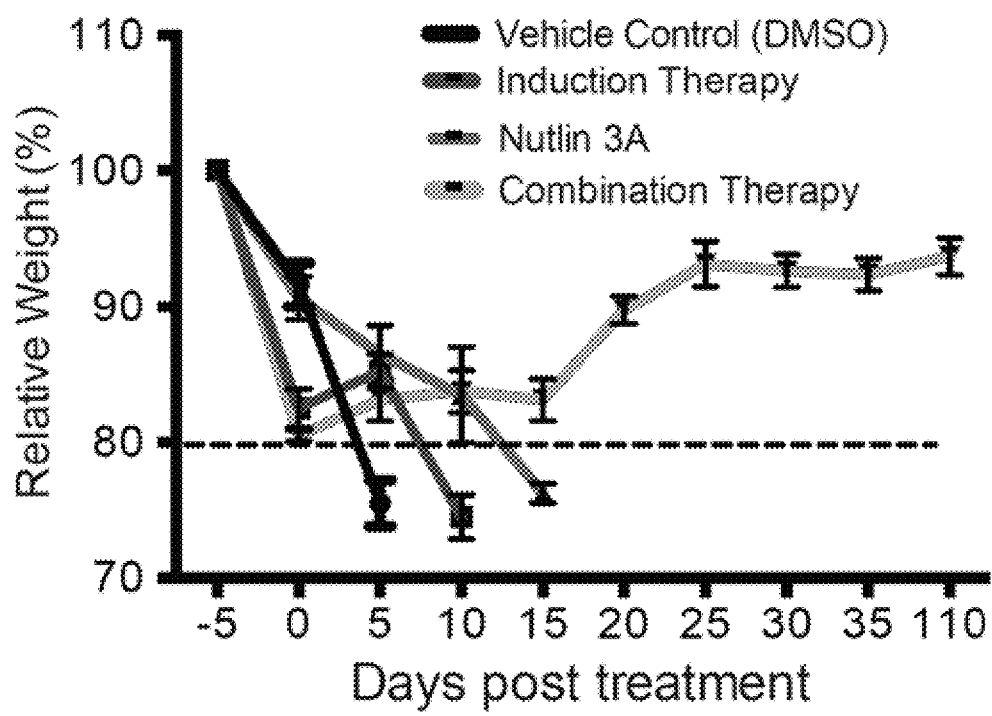
FIG. 33 shows that mouse weight was monitored up to 16 weeks post-treatment. Initial weight loss was observed in all conditions, but weight recovery was only observed in mice that underwent combination treatment.
Figure 34:
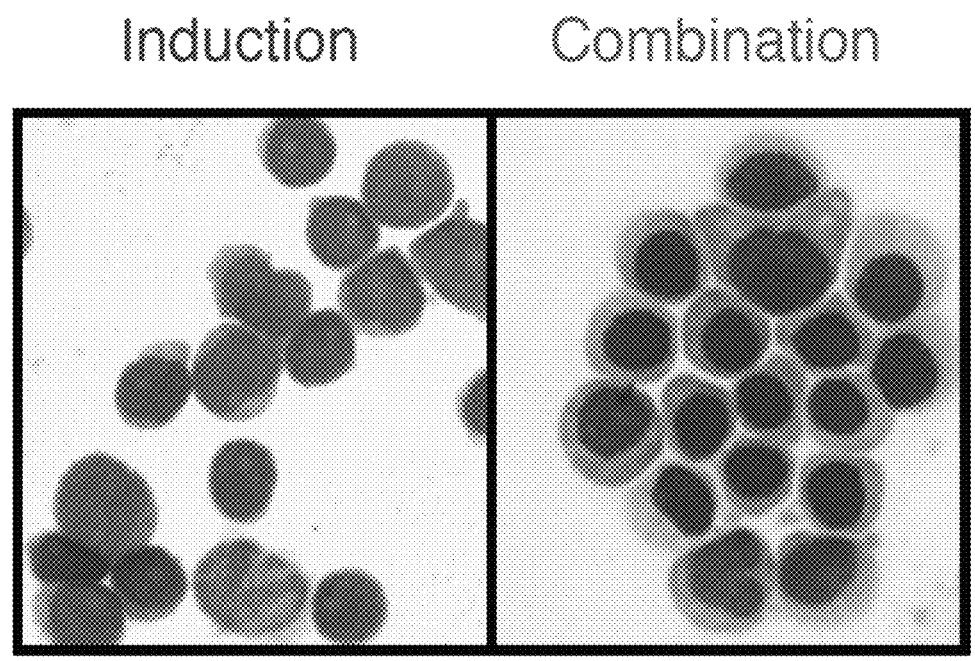
FIG. 34 shows Wright-Giemsa-stained cytospins of BM samples from PDX mice treated with induction therapy and combination therapy, which demonstrate a loss of immature blast cells following combination treatment only.
Figure 77:
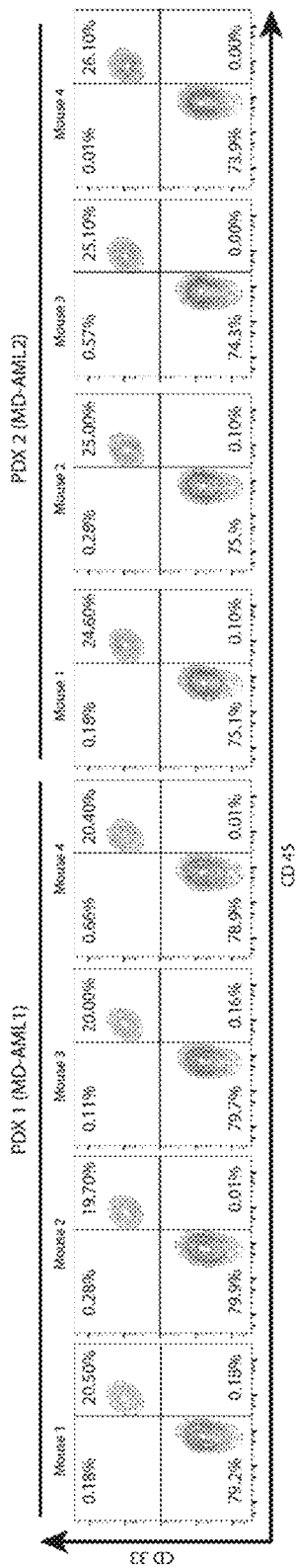
FIG. 77 depicts representative flow cytometry plots demonstrating ≥20% engraftment of patient derived xenograft (PDX) CD45+CD33+ cells in the peripheral blood of NSG mice that were transplanted with MTF2 deficient AML BM patient cells [MD-AML] via tail vein (n=4 refractory AML samples).
Figure 78:
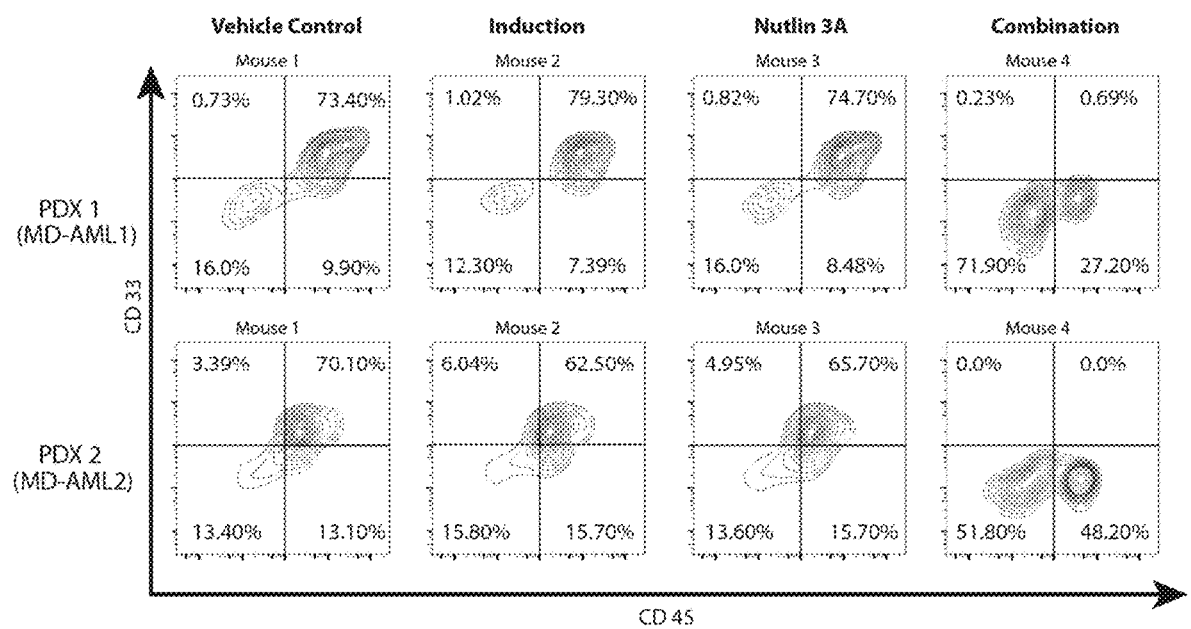
FIG. 78 shows representative flow cytometry plots analyzing CD45$^+$CD33$^+$ cells in the BM of treated mice at time of sacrifice. Upon ≥20% engraftment of MTF2 deficient AML PDX CD45$^+$CD33$^+$ cells, mice were treated with either vehicle control [VC], induction therapy, Nutlin3A alone, or combination therapy (induction drugs and MDM2 inhibitor).
Figure 79:
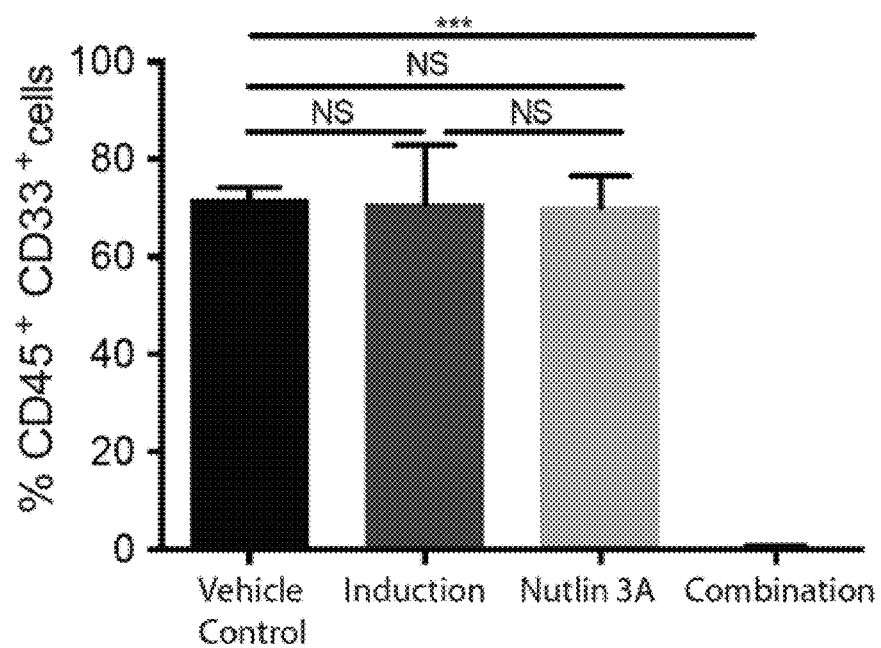
FIG. 79 shows quantification of flow cytometry analysis demonstrating a significant decrease of CD33$^+$ cells within the bone marrow of PDX mice in the combination drug cohort (induction drugs and MDM2 inhibitor) compared with the other treatment cohorts.
Figure 80:
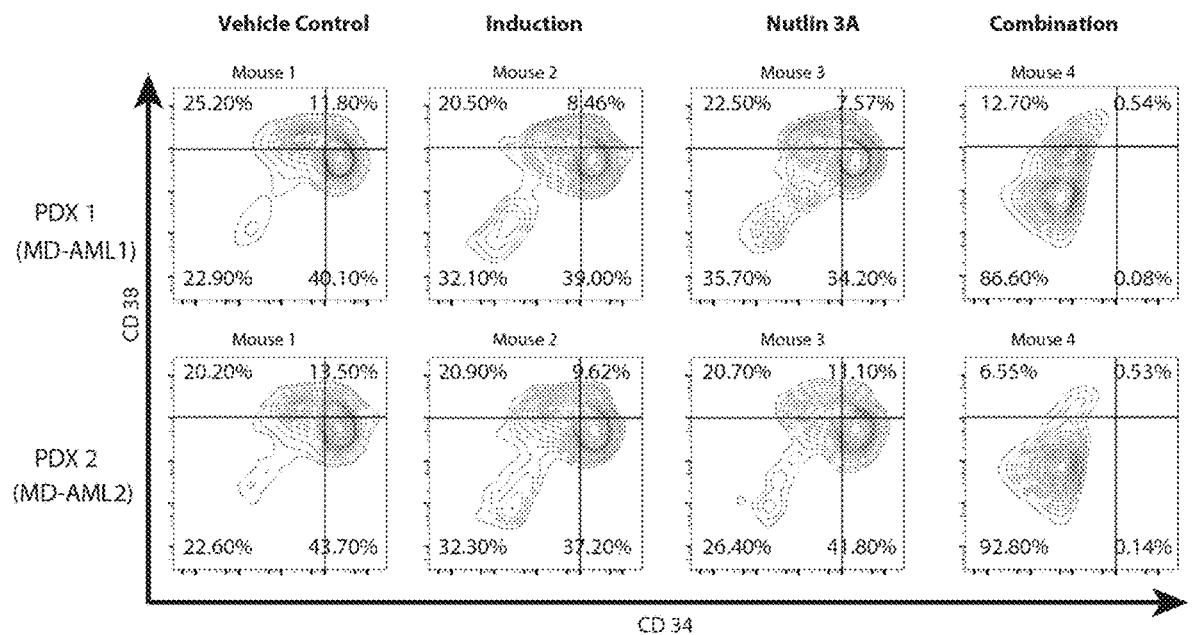
FIG. 80 depicts representative flow cytometry plots of bone marrow analyses assessing the percent CD34$^+$CD38$^-$ LSC-enriched and CD34$^+$CD38$^+$ populations of mice in each treatment group at time of sacrifice.
Figure 81:
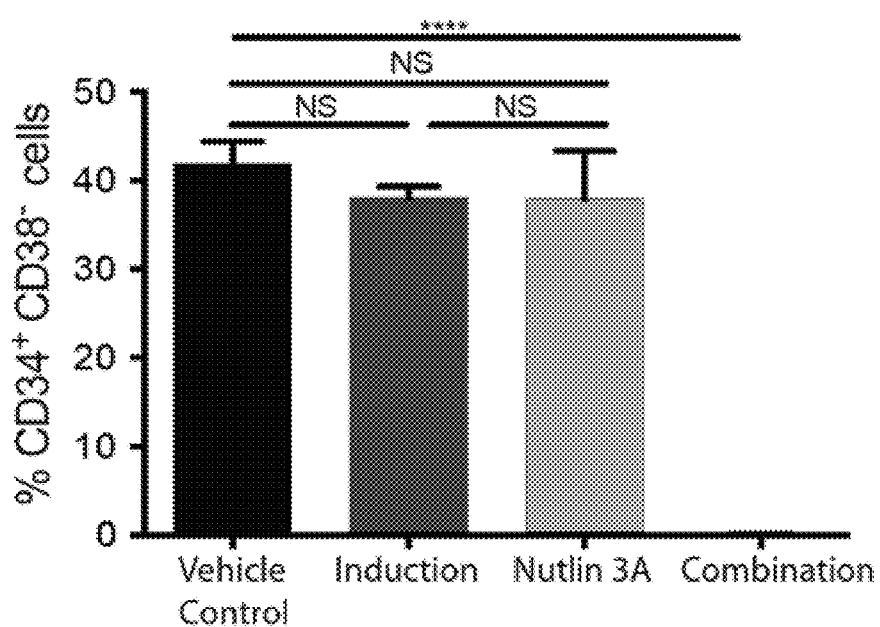
FIG. 81 shows quantification of flow cytometry analysis showing that 16-weeks event-free post treatment, the combination treatment dramatically reduced the CD34$^+$CD38$^-$ population within the bone marrow. Vehicle control, Nutlin 3A and induction therapy cohorts were moribund and sacrificed <6 weeks post-treatment, but the combination treatment cohort was sacrificed 16 weeks post-treatment when the experiment was terminated. (n=4 MD-AML samples, n=2 mice per treatment group and n=8 mice total per treatment group).
Figure 82:
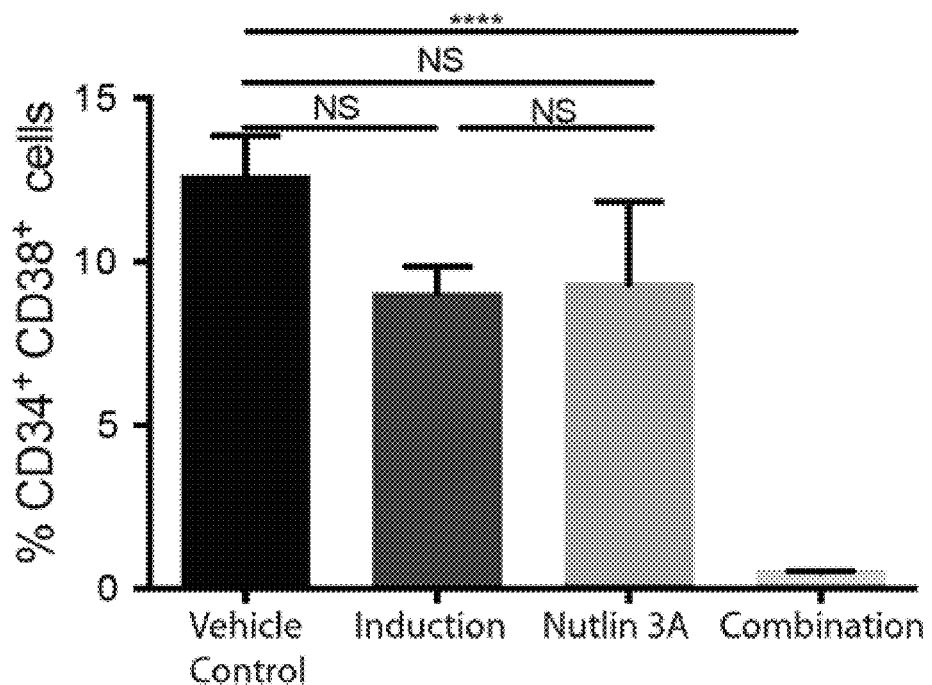
FIG. 82 shows quantification of flow cytometry analysis showing that 16-weeks event-free post treatment, the combination treatment dramatically reduced the CD34$^+$CD38$^+$ population within the bone marrow. Vehicle control, Nutlin 3A and induction therapy cohorts were moribund and sacrificed <6 weeks post-treatment, but the combination treatment cohort (induction drugs and MDM2 inhibitor) was sacrificed 16 weeks post-treatment when the experiment was terminated. (n=4 MD-AML samples, n=2 mice per treatment group and n=8 mice total per treatment group).
Figure 83:
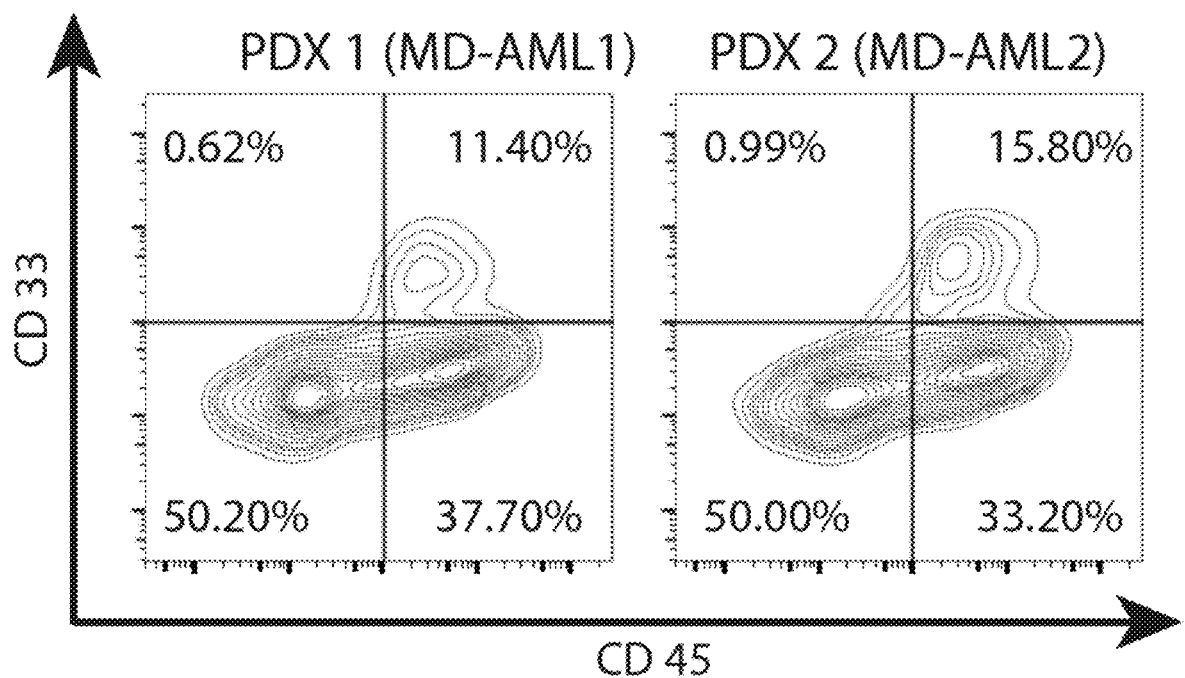
FIG. 83 depicts representative flow cytometry plots of BM analysis of CD45$^+$CD33$^+$ myeloid cells in secondary recipients. Bone marrow from primary NSG mice transplanted with patient derived xenograft (PDX) MTF2 deficient AML [MD-AML] and treated with combination therapy (induction drugs and MDM2 inhibitor) was harvested 16 weeks post-treatment and transplanted into secondary recipients. Event-free multi-lineage engraftment potential of HSPCs, myeloid and lymphoid lineages was assessed at 16 weeks post-secondary transplant.
Figure 84:
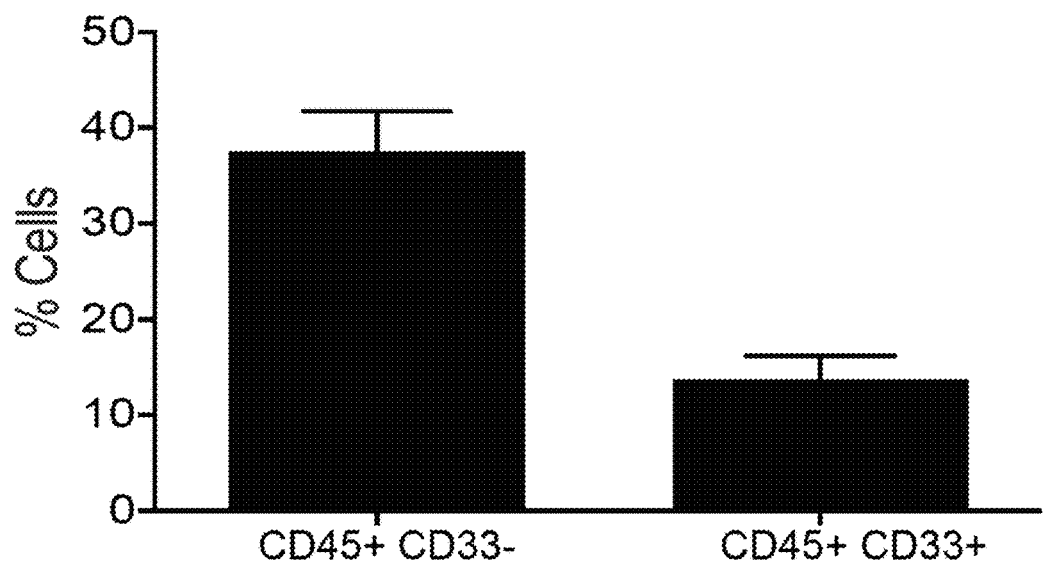
FIG. 84 depicts mean CD45$^+$CD33$^+$ percentage and shows robust myeloid engraftment in secondary transplant recipients from primary mice treated with combination therapy (induction drugs and MDM2 inhibitor).
Figure 85:
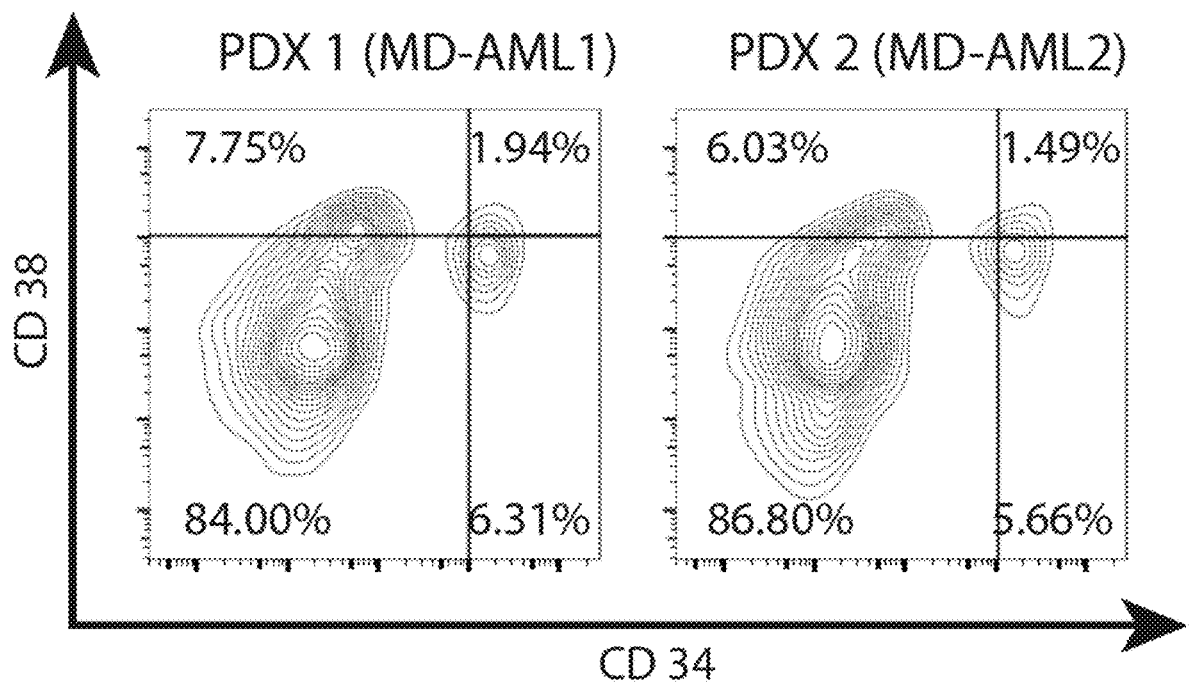
FIG. 85 depicts representative flow cytometry analysis of BM assessing HSPC populations in secondary transplant recipients from primary mice treated with combination therapy (induction drugs and MDM2 inhibitor).
Figure 86:
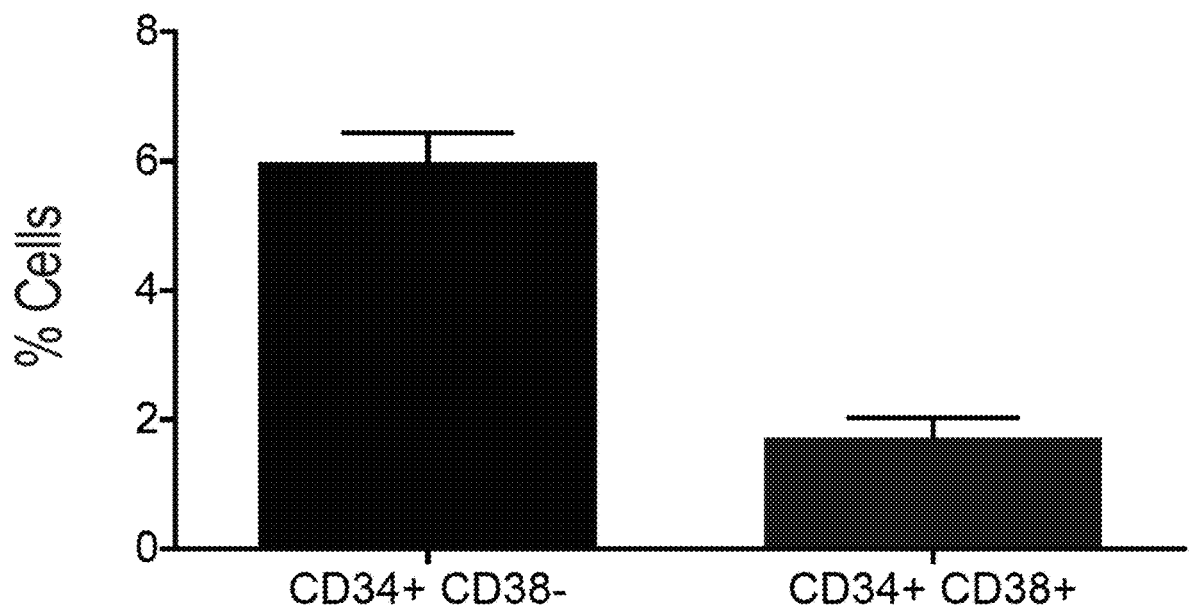
FIG. 86 depicts quantitative assessment of the HSPC populations based on CD34 and CD38 expression within the BM of the secondary recipients from primary mice treated with combination therapy (induction drugs and MDM2 inhibitor).
Figure 87:
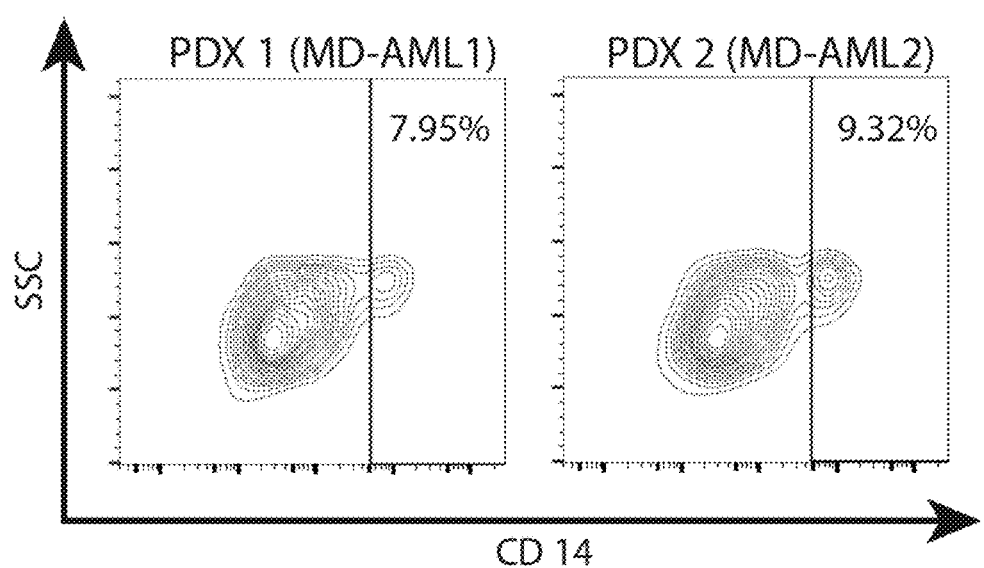
FIG. 87 depicts representative flow cytometry BM analyses assessing the percent CD14$^+$ monocyte engraftment in secondary transplants from primary mice treated with combination therapy (induction drugs and MDM2 inhibitor).
Figure 88:
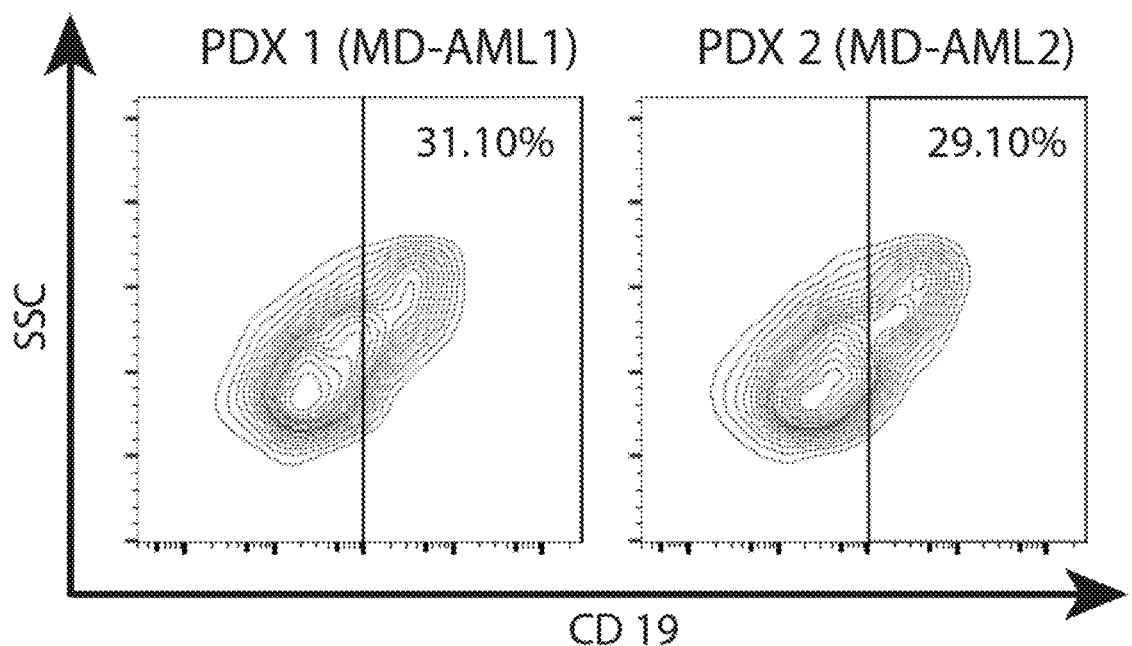
FIG. 88 depicts representative flow cytometry BM analyses assessing the percent CD19$^+$ B-lymphocyte engraftment in secondary transplants from primary mice treated with combination therapy (induction drugs and MDM2 inhibitor).
Figure 89:
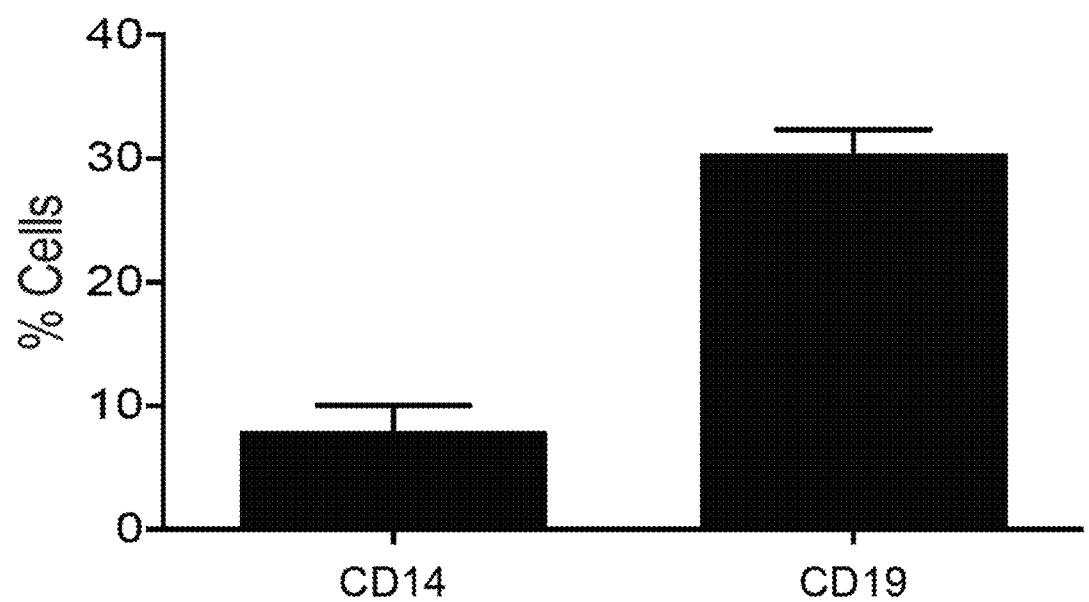
FIG. 89 show mean CD14$^+$ and CD19$^+$ engraftment in secondary recipients from primary mice treated with combination therapy (induction drugs and MDM2 inhibitor) (n=4 AML refractory samples; n=4 secondary mice in total).

Mindful of the disparity between pre-clinical and clinical trial results[18,19], a pre-clinical study was designed that would closely mirror a clinical trial. Thus, the following principles were incorporated: refractory AML patient derived xenograft (PDX) mice would be treated only after the mice presented with a substantial leukemic burden, the efficacy of combination therapy would be compared against standard induction chemotherapy, and the study would be blinded. Irradiated NSG mice were injected with MTF2-deficient refractory AML (MD-AML) patient-derived xenograft (PDX) cells, as described previously[20]. Once the transplanted mice had ≥20% CD45⁺CD33⁺ blast cells in their peripheral blood, the mice were randomized into 4 groups, which were treated with either vehicle control, Nutlin3A, induction therapy or combination therapy that included induction therapy plus Nutlin3A (FIG. 77). While the mice treated with vehicle control, Nutlin3A alone, or induction therapy died within 4-5 weeks of treatment, all of the mice treated with combination therapy survived until the experiment was terminated at 16-weeks post-treatment (FIG. 32). Mouse weight was monitored throughout the study and reflected this survival curve with weights plummeting during the 5-day treatment; only combination therapy-treated mice regained their weight and recovered (FIG. 33). Wright-Giemsa staining of BM cells harvested at endpoint showed a stark contrast between the immature blast cells isolated from induction therapy-treated mice and the differentiated BM cells isolated from the combination therapy treated mice (FIG. 34). Flow cytometry analysis also confirmed a dramatic loss in the blast-containing CD45⁺ CD33⁺ and LSC-rich populations in the combination therapy cohort (FIG. 78-82).

Figure 35:
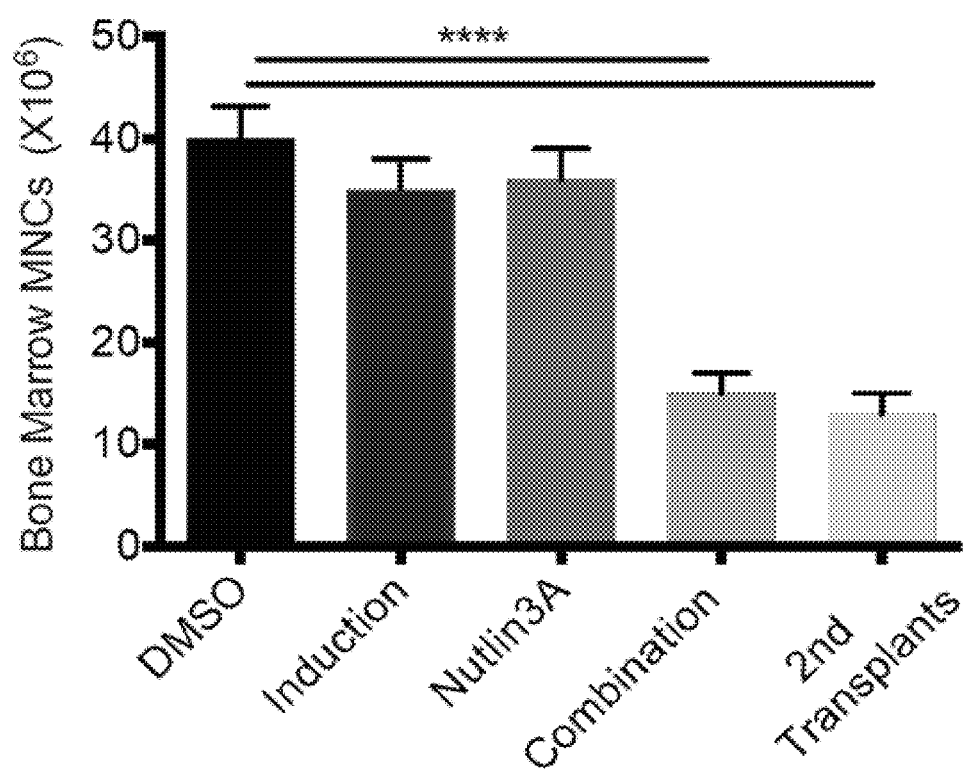
FIG. 35 BM mononuclear cell (MNC) counts from moribund mice following treatment with either vehicle control (DMSO), Nutlin3A or induction therapy and from surviving mice administered combination therapy 16-weeks post-treatment. A profound decrease in MNCs was observed in the bone marrow of primary mice that received combination therapy and their secondary transplant recipients.

To test whether the remaining PDX cells in the combination treated mice retained residual disease, secondary transplants were performed without additional treatment. The secondary transplants continued to survive 16-weeks post-transplantation until the experiment was terminated. Flow cytometry analysis of BM cells in secondary transplants revealed that the transplanted cells were capable of multi-lineage engraftment (FIG. 83-89). Finally, flow cytometric analysis showed the combination therapy treated mice and their secondary transplant recipients had reduced bone marrow cellularity, compared to DMSO, Nutlin3A alone or induction treated mice cohorts (FIG. 35).

By performing an unbiased systems analysis of refractory AML, it was discovered that decreased levels of MTF2 and H3K27me3 within enriched LSC populations prospectively identifies refractory AML at diagnosis, MTF2 is required to repress MDM2 in HSPCs and leukemic cells, and chemoresistance in MTF2- and H3K27me3-deficient AML is reversible by over-expression of MTF2 in vitro or using MDM2 inhibitors in vivo. These data suggest that MDM2 inhibitors in combination with standard induction chemotherapy provide a promising, targeted strategy in treating MTF2-deficient chemoresistant AML. In fact, the two MDM2 inhibitors used in this study are now in clinical trials for a number of indications including treatment of AML. Our data predict that in the absence of MDM2 inhibitors, MTF2-deficient AML cells will cycle through induction therapy and accumulate additional mutations, possibly even p53 mutations associated with therapy-induced mutations, that would render the cells resistant to MDM2 inhibitors. Therefore, it is proposed to screen AML patients at diagnosis for MTF2 (or MTF2 in combination with one of more other informative biomarkers identified herein), to prospectively identify chemoresistant AML prior to treatment in order to identify candidates who will benefit the most from combination therapy.

EXAMPLE 2

Introduction

As noted above, it was found that decreased MTF2 expression dysregulates two other pathways: the MDM2-p53 and DNA Damage Response (DDR) pathways, and it was therefore hypothesized that these pathways can be targeted therapeutically to treat the identified subpopulation of patients deficient in MTF2 and refractory to standard AML treatment.

MDM2 Pathway

MTF2 epigenetically represses MDM2, which is an E3 ubiquitin ligase that forms a complex with p53, thereby inhibiting p53 activity (which helps to mediate apoptotic cell death). Practically speaking, low MTF2 results in high MDM2, in turn resulting in reduced p53 activity. As such, it was hypothesized that in an MTF2-deficient subpopulation, administration of an MDM2 antagonist can increase p53 activity, making these leukemic cells more susceptible to p53 mediated-apoptosis, and therefore increase the success of standard induction therapy.

DDR Pathway

Target genes in the DDR pathway were identified that are upregulated in MTF2-deficient hematopoietic stem and progenitor cells (HSPCs), and that MTF2-deficient HSPCs tolerate DNA damage following treatment with induction drugs and continue to cycle. Error-prone DNA polymerases POLH, POLK and POLQ are upregulated, while genes involved in homologous recombination such as RAD50 and RAD51, which ensures more faithful DNA repair, are downregulated. More specifically, POLQ has been shown to inhibit homology directed repair (HDR).[33] Thus, inhibiting POLQ may be another therapeutic strategy to slow AML cell proliferation and induce HDR.

This would be used in combination with standard induction therapy and the MDM2 inhibitor.

Refractory Subpopulations

Other biomarker panels have proved useful in the identification of refractory subpopulations.

These panels are based on:

Low MTF2 expression;

Low H3K27 trimethylation;

High CD84 and/or CD92 expression;

High MDM2 expression;

High expression of one or more of NPM1, PRICKLE1, SET, and ABCB6;

High expression of POLQ; and/or

High expression of MCM6, PARP1.

The biomarker signature to be tested could involve any one or more of the above biomarkers. The biomarker signature to be tested could involve MTF2 in addition to any one or more of the above biomarkers. The biomarker signature to be tested could involve MTF2 in addition to any one or more of the above-noted groups of biomarkers. The biomarker signature to be tested could involve any one or more of the above-noted groups of biomarkers. The biomarker signature to be tested could involve CD92 in addition to any one or more of the above biomarkers. The biomarker signature to be tested could involve CD92 in addition to any one or more of the above-noted groups of biomarkers. The biomarker signature could comprise or consist of all of the above noted biomarkers.

Monoclonal antibodies for the proteins of these signature are used on blood/marrow samples to identify AML patients who would be refractory to standard chemotherapy, to ascertain a prognosis for treatment, and follow up care to monitor to success of the MDM2 inhibitor treatment.

These biomarkers can also be used to match refractory AML patients with targeted combinatorial drug regimens consisting of a small molecule MDM2 antagonist plus Cytarabine and Daunorubicin (standard therapy), as well as POLQ inhibitors or other therapeutic targets predicted by the MTF2 gene regulatory network.

MDM2 Inhibitors

Warner et al.[34] describe a new computational approach to identify drugs with potential activity computationally based on structural similar structures. This approach was utilized to identify 15 FDA-approved drugs that are predicted to inhibit p53-MDM2 interaction. The drugs are as follows (listed from the highest to lowest score).

These molecules were assessed to identify candidates to be used in combination with induction therapy drugs to treat AML patients. The drugs were ranked according to the scores based on structure, known bioactivity to bind MDM2, and the known risks/contraindications. The following drugs were selected to block MDM2 in MTF2-deficient hematopoietic or leukemic cells:

S-bepridil/Vascor

Protirelin/Thyrel TRH

Caramiphen/Oridine AT

Prenazone/Feprazone

Mephenoxalone

Azlocillin

Azaribine/Triazure

Clofazimine

Targeting DDR and POLQ

The MTF2-deficient gene regulatory network (GRN) revealed that DNA damage repair (DDR) genes are predominantly epigenetically regulated by MTF2 (FIGS. 60-63).

Figure 62:
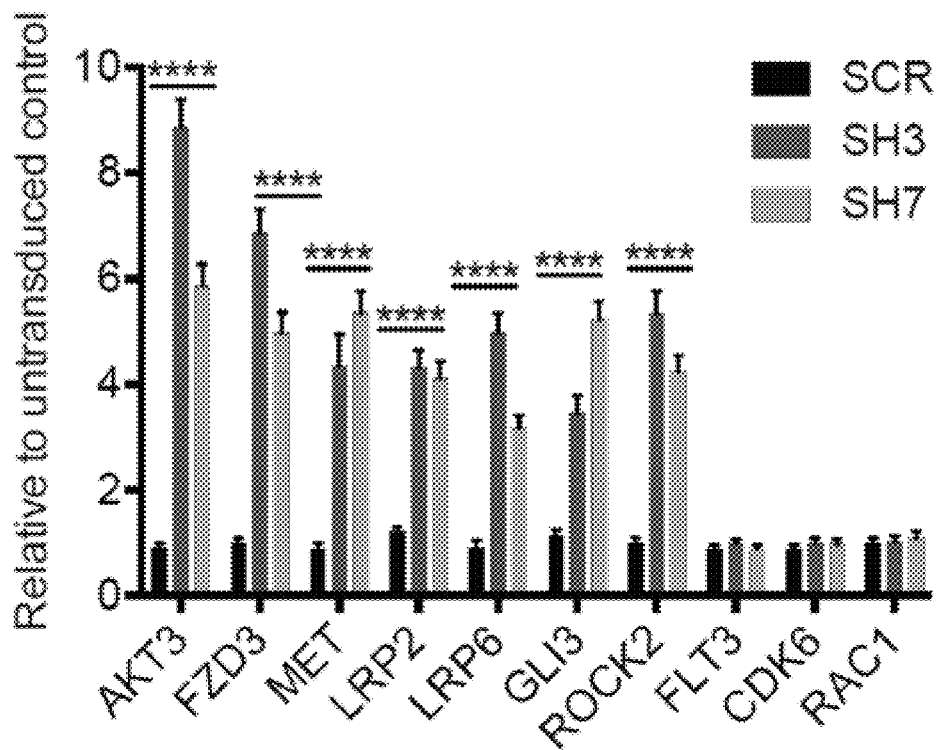
FIG. 62 shows RT-qPCR on MTF2 target DDR genes identified by RNA-seq validated targets. Experiments were performed in triplicate.
Figure 63:
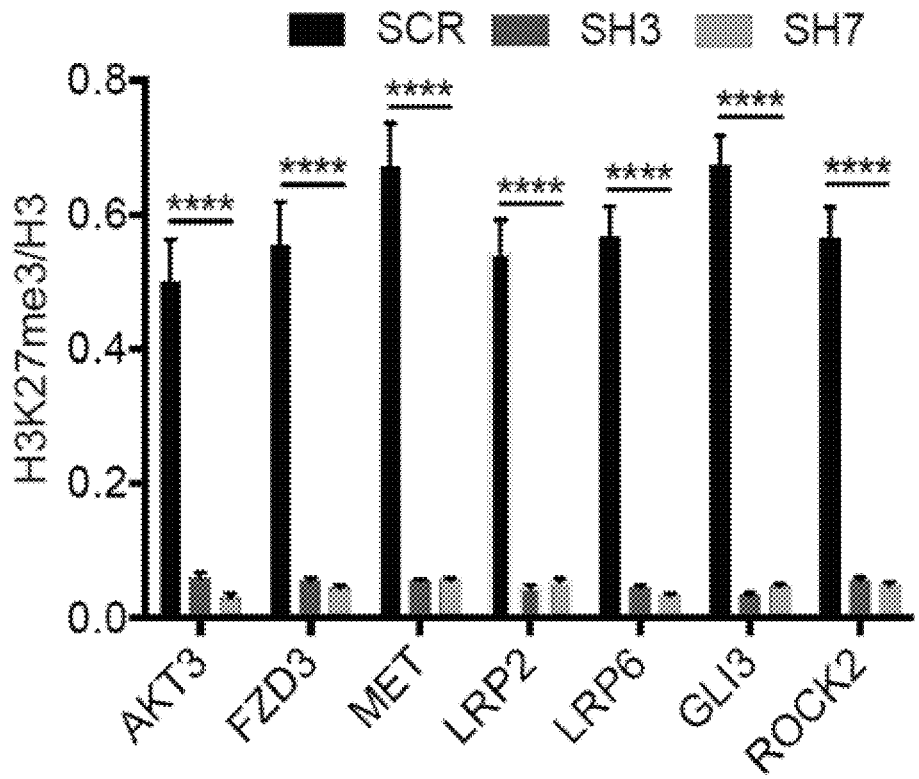
FIG. 63 shows ChIP-qPCR on MTF2 target DDR genes identified by ChIP-seq validated targets. Experiments were performed in triplicate.
Figure 64:
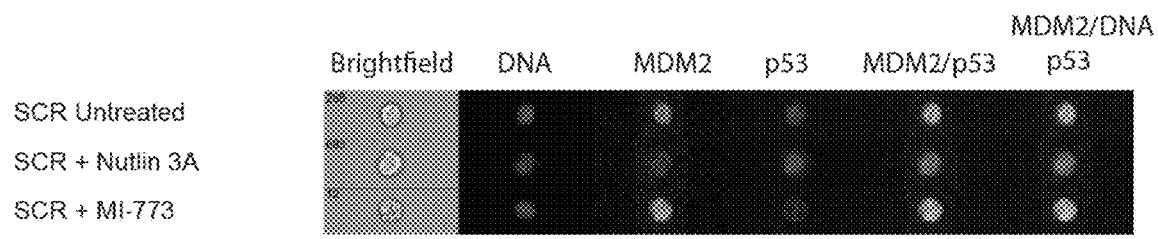
FIG. 64 depicts imaging flow cytometry analysis of MDM2 and p53 levels in HSPCs transduced with scramble control shRNA either untreated or treated with 1 uM of Nutlin3a or 1 uM of MI-773.
Figure 65:
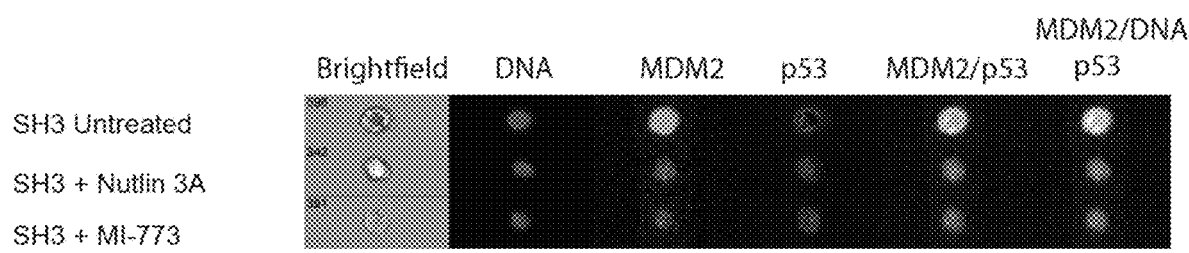
FIG. 65 depicts imaging flow cytometry analysis results for MTF2 knockdown (SH3) HSPCs, demonstrating that these cells exhibit low levels of p53 and high MDM2 levels within the nucleus compared to the scramble (SCR) control cells. The use of two individual MDM2 inhibitors with different chemical backbones, either 1 μM of Nutlin3a or 1 μM of MI-773, reestablished MDM2 and p53 levels to those observed in the scramble untreated control.
Figure 66:
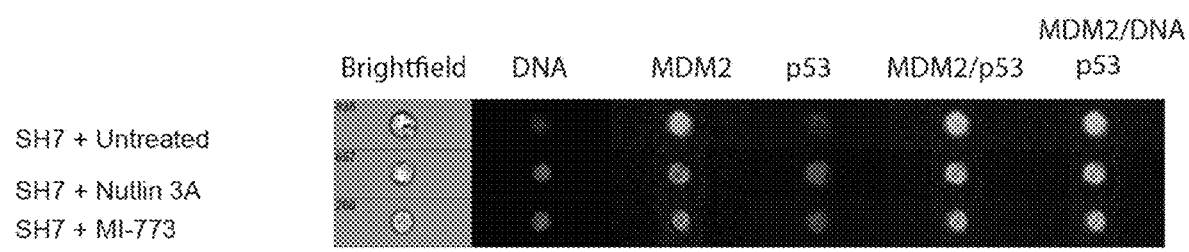
FIG. 66 depicts imaging flow cytometry analysis results of MDM2 and p53 levels in MTF2 knockdown (SH7) HSPCs. MDM2 levels are high and p53 levels are low in untreated cells, but MDM2 levels are low and p53 levels are restored in cells treated with 1 uM of Nutlin3A or 1 uM of MI-773.
Figure 67:
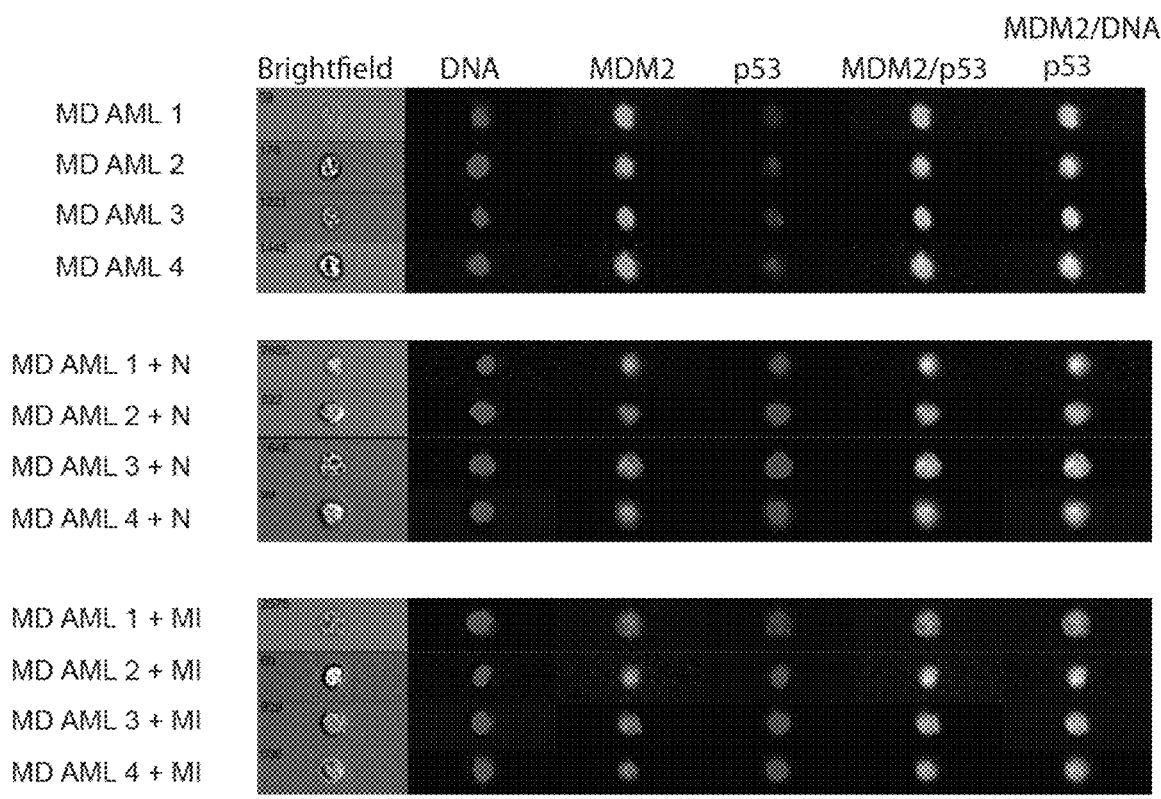
FIG. 67 shows that Lin$^-$CD34$^+$ leukemic cells from refractory MTF2 deficient AML [MD AML] patient bone marrow aspirates showed similar levels in MDM2 and p53 levels as MTF2 knockdown HSPCs. p53 levels were also restored post-MDM2 inhibitor treatment, represented in the panels below (N, Nutlin3A; MI, Mi-773).
Figure 68:
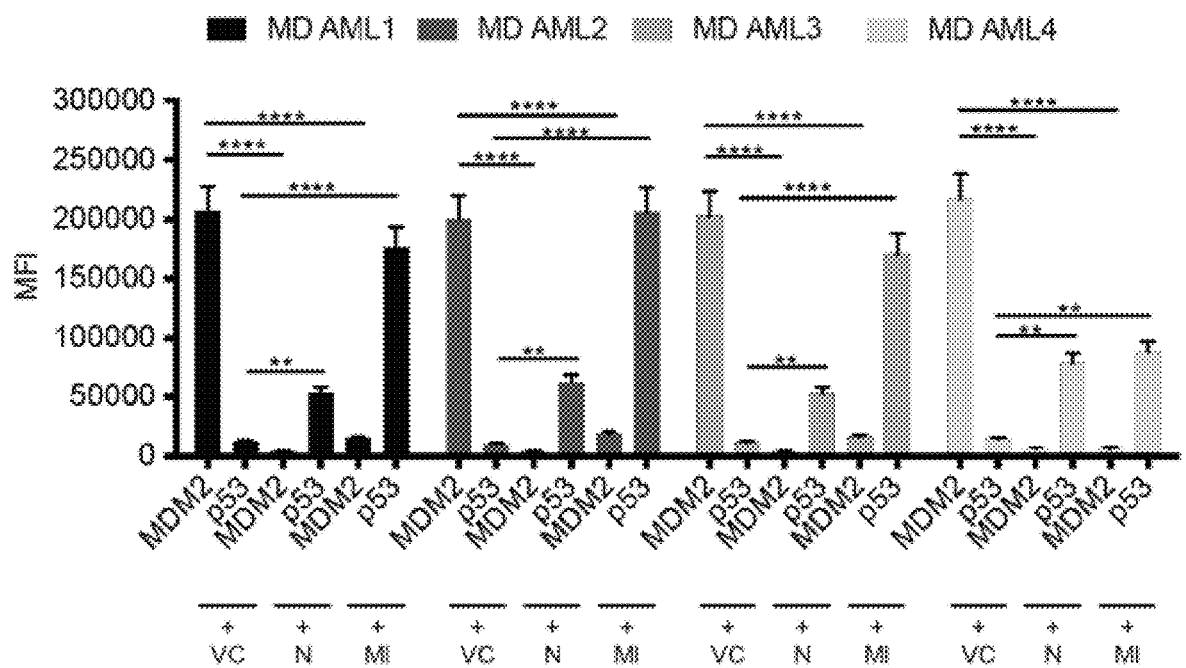
FIG. 68 shows imaging flow cytometry quantification of expression levels of p53 and MDM2 in MTF2 deficient AML Lin$^-$CD34$^+$ cells that were treated with MDM2 inhibitors. MFI was measured within the nucleus using a preset algorithm in the IDEAS software (Amnis). An overlay of p53 and MDM2 is shown in the right column in FIG. 67 representing the overlap within the nucleus used for analysis. (MD AML, MTF2-deficient AML; VC, Vehicle control; N, Nutlin3A; MI, MI-773).

FIGS. 60-63 show DNA damage response (DDR) is hyperactivated in MTF2 KD Lin$^-$CD34$^+$ HSPCs. FIG. 60, Dissection of the Gene Ontology (GO) DDR enrichment term revealed an upregulation of 64% (190 out of 297) of the genes associated with this GO term. FIG. 61, Further analysis of the upregulated DDR genes revealed their role in Nucleotide Excision repair [NER] (35 genes), Double stranded break repair [DSBR] (123 genes), Mismatch Repair [MMR] (13 genes), and Base Excision Repair [BER] (19 genes). FIGS. 62-63, (FIG. 62) RT-qPCR and (FIG. 63) ChIP-qPCR validation of the MTF2 GRN, including DDR genes, in scramble (SCR) or MTF2 (SH3 or SH7) knockdown UCB Lin$^-$ CD34$^+$ cells. AKT3, FZD3, MET, LRP2, LRP6, GLI3, and ROCK2 were predicted and confirmed to be direct targets of MTF2, while FLT3, CDK6, and RAC1 were predicted not to be MTF2 targets and confirmed. Experiments were performed in triplicate. All data represent mean±standard deviation; *$P<0.05$, $P<0.005$, *$P<0.0005$, ****$P<0.00005$ by Two-Way ANOVA.

Figure 90:
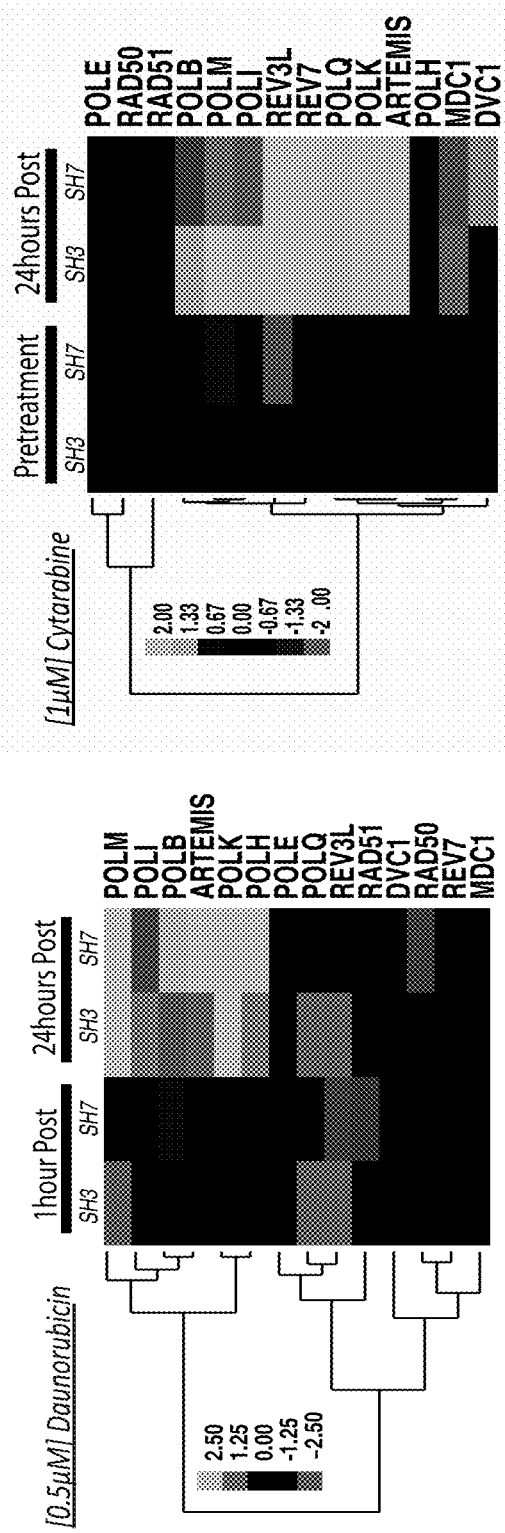
FIG. 90 shows Enhanced DNA Damage Tolerance upon MTF2 Knockdown Lin-CD34+ HSPCs.

Further characterization of DDR genes in MTF2 knockdown (KD) hematopoietic stem and progenitor cells (HSPCs) determined that these cells undergo less DNA damage in response to standard induction drugs Cytarabine and Daunorubicin due to an upregulation of error-prone DNA repair genes (POLH, POLK, POLQ, and ARTEMIS) and a downregulation of genes involved in higher fidelity DNA repair (RAD50 and RAD51) (FIG. 90).

FIG. 90 shows Enhanced DNA Damage Tolerance upon MTF2 Knockdown Lin–CD34+ HSPCs. RT-qPCR analysis of genes associated with the DNA damage response within MTF2 Knockdown Lin-CD34+ hematopoietic progenitors revealed translesion synthesis (TLS), to be highly activated, a pathway allowing cells to replicate through damaged DNA. TLS genes POLK, POLH and POLQ are highly expressed within MTF2 knockdown cells 24 hours post-induction treatment. Interestingly, RAD50 and RAD51, which are genes involved in homologous recombination, were downregulated in MTF2 knockdown cells compared to the scramble control.

Figure 91:
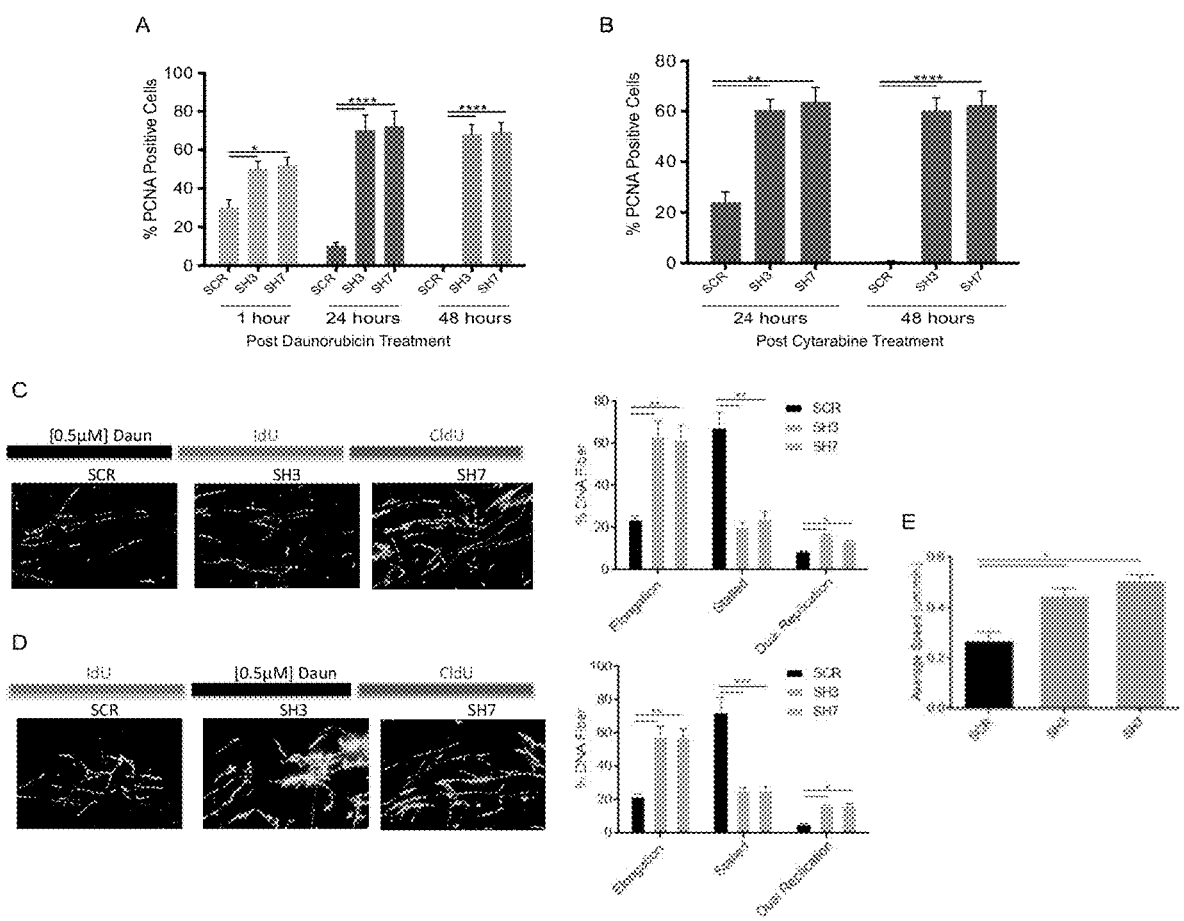
FIG. 91 shows MTF2 deficient HSPCs (Lin-CD34+) tolerate DNA damage throughout replication.

Moreover, MTF2 Knock Down HSPCs tolerate DNA damage and demonstrate higher cell proliferation after Cytarabine or Daunorubicin treatment (FIG. 91). Thus, the proliferating cells are increasing the likelihood of acquiring more DNA mutations.

FIG. 91 shows MTF2 deficient HSPCs (Lin– CD34+) tolerate DNA damage throughout replication. (A, B) PCNA proliferation marker analysis of scramble control (SCR) and MTF2-deficient (SH3, SH7) shRNA knockdown cells 48 hours post-Daunorubicin (A) or Cytarabine (B) treatment. Viable cells were stained for PCNA to assess cell proliferation. MTF2-deficient cells continue to proliferate significantly more than control cells post-treatment. (C), Replication stress was assessed by treating MTF2 deficient HSPCs with Daunorubicin prior to pulsing them with IdU and CIdU. Visually (Left), under replication stress, we observe incorporation of both labels fairly evenly compared with the SCR control which shows predominantly stalled fibers. Quantification of replication structures (Right), revealed more elongating fibers and twice as many dual replication events occurring in MTF2 deficient cells than in the scramble control. (D), To assess these cells' ability to maintain replication after sudden induction of damage, we introduced daunorubicin after the first pulse with IdU, washed, and then pulsed with CIdU (Left). We observed similar results to that seen in (C), in that there are more stalled fibers found in the SCR control and more elongating and dual replicated fibers in MTF2-deficient cells (Right). (E), Assessing replication speed, we observed that MTF2 deficient cells replicate twice as fast as scramble cell control cells. n=3, >200 fibers scored. To obtain an unbiased and blinded analysis, a macro in ImageJ was created which isolates individual fibers and assesses the incorporation of each individual analogue. All data represent mean±standard deviation; *$P<0.05$, $P<0.005$, *$P<0005$ by Two-Way ANOVA.

Figure 92:
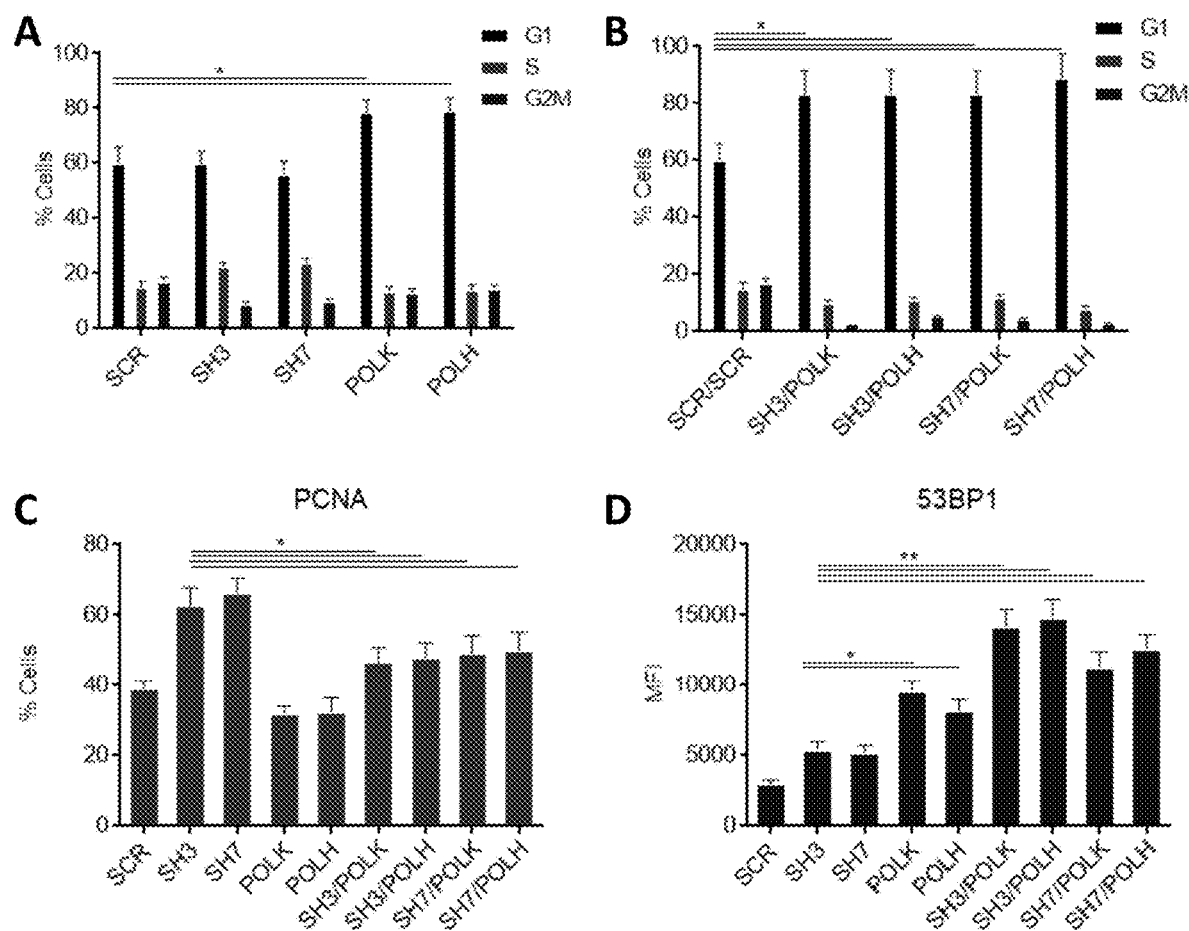
FIG. 92 shows polymerase knockdown within MTF2 knockdown Lin-CD34+ HSPCs leads to decreased proliferation and activation of NHEJ pathway.

It was found that knocking down POLH or POLK in MTF2 KD decreases cell proliferation (FIG. 92).

FIG. 92 shows polymerase knockdown within MTF2 knockdown Lin−CD34+ HSPCs leads to decreased proliferation and activation of NHEJ pathway. A, Percentage of cells actively cycling demonstrate MTF2 knockdown cells cycle much faster, as more cells are in S-phase, while POLK and POLH knockdown cells cycle much slower, with the vast majority of the cells spending their time in the Go/G1 phase. B, Dual transduction of MTF2 with either polymerase knockdown was able to slow down the cycling of the MTF2 deficient cells, as seen by less cells in S-phase and more cells in Go/G1 phase. C, PCNA expression shows polymerase knockdown cells express less PCNA than the MTF2 knockdown cells. Dual MTF2 followed by polymerase knockdown showed higher expression of PCNA than the single polymerase knockdowns but lower expression than the MTF2 knockdown cells. D, Activation of the NHEJ pathway revealed high expression of 53BP1 expression in MTF2 knockdown cells, and even more elevated 53BP1 expression in the single polymerase knockdown, as well as the dual MTF2/polymerase knockdown cells. Experiments were performed in duplicates (n=2). All data represent mean±standard deviation; *$P<0.05$, $P<0.005$, *$P<0.0005$, ****$P<0.00005$ by Two-Way ANOVA.

Thus, inhibiting error-prone DNA repair pathways would decrease cell proliferation and favor homologous recombination in MTF2-deficient AML. Furthermore, recent studies have demonstrated that inhibiting POLQ in breast and ovarian cancer cell lines decreases cell proliferation and therefore could be a potential therapeutic target for these and other types of cancers.[33,35] POLH and/or POLK may similarly be targeted.

REFERENCES

1 Craddock, C. et al. Factors predicting outcome after unrelated donor stem cell transplantation in primary refractory acute myeloid leukaemia. *Leukemia* 25, 808-813, doi: 10.1038/leu.2011.13 (2011).

2 Duval, M. et al. Hematopoietic stem-cell transplantation for acute leukemia in relapse or primary induction failure. *J Clin Oncol* 28, 3730-3738, doi:10.1200/JCO.2010.28.8852 (2010).

3 Thol, F., Schlenk, R. F., Heuser, M. & Ganser, A. How I treat refractory and early relapsed acute myeloid leukemia. *Blood* 126, 319-327, doi:10.1182/blood-2014-10-551911 (2015).

4 Döhner, H. et al. Diagnosis and management of AML in adults: 2017 ELN recommendations from an international expert panel. *Blood* 129, 424-447, doi:10.1182/blood-2016-08-733196 (2017).

5 Kumar, C. C. Genetic abnormalities and challenges in the treatment of acute myeloid leukemia. *Genes Cancer* 2, 95-107, doi:10.1177/1947601911408076 (2011).

6 Gollner, S. et al. Loss of the histone methyltransferase EZH2 induces resistance to multiple drugs in acute myeloid leukemia. *Nat Med* 23, 69-78, doi:10.1038/nm.4247 (2017).

7 Shih, A. H., Abdel-Wahab, O., Patel, J. P. & Levine, R. L. The role of mutations in epigenetic regulators in myeloid malignancies. *Nature reviews. Cancer* 12, 599-612, doi: 10.1038/nrc3343 (2012).

8 Walker, E. et al. Polycomb-like 2 associates with PRC2 and regulates transcriptional networks during mouse embryonic stem cell self-renewal and differentiation. *Cell stem cell* 6, 153-166, doi:10.1016/j.stem.2009.12.014 (2010).

9 Cancer Genome Atlas Research, N. et al. Genomic and epigenomic landscapes of adult de novo acute myeloid leukemia. *N Engl J Med* 368, 2059-2074, doi:10.1056/NEJMoa1301689 (2013).

10 Eppert, K. et al. Stem cell gene expression programs influence clinical outcome in human leukemia. *Nat Med* 17, 1086-1093, doi:10.1038/nm.2415 (2011).

11 Xie, C. et al. Mechanisms of synergistic antileukemic interactions between valproic acid and cytarabine in pediatric acute myeloid leukemia. *Clin Cancer Res* 16, 5499-5510, doi:10.1158/1078-0432.CCR-10-1707 (2010).

12 Come, M. G., Skladanowski, A., Larsen, A. K. & Laurent, G. Dual mechanism of daunorubicin-induced cell death in both sensitive and MDR-resistant HL-60 cells. *Br J Cancer* 79, 1090-1097, doi:10.1038/sj.bjc.6690174 (1999).

13 Olive, P. L. & Banath, J. P. The comet assay: a method to measure DNA damage in individual cells. *Nature protocols* 1, 23-29, doi:10.1038/nprot.2006.5 (2006).

14 Marine, J. C. & Lozano, G. Mdm2-mediated ubiquitylation: p53 and beyond. *Cell death and differentiation* 17, 93-102, doi:10.1038/cdd.2009.68 (2010).

15 McCormack, E. et al. Synergistic induction of p53 mediated apoptosis by valproic acid and nutlin-3 in acute myeloid leukemia. *Leukemia* 26, 910-917, doi:10.1038/leu.2011.315 (2012).

16 Borthakur, G. et al. MDM2 Inhibitor, Nutlin 3a, Induces p53 Dependent Autophagy in Acute Leukemia by AMP Kinase Activation. *PloS one* 10, e0139254, doi: 10.1371/journal.pone.0139254 (2015).

17 Wang, S. et al. SAR405838: an optimized inhibitor of MDM2-p53 interaction that induces complete and durable tumor regression. *Cancer research* 74, 5855-5865, doi: 10.1158/0008-5472.CAN-14-0799 (2014).

18 Zuber, J. et al. Mouse models of human AML accurately predict chemotherapy response. *Genes & development* 23, 877-889, doi:10.1101/gad.1771409 (2009).

19 Francia, G., Cruz-Munoz, W., Man, S., Xu, P. & Kerbel, R. S. Mouse models of advanced spontaneous metastasis for experimental therapeutics. *Nature reviews. Cancer* 11, 135-141, doi:10.1038/nrc3001 (2011).

20 Wunderlich, M. et al. AML cells are differentially sensitive to chemotherapy treatment in a human xenograft model. *Blood* 121, e90-e97, doi:10.1182/blood-2012-10-464677 (2013).

21 Csaszar, E et al. Rapid expansion of human hematopoietic stem cells by automated control of inhibitory feedback signaling. *Cell Stem Cell* 10, 218-229 (2012).

22 Pabst, C. P et al. Identification of small molecules that support human leukemia stem cell activity ex vivo. *Nat. Methods* 11, 436-442 (2014).

22 Al-Khalaf, M. H. et al. Temporal activation of XRCC1-mediated DNA repair is essential for muscle differentiation. *Cell Discov* 2, 15041, doi:10.1038/celldisc.2015.41 (2016).

23 Trapnell, C. et al. Differential gene and transcript expression analysis of RNA-seq experiments with TopHat and Cufflinks. *Nature protocols* 7, 562-578, doi:10.1038/nprot.2012.016 (2012).

24 Reimand, J., Arak, T. & Vilo, J. g: Profiler—a web server for functional interpretation of gene lists (2011 update). *Nucleic acids research* 39, W307-315, doi:10.1093/nar/gkr378 (2011).

25 Reimand, J., Kull, M., Peterson, H., Hansen, J. & Vilo, J. g: Profiler—a web-based toolset for functional profiling of gene lists from large-scale experiments. *Nucleic acids research* 35, W193-200, doi:10.1093/nar/gkm226 (2007).

26 Merico, D., Isserlin, R. & Bader, G. D. Visualizing gene-set enrichment results using the Cytoscape plug-in enrichment map. *Methods in molecular biology* 781, 257-277, doi:10.1007/978-1-61779-276-2_12 (2011).

27 Merico, D., Isserlin, R., Stueker, O., Emili, A. & Bader, G. D. Enrichment map: a network-based method for gene-set enrichment visualization and interpretation. *PloS one* 5, e13984, doi:10.1371/journal.pone.0013984 (2010).

28 Langmead, B. & Salzberg, S. L. Fast gapped-read alignment with Bowtie 2. *Nat Methods* 9, 357-359, doi:10.1038/nmeth.1923 (2012).

29 Shen, L. et al. diffReps: detecting differential chromatin modification sites from ChIP-seq data with biological replicates. *PloS one* 8, e65598, doi:10.1371/journal.pone.0065598 (2013).

30 Quinlan, A. R. & Hall, I. M. BEDTools: a flexible suite of utilities for comparing genomic features. *Bioinformatics* 26, 841-842, doi:10.1093/bioinformatics/btq033 (2010).

31 Love, M. I., Huber, W. & Anders, S. Moderated estimation of fold change and dispersion for RNA-seq data with DESeq2. *Genome Biol* 15, 550, doi:10.1186/s13059-014-0550-8 (2014).

32 Kent, W. J., Zweig, A. S., Barber, G., Hinrichs, A. S. & Karolchik, D. BigWig and BigBed: enabling browsing of large distributed datasets. *Bioinformatics* 26, 2204-2207, doi:10.1093/bioinformatics/btq351 (2010).

33 Mateos-Gomez P A et al., Mammalian polymerase θ promotes alternative NHEJ and suppresses recombination. *Nature* 515(7538): 254-7. (2015) PMID 25642960.

34 Warner et al., Identification of FDA-approved drugs that computationally bind to MDM2. *Chem Biol Drug Des* 80(4):631-7 (2002) PMID: 22703617.

35 Ceccaldi et al., Homologous-recombination-deficient tumours are dependent on Polθ-mediated repair. *Nature* 518(7538):258-62 (2015) PMID: 25642963.

All references cited herein are expressly incorporated by reference in their entireties.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method of predicting response to treatment with an MDM2 inhibitor for a human subject having acute myeloid leukemia (AML), the method comprising:
   measuring levels of expression of one or more analyte comprising MTF2 in a hematological sample obtained from the subject,
   measuring levels of expression of the analytes in a control sample,
   determining that the subject has AML responsive to the MDM2 inhibitor based on the measured levels of expression, wherein decreased expression of MTF2 in the subject sample relative to the control sample is predictive of AML responsive to the MDM2 inhibitor, and
   administering to the subject a treatment comprising the MDM2 inhibitor before or concurrently with a chemotherapy.

2. The method of claim 1, wherein the chemotherapy comprises induction therapy.

3. The method of claim 1, wherein the AML has not previously been treated, has been previously treated, has relapsed, or was not responsive to previous treatment.

4. The method of claim 1, wherein the one or more analyte further comprises H3K27, wherein decreased trimethylation of H3K27 in the sample relative to the control is predictive of AML responsive to the MDM2 inhibitor.

5. The method of claim 1, wherein the one or more analyte further comprises CD92, wherein increased expression is predictive of AML responsive to the MDM2 inhibitor.

6. The method of claim 1, wherein the one or more analyte further comprises at least one of POLQ, POLK, ARTEMIS, and POLH, wherein increased expression is predictive of AML responsive to the MDM2 inhibitor.

7. The method of claim 1, wherein the one or more analyte further comprises at least one of H3K27me3 and CD92, wherein decreased expression of MTF2, decreased trimethylation of H3K27, and increased expression of CD92 in the sample relative to the control are predictive of AML responsive to the MDM2 inhibitor.

8. The method of claim 7, wherein the one or more analyte comprises MTF2, H3K27me3, and CD92.

9. The method of claim 7, wherein the one or more analyte consists of MTF2, H3K27me3, and CD92.

10. The method of claim 7, wherein the one or more analyte comprises MTF2, and CD92.

11. The method of claim 7, wherein the one or more analyte consists of MTF2, and CD92.

12. The method of claim 1, wherein the hematological sample comprises or is obtained from bone marrow aspirate or peripheral blood.

13. The method of claim 1, wherein the hematological sample comprises cells obtained by flow cytometry.

14. The method of claim 1, wherein the analytes are protein.

15. The method of claim 1, wherein the control sample comprises non-refractory AML cells or healthy hematological cells.

16. The method of claim 1, wherein the MDM2 inhibitor comprises a small molecule, a biologic, or an aptamer.

17. The method of claim 16, wherein the small molecule comprises AMG 232.

18. The method of claim 2, wherein the induction therapy comprises an anthracycline and cytarabine.

* * * * *